United States Patent
Gorenstein et al.

(10) Patent No.: US 8,178,834 B2
(45) Date of Patent: May 15, 2012

(54) ION DETECTION AND PARAMETER ESTIMATION FOR N-DIMENSIONAL DATA

(75) Inventors: Marc V. Gorenstein, Needham, MA (US); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 371 days.

(21) Appl. No.: 12/301,301

(22) PCT Filed: May 25, 2007

(86) PCT No.: PCT/US2007/069784
§ 371 (c)(1),
(2), (4) Date: Apr. 21, 2009

(87) PCT Pub. No.: WO2007/140327
PCT Pub. Date: Dec. 6, 2007

(65) Prior Publication Data
US 2009/0294645 A1    Dec. 3, 2009

Related U.S. Application Data

(60) Provisional application No. 60/808,901, filed on May 26, 2006.

(51) Int. Cl.
*H01J 49/26* (2006.01)
(52) U.S. Cl. ............ 250/282; 250/281; 702/22; 702/28
(58) Field of Classification Search .................. 250/281, 250/282, 284, 290, 291, 292, 293; 702/21, 702/22, 23, 24, 25, 26, 27, 28
See application file for complete search history.

(56) References Cited

U.S. PATENT DOCUMENTS

| | | | |
|---|---|---|---|
| 5,440,119 | A | 8/1995 | Labowsky |
| 6,188,064 | B1 | 2/2001 | Köster |
| 6,873,915 | B2 | 3/2005 | Hastings |
| 6,936,814 | B2 | 8/2005 | Hastings |
| 2003/0111596 | A1 | 6/2003 | Becker et al. |
| 2005/0061967 | A1 | 3/2005 | Shvartsburg et al. |
| 2005/0258357 | A1 | 11/2005 | Oliphant et al. |
| 2005/0261838 | A1* | 11/2005 | Andreev et al. .............. 702/22 |
| 2006/0071159 | A1 | 4/2006 | Hashimoto et al. |

(Continued)

FOREIGN PATENT DOCUMENTS
WO    WO 2005/079263 A2    9/2005

OTHER PUBLICATIONS

Valentine, Stephen J., et al., "Toward Plasma Proteome Profiling with Ion Mobility-Mass Spectrometry", Journal of Proteome Research, vol. 5, No. 11, Apr. 10, 2006, pp. 2977-2984, XP55007695, ISSN; 1535-3893.

(Continued)

*Primary Examiner* — David A Vanore
*Assistant Examiner* — Nicole Ippolito
(74) *Attorney, Agent, or Firm* — Muirhead and Saturnelli, LLC

(57) ABSTRACT

Methods and apparatus for LC/IMS/MS analysis involve obtaining noisy raw data from a sample, convolving the data with an artifact-reducing filter, and locating, in retention-time, ion mobility, and mass-to-charge-ratio dimensions, one or more ion peaks of the convolved data.

22 Claims, 34 Drawing Sheets

U.S. PATENT DOCUMENTS

2006/0145070 A1  7/2006  Hondo et al.
2007/0136017 A1* 6/2007  Wang et al. .................... 702/85

OTHER PUBLICATIONS

Taraszka, John A., et al., "Proteome Profiling for Assessing Diversity: Analysis of Individual Heads of Drosophila melanogaster Using LC-Ion Mobility-MS", Journal of Proteome Research, vol. 4, No. 4, Jun. 22, 2005, pp. 1238-1247, XP55007020, ISSN: 1535-3891.

Moon, Myeong Hee, et al., "Nanoflow LC/Ion Mobility/CID/TOF for Proteamics: Analysis of a Human Urinary Proteome", Journal of Proteome Research, vol. 2, No. 6, Jul. 25, 2003, pp. 589-597, XP55007701, ISSN: 1535-3893.

Sowell, R. A., et al., "Nanoflow LC/IMS-MS and LC/IMS-CID/MS of protein mixtures", Journal of the American Society for Mass Spectrometry, Elsevier Science Inc., US, vol. 15, No. 9, Aug. 6, 2004, pp. 1341-1353, XCP004548379, ISSN: 1044-0305.

Taraszka, John A., "Mapping the Proteome of Drosophila melanogaster: Analysis of Embryos and Adult Heads by LC-IMS-MS Methods", Journal of Proteome Research, vol. 4, No. 4, Jun. 22, 2005, pp. 1223-1237, XP55007692, ISSN: 1535-3893.

Liu, et al., "Mapping the Human Plasma Proteome by SCX-LC-IMS-MS", Journal of the American Society for Mass Spectrometry, Elsevier Science Inc., US, vol. 18, No. 7, Apr. 24, 2007, pp. 1249-1264, XP022131656, ISSN: 1044-0305.

Extended European Search Report Dated Dec. 5, 2011.

* cited by examiner

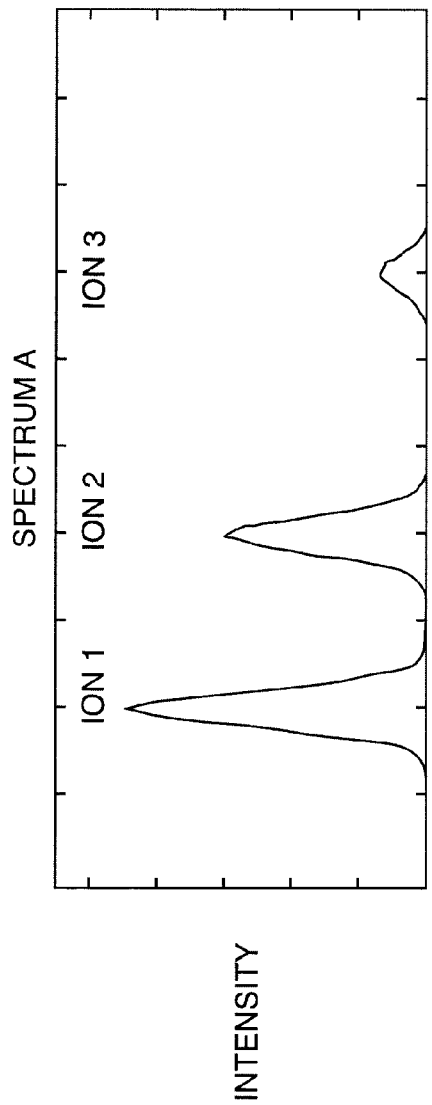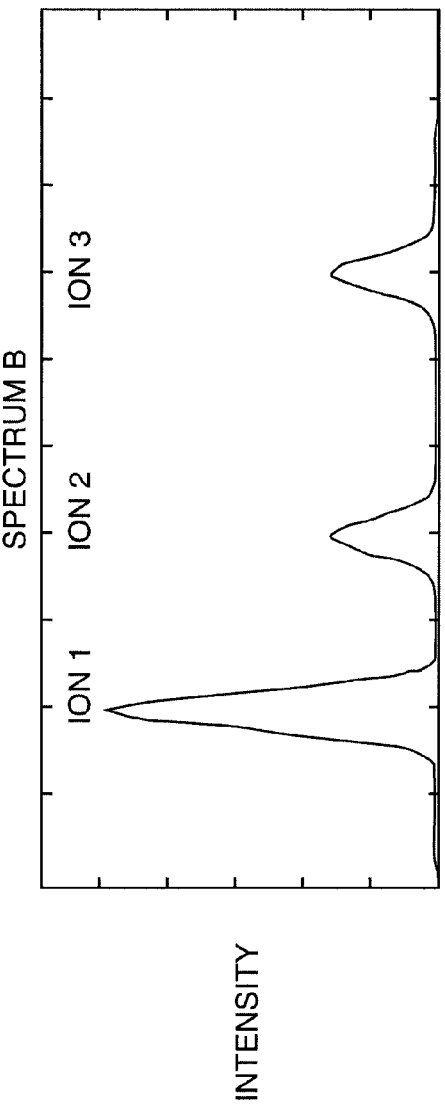

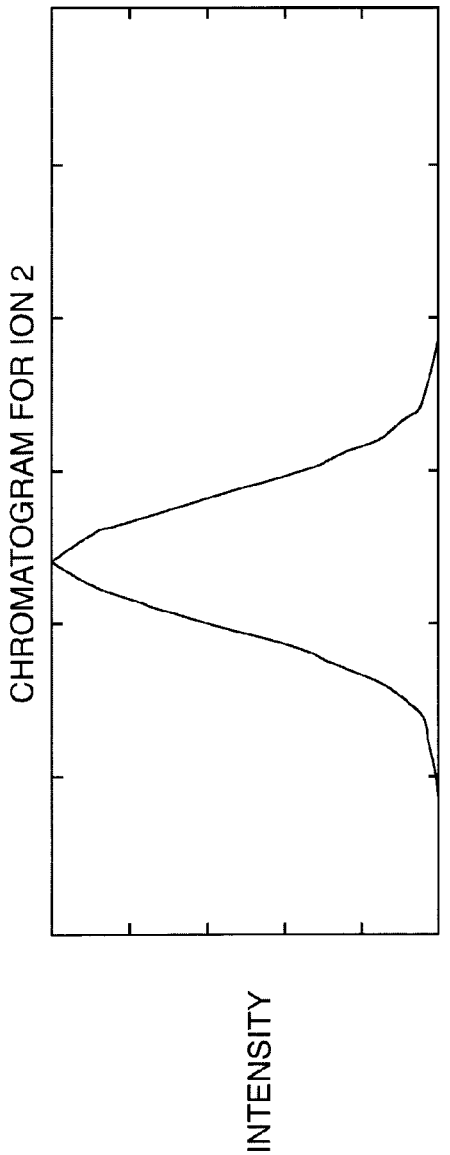
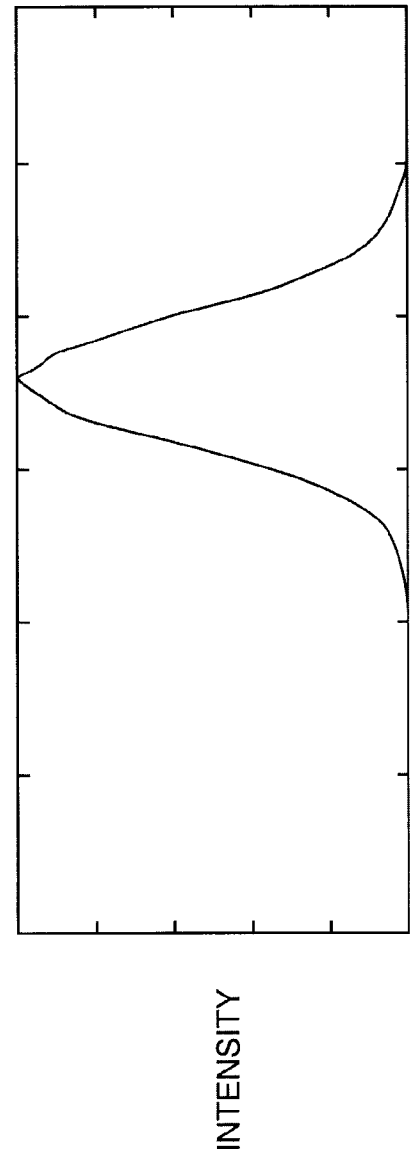
FIG. 4B
FIG. 4C

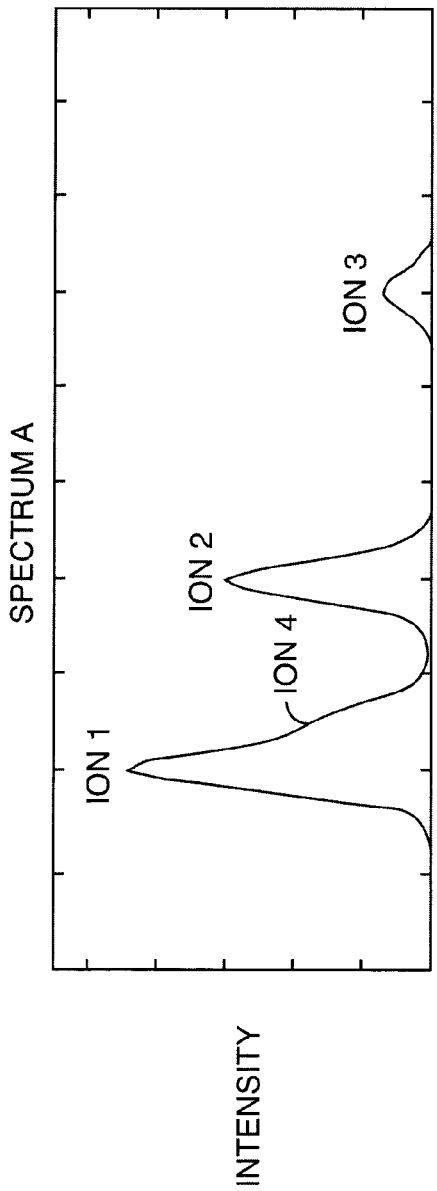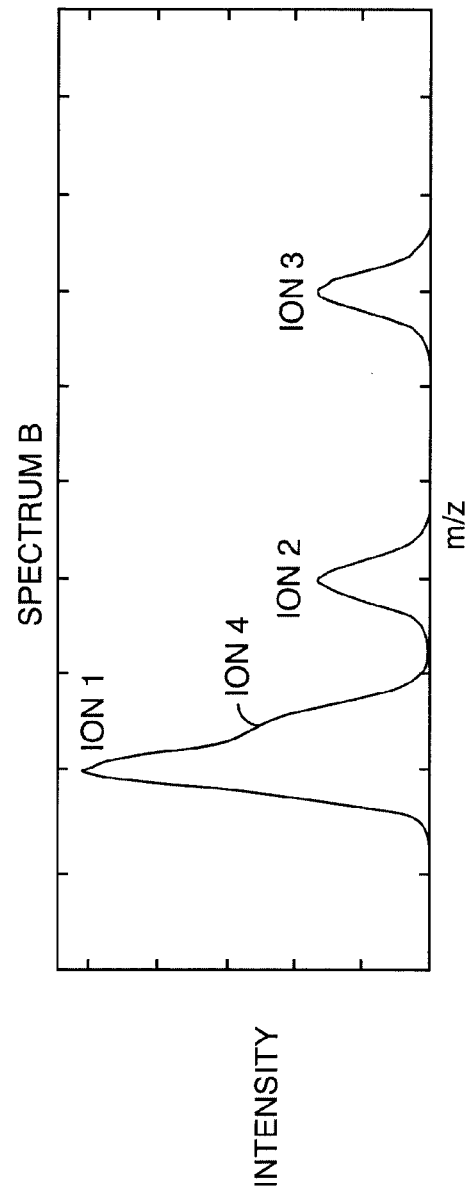

FIG. 16F
SPECTRAL SECOND DERIVITAVE FILTER FILTER, F2
COEFFICIENT NUMBER

FIG. 16E
CHROMATOGRAPHIC SMOOTHING, G2
COEFFICIENT NUMBER

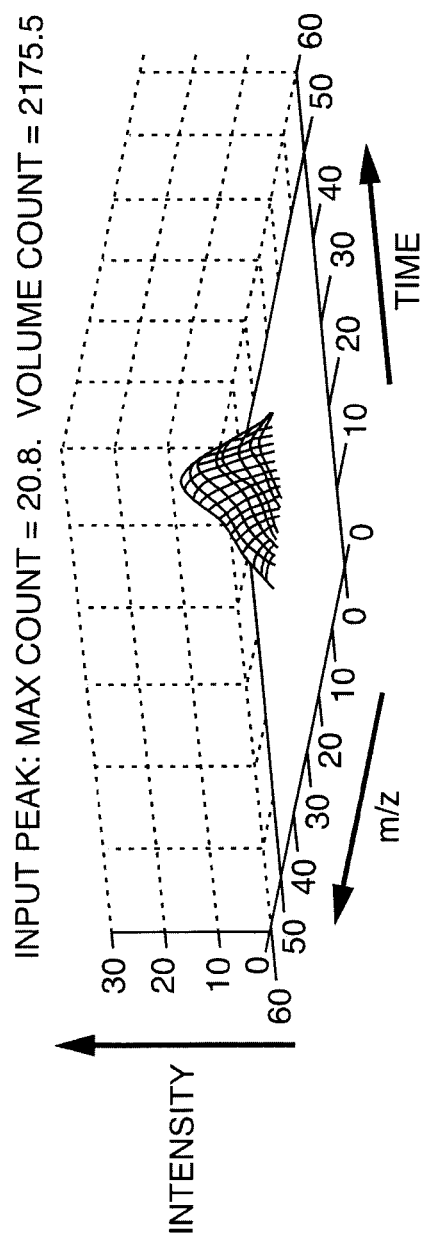
FIG. 17C
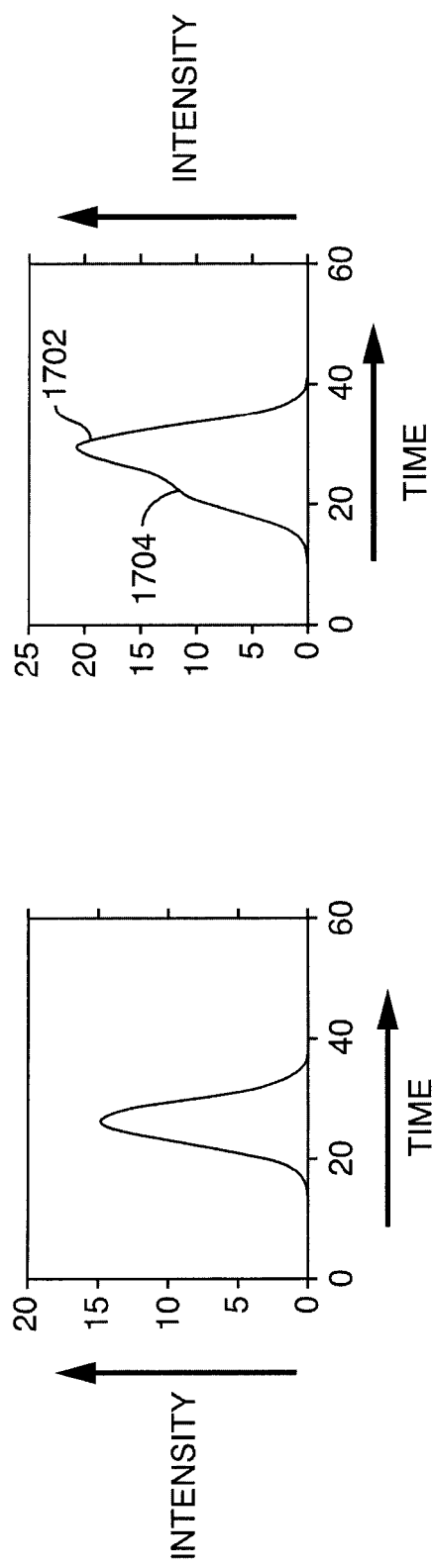
FIG. 17E
FIG. 17D

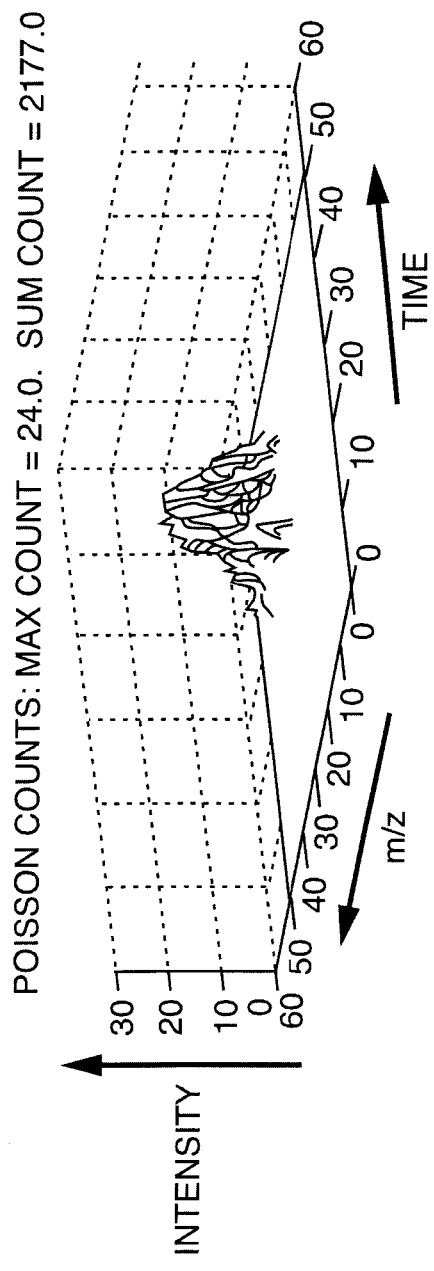
FIG. 17F
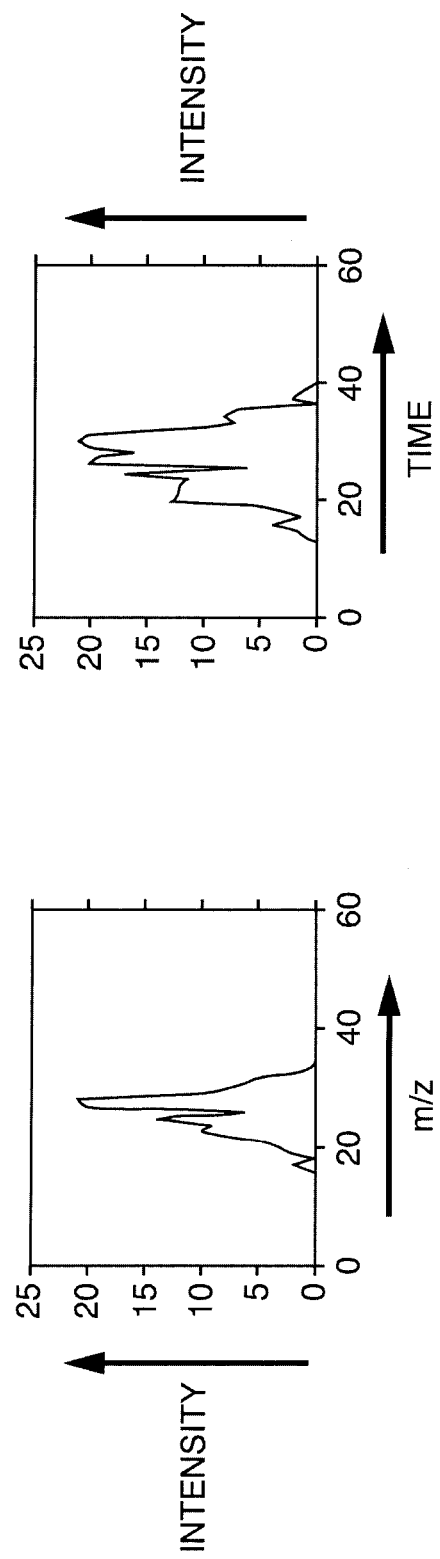
FIG. 17G
FIG. 17H

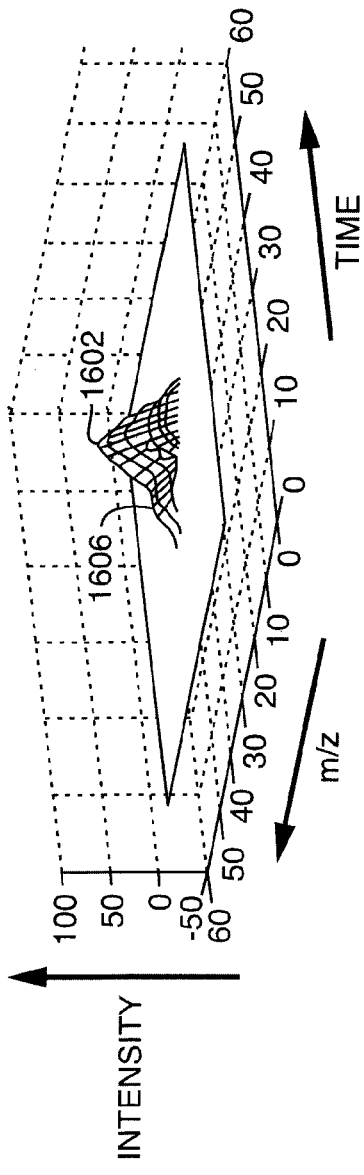
FIG. 17I
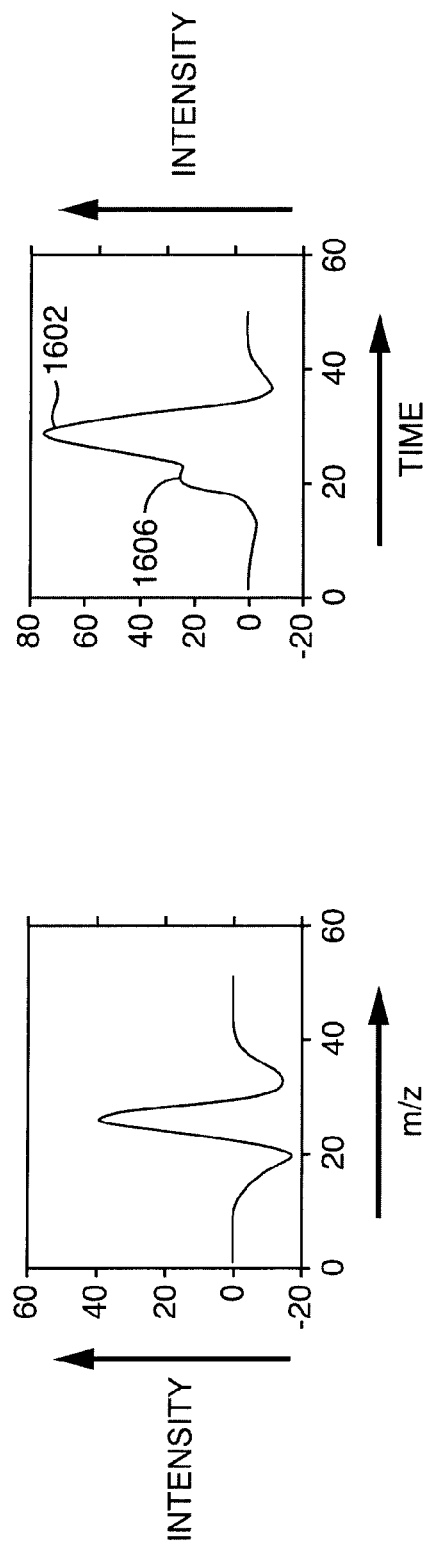
FIG. 17K
FIG. 17J

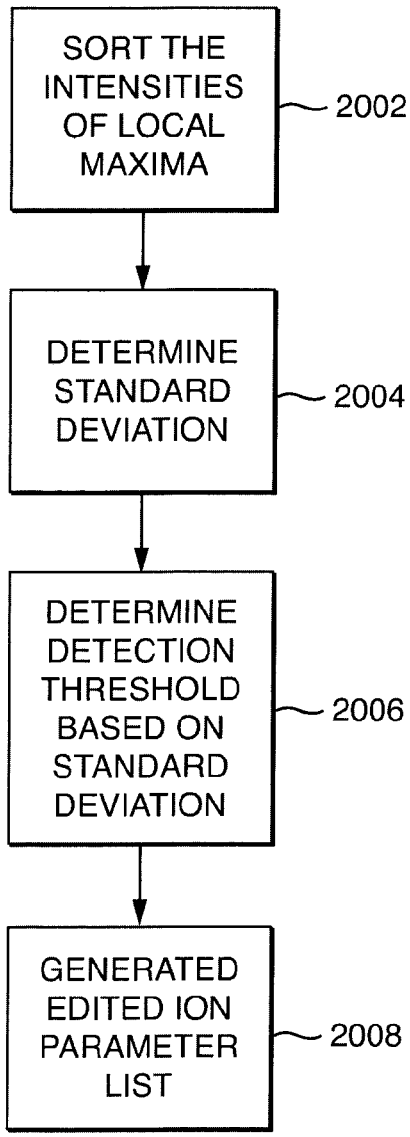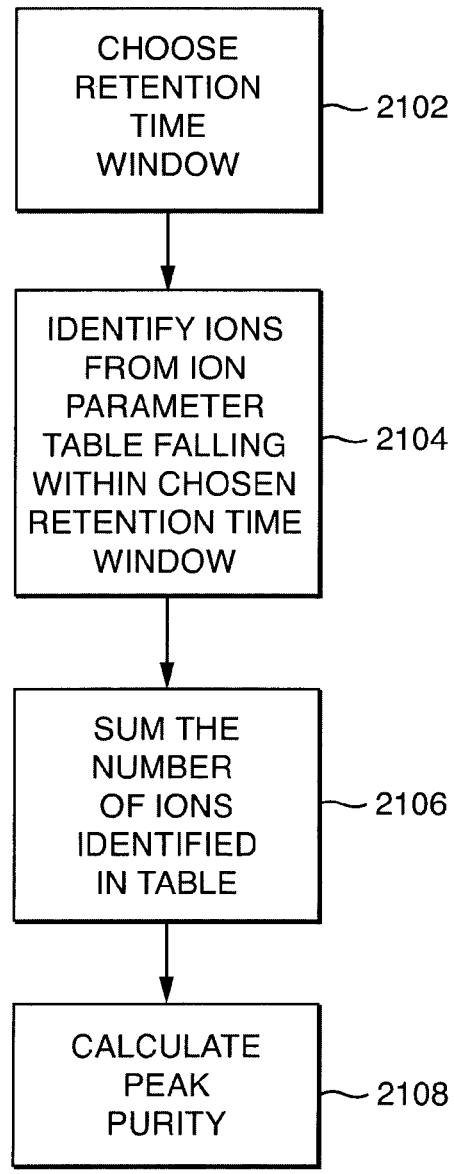
FIG. 20
FIG. 21

ION DETECTION AND PARAMETER ESTIMATION FOR N-DIMENSIONAL DATA

CROSS REFERENCE TO RELATED APPLICATIONS

This application is the national stage of International Application No. PCT/US2007/069784, filed May 25, 2007 and designating the United States, which claims benefit of and priority to U.S. Provisional Application Ser. No. 60/808,901, filed May 26, 2006, the entire contents of which is hereby incorporated by reference in its entirety.

FIELD OF THE INVENTION

The present invention relates generally to analysis of compounds, and, more particularly, to detection and quantification of ions collected by liquid chromatography, ion-mobility spectrometry and mass spectrometry.

BACKGROUND OF THE INVENTION

Mass spectrometers (MS) are used widely for identifying and quantifying molecular species in a sample. During analysis, molecules from the sample are ionized to form ions that are introduced into the mass spectrometer for analysis. The mass spectrometer measures the mass-to-charge ratio (m/z) and intensity of the introduced ions.

Mass spectrometers are limited in the number of different ions reliably detected and quantified within a single sample spectrum. As a result, samples containing many molecular species may produce spectra that are too complex for interpretation or analysis using conventional mass spectrometers.

In addition, the concentration of molecular species often varies over a wide range. Biological samples, for example, typically have a greater number of molecular species at lower concentrations than at higher concentrations. Thus, a significant fraction of ions appear at low concentration. The low concentration is often near the detection limit of common mass spectrometers. Moreover, at low concentration, ion detection suffers from background noise and/or interfering background molecules. Consequently, detection of such low abundance species can be improved by removing as much of the background noise as possible and reducing the number of interfering species that are present in the spectrum.

A chromatographic separation, prior to injecting the sample into the mass spectrometer, is commonly used to reduce the complexity of such spectra. For example, peptides or proteins often produce clusters of ions that elute at a common chromatographic retention time and thus produce peaks that overlap in a spectrum. Separating the clusters from the different molecules, in time, helps to simplify interpretation of the spectra produced by such clusters.

Common chromatographic separation instruments include gas chromatographs (GC) and liquid chromatographs (LC). When coupled to a mass spectrometer, the resulting systems are referred to as GC/MS or LC/MS systems. GC/MS or LC/MS systems are typically on-line systems in which the output of the GC or LC is coupled directly to the MS.

A combined LC/MS system provides an analyst with a powerful means to identify and to quantify molecular species in a wide variety of samples. Common samples contain a mixture of a few or thousands of molecular species. The molecules often exhibit a wide range of properties and characteristics, and each molecular species can yield more than one ion. For example, the mass of a peptide depends on the isotopic forms of its nucleus, and an electrospray interface can ionize peptides and proteins into families of charge states.

In an LC/MS system, a sample is injected into the liquid chromatograph at a particular time. The liquid chromatograph causes the sample to elute over time resulting in an eluent that exits the liquid chromatograph. The eluent exiting the liquid chromatograph is continuously introduced into the ionization source of the mass spectrometer. As the separation progresses, the composition of the mass spectrum generated by the MS evolves and reflects the changing composition of the eluent.

Typically, at regularly spaced time intervals, a computer-based system samples and records the spectrum. In conventional systems, the acquired spectra are analyzed after completion of the LC separation.

After acquisition, conventional LC/MS systems generate one-dimensional spectra and chromatograms. The response (or intensity) of an ion is the height or area of the peak as seen in either the spectrum or the chromatogram. To analyze spectra or chromatograms generated by conventional LC/MS systems, peaks in such spectra or chromatograms that correspond to ions must be located or detected. The detected peaks are analyzed to determine properties of the ions giving rise to the peaks. These properties include retention time, mass-to-charge ratio and intensity.

Mass or mass-to-charge ratio (m/z) estimates for an ion are derived through examination of a spectrum that contains the ion. Retention time estimates for an ion are derived by examination of a chromatogram that contains the ion. The time location of a peak apex in a single mass-channel chromatogram provides an ion's retention time. The m/z location of a peak apex in a single spectral scan provides the ion's m/z value.

A conventional technique for detecting ions using an LC/MS system forms a total ion chromatogram (TIC). Typically, this technique is applied if there are relatively few ions requiring detection. A TIC is generated by summing, within each spectral scan, all responses collected over all m/z values and plotting the sums against scan time. Ideally, each peak in a TIC corresponds to a single ion.

Co-elution of peaks from multiple molecules is one possible problem with this method of detecting peaks in a TIC. As a result of co-elution, each isolated peak seen in the TIC may not correspond to a unique ion. A conventional method for isolating such co-eluted peaks is to select the apex of one peak from the TIC and collect spectra for the time corresponding to the selected peak's apex. The resulting spectral plot is a series of mass peaks, each presumably corresponding to a single ion eluting at a common retention time.

For complex mixtures, co-elution also typically limits summing of spectral responses to sums only over a subset of collected channels, e.g., by summing over a restricted range of m/z channels. The summed chromatogram provides information about ions detected within the restricted m/z range. In addition, spectra can be obtained for each chromatographic peak apex. To identify all ions in this manner, multiple summed chromatograms are generally required.

Another difficulty encountered with peak detection is detector noise. A common technique for mitigating detector noise effects is to signal-average spectra or chromatograms. For example, the spectra corresponding to a particular chromatographic peak can be co-added to reduce noise effects. Mass-to-charge ratio values as well as peak areas and heights can be obtained from analyzing the peaks in the averaged spectrum. Similarly, co-adding chromatograms centered on the apex of a spectral peak can mitigate noise effects in chromatograms and provide more accurate estimates of retention time as well as chromatographic peak areas and heights.

Aside from these problems, additional difficulties are encountered when conventional peak detection routines are used to detect chromatographic or spectral peaks. If performed manually, such conventional methods are both subjective and tedious. When performed automatically, such methods can still be subjective, due to a subjective selection of thresholds for identification of peaks. Further, these conventional methods tend to be inaccurate because they analyze data using only a single extracted spectrum or chromatogram, and do not provide ion parameter estimates having the highest statistical precision or lowest statistical variance. Finally, conventional peak-detection techniques do not necessarily provide uniform, reproducible results for ions at low concentration, or for complex chromatograms, where co-elution and ion interference tend to be common problems.

BRIEF SUMMARY OF THE INVENTION

Some embodiments of the present invention involve analysis instrumentation and methods that entail data of three or more dimensions. For example, some preferred embodiments of the invention involve apparatus that include LC, ion-mobility spectrometry (IMS) and MS. Some aspects of the invention arise from the realization that LC/IMS/MS and other higher dimensional data-generating techniques benefit from efficient data evaluation through use of convolution filters to reduce artifacts caused by noise and/or peak interference. Moreover, temporarily collapsing data in a relatively low, or lowest dimension, such as the ion-mobility dimension, speeds analysis, and allows a higher or highest resolution dimension, such as the mass-spectrometry dimension to identify large portions of collected data that can be ignored during data analysis. Further, the ion-mobility dimension, for example, supports distinguishing of ion peaks that otherwise overlap in other dimensions, such as a retention time and/or mass dimension.

For example, in some LC/IMS/MS-base embodiments, faster, more efficient characterization of data provides ion parameters, such as ion mobility, mass-to-charge ratio (m/z), retention time and ion intensity, which are accurately and optimally estimated by creating a data matrix of data collapsed in the ion-mobility dimension, and convolved with a fast, linear two-dimensional finite impulse response (FIR) filter to generate an output convolved matrix. A peak detection routine is applied to the output convolved matrix to identify peaks corresponding to ions in the sample.

The identified peaks are optionally used to indicate which portions of the original data contain peaks. These indicated portions are optionally convolved with a three-dimensional filter, and ions peaks are then located in all dimensions. Evaluation of the low-resolution dimension supports, for example, elucidation of ion peaks that are overlapped in other dimensions.

Accordingly, in one illustrative embodiment, the invention features a method of LC/IMS/MS analysis. The method includes obtaining noisy raw data from a sample. The data includes a set of three-dimensional data elements each associating an ion-count intensity with a retention-time dimension, an ion-mobility dimension, and a mass-to-charge-ratio dimension, where the noise is associated with ion-peak artifacts. The method further includes: collapsing, in the ion mobility dimension, the set of data elements to obtain a set of collapsed data elements each associating a combined ion-count intensity with the retention-time and mass-to-charge-ratio dimensions; convolving the set of collapsed data elements with an artifact-reducing filter, the filter associated with a two-dimensional matrix, thereby obtaining a convolved set of data elements having reduced peak artifacts; locating, in the retention-time and mass-to-charge-ratio dimensions, ion peaks of the convolved collapsed set of data elements; selecting one or more portions of the raw data for further analysis, in response to the locations of the ion peaks of the convolved set of data elements; and locating, at least in the ion mobility dimension, one or more ion peaks for each of the portions of raw data.

In a second illustrative embodiment, the invention features a method of N-dimensional analysis. The method includes: obtaining noisy data from a sample, the data including a set of data elements each associating an ion-count intensity with at least three dimensions of differing resolution; convolving the set of data elements with an artifact-reducing filter to produce a convolved set of data elements; and locating one or more ion peaks in the convolved set of data elements.

In another aspect, the invention involves chemical processing apparatus. The apparatus includes a control unit that is configured to implement, for example, one of the above-described methods.

BRIEF DESCRIPTION OF THE DRAWINGS

FIG. 16E illustrates the cross section of an exemplary one-dimensional smoothing filter g2 in the chromatographic direction according to an embodiment of the present invention.

FIG. 16F illustrates the cross section of an exemplary one-dimensional second-derivative filter f2 in the spectral (m/z) direction according to an embodiment of the present invention.

FIG. 17C illustrates a simulation of two LC/MS peaks having equal mass and that are nearly, but not identically, co-incident in time.

FIG. 17D illustrates the peak cross section in mass of the two-peak simulation of FIG. 17C.

FIG. 17E illustrates the peak cross section in time of the two-peak simulation of FIG. 17C.

FIG. 17F illustrates the effect of adding counting (shot) noise to the two-peak simulation of FIG. 17C.

FIG. 17G illustrates the peak cross section in mass of the added noise two-peak simulation of FIG. 17F.

FIG. 17H illustrates the peak cross section in time of the added noise two-peak simulation of FIG. 17F.

FIG. 17I illustrates the result convolving a rank-2 filter with simulated data of FIG. 17F.

FIG. 17J illustrates the peak cross section in mass of the result illustrated in FIG. 17I.

FIG. 17K illustrates the peak cross section in time of the result illustrated in FIG. 17I.

FIG. 20 is a flow chart for a method for determining appropriate thresholds according to an embodiment of the present invention.

FIG. 21 is a flow chart for a method for determining a peak purity metric according to an embodiment of the present invention.

DETAILED DESCRIPTION OF THE INVENTION

Definitions

Figure 1:
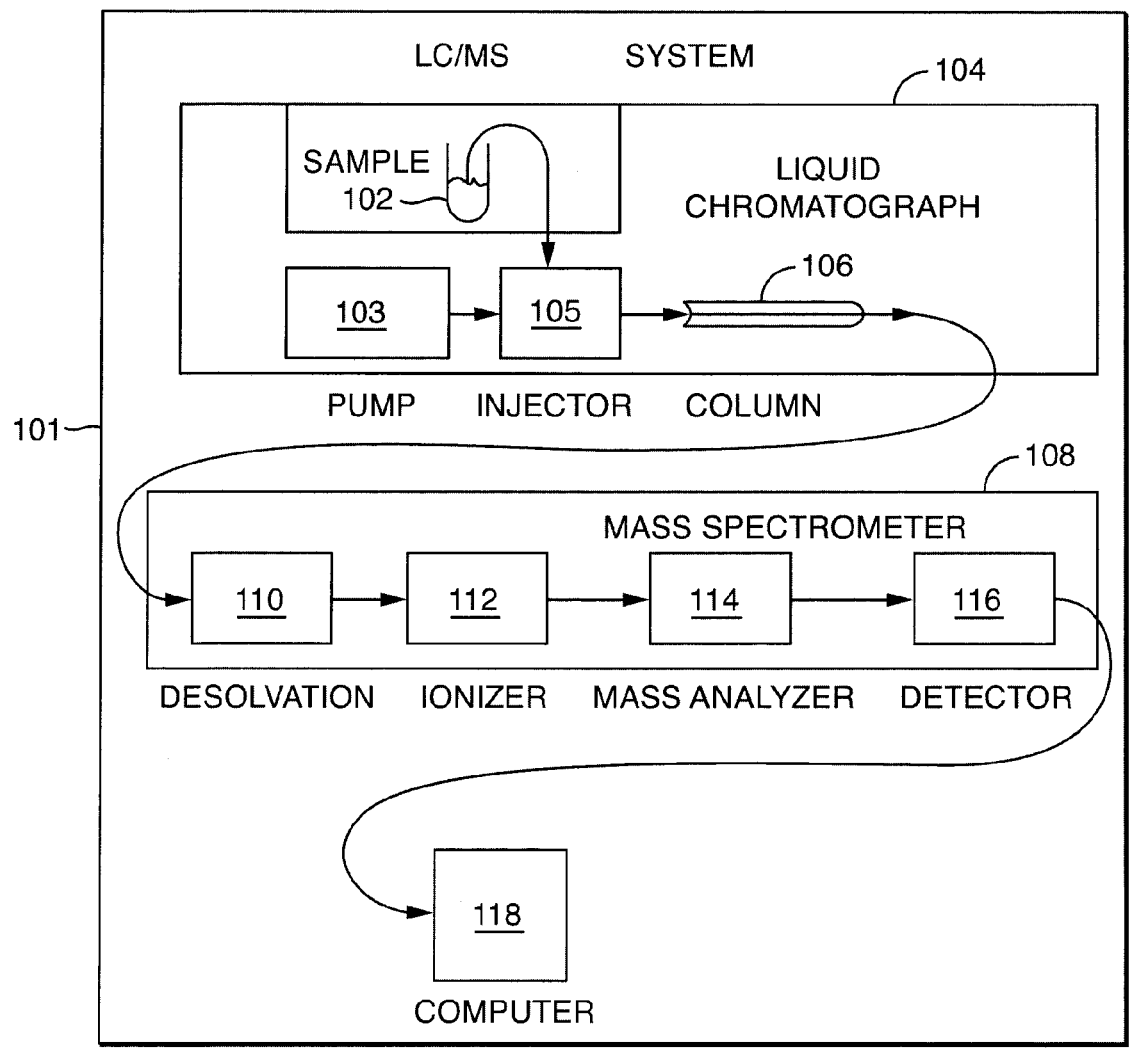
FIG. 1 is a schematic diagram of an exemplary LC/MS system according to an embodiment of the present invention.

"Chromatography"—refers to equipment and/or methods used in the separation of chemical compounds. Chromatographic equipment typically moves fluids and/or ions under pressure and/or electrical and/or magnetic forces. The word "chromatogram," depending on context, herein refers to data or a representation of data derived by chromatographic means. A chromatogram can include a set of data points, each of which is composed of two or more values; one of these values is often a chromatographic retention time value, and the remaining value(s) are typically associated with values of intensity or magnitude, which in turn correspond to quantities or concentrations of components of a sample.

The invention supports the generation and analysis of chromatographic data. Some embodiments of the invention involve instruments that include a single module that separates sample compounds while other embodiments involve multiple modules. For example, principles of the invention are applicable to liquid chromatography apparatus as well as to, for example, apparatus that include liquid chromatography, ion-mobility spectrometry and mass spectrometry modules. In some multi-module-based embodiments, a chromatographic module is placed in fluidic communication with an ion-mobility spectrometry module through an appropriate interface; the IMS module is, in turn, interfaced to a mass-spectrometry module through use of an appropriate interface, such as an electrospray-ionization interface. Some appropriate interfaces at times create or maintain separated materials in an ionic form. A stream of sample fluid is typically vaporized, ionized, and delivered to an inlet orifice of a mass-spectrometry module.

Thus, some embodiments produce multi-dimensional data composed of sets of data elements, each of which has valves associated with measurement dimensions such as retention time (derived from a chromatography module), ion mobility and mass-to-charge ratio. A unique set of dimensional valves is experimentally linked to, for example, a valve of ion intensity as measured in a mass spectrometry module.

Protein—herein refers to a specific primary sequence of amino acids assembled as a single polypeptide.

Peptide—herein refers to a specific sequence of amino acids assembled as a single polypeptide contained within the primary sequence of a protein.

Precursor peptides—tryptic peptides (or other protein cleavage products) that are generated using a protein-cleavage protocol. The precursors are optionally separated chromatographically and passed to a mass spectrometer. An ion source ionizes these precursor peptides to typically produce a positively charged, protenated form of the precursor. The mass of such positively charged protenated precursor ion is herein referred as the "mwHPlus" or "MH+" of the precursor. In the following, the term "precursor mass" refers generally to the protenated, mwHPlus or MH+ mass of the ionized, peptide precursor.

Fragments—Multiple types of fragments can occur in LC/MS analyses. In the case of tryptic peptide precursors, fragments can include polypeptide ions that are produced from collisional fragmentation of the intact peptide precursors and whose primary amino acid sequence is contained within the originating precursor peptide. Y-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$) molecules from the precursor.

Y-ions and B-ions—If a peptide fragments at the peptide bond, and if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in Roepstorff and Fohlman, Biomed Mass Spectrom, 1984; 11(11):601 and Johnson et al, Anal. Chem. 1987, 59(21): 2621:2625.

Retention time—in context, typically refers to the point in a chromatographic profile at which an entity reaches its maximum intensity.

Ions—a peptide, for example, typically appears in an LC/MS analysis as an ensemble of ions due to the natural abundance of the isotopes of the constituent elements. An ion has, for example, a retention time and an m/z value. The mass spectrometer (MS) detects only ions. The LC/MS technique produces a variety of observed measurements for every detected ion. This includes: the mass-to-charge ratio (m/z), mass (m), the retention time, and the signal intensity of the ion, such as a number of ions counted.

Noise—used herein to refer to a raw-data component arising from sources such as detector noise, including Poisson noise due to counting statistics and Gaussian, Johnson noise due to thermal effects, and other noise sources that tend to hide real ion peaks or produce false ion peaks.

Artifact—refers herein to false peaks in raw data, as arise from, for example, noise, peak interference and peak overlap.

Generally, an LC/IMS/MS analysis optionally provides an empirical description of, for example, a peptide in terms of its mass, charge, retention time, mobility and total intensity. When a peptide elutes from a chromatographic column, it elutes over a specific retention time period and reaches its maximum signal at a single retention time. After ionization and (possible) fragmentation, the peptide appears as a related set of ions. The different ions in the set correspond to different isotopic compositions and charges of the common peptide. Each ion within the related set of ions produces a single peak retention time and peak shape. Since these ions originate from a common peptide, the peak retention time and peak shape of each ion is identical, within some measurement tolerance. The MS acquisition of each peptide produces multiple ion detections for all isotopes and charge states, all sharing the same peak retention-time and peak shape within some measurement tolerance.

In an LC/MS separation, a single peptide (precursor or fragment) produces many ion detections, which appear as a cluster of ions, having multiple charge states. Deconvolution of these ion detections from such a cluster, indicates the presence of a single entity of a unique monoisotopic mass, at a specific retention time, of a measured signal intensity, in a charge state.

Embodiments of the present invention can be applied to a variety of applications including large-molecule, non-volatile analytes that can be dissolved in a solvent. Although embodiments of the present invention are described hereinafter with respect to LC, LC/MS or LC/IMS/MS systems, embodiments of the present invention can be configured for operation with other analysis techniques, including GC, GC/MS and GC/IMS/MS systems. For context, embodiments that utilize 1-D and 2-D matrices for analysis of LC/MS data are described first, with reference to FIGS. 1-23. Subsequently, some preferred embodiments of the present invention, relating to LC/IMS/MS and higher dimensional techniques, are described with reference to FIG. 24.

FIG. 1 is a schematic diagram of an exemplary LC/MS system 101 according to an embodiment of the present invention. LC/MS analysis is performed by automatically or manually injecting a sample 102 into a liquid chromatograph 104. A high pressure stream of chromatographic solvent provided by pump 103 and injector 105 forces sample 102 to migrate through a chromatographic column 106 in liquid chromatograph 104. Column 106 typically comprises a packed column of silica beads whose surface comprises bonded molecules. Competitive interactions between the molecular species in the sample, the solvent and the beads determine the migration velocity of each molecular species.

A molecular species migrates through column 106 and emerges, or elutes, from column 106 at a characteristic time. This characteristic time commonly is referred to as the molecule's retention time. Once the molecule elutes from column 106, it can be conveyed to a detector, such as a mass spectrometer 108.

Figure 2:
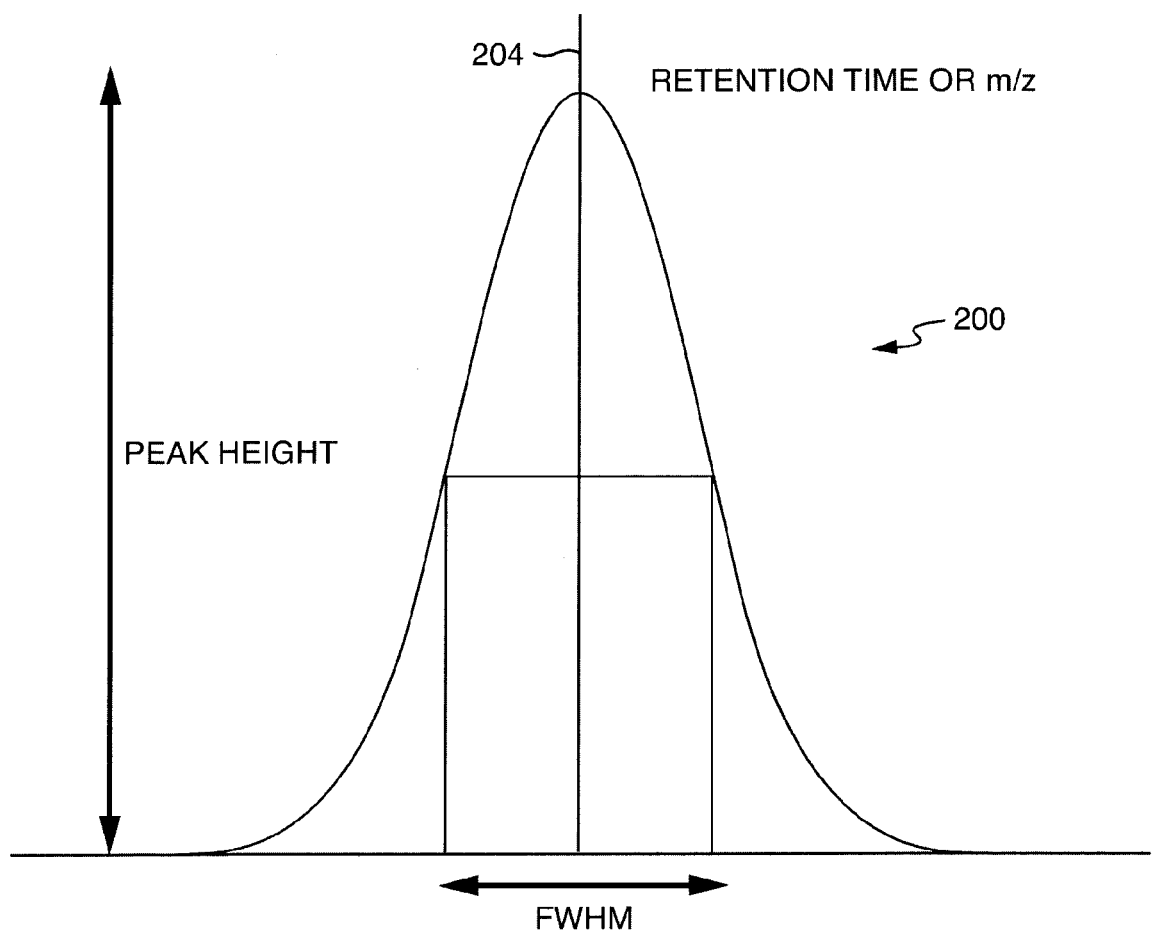
FIG. 2 is a diagram of an exemplary chromatographic or spectral peak.

A retention time is a characteristic time. That is, a molecule that elutes from a column at retention time t in reality elutes over a period of time that is essentially centered at time t. The elution profile over the time period is referred to as a chromatographic peak. The elution profile of a chromatographic peak can be described by a bell-shaped curve. The peak's bell shape has a width that typically is described by its full width at half height, or half-maximum (FWHM). The molecule's retention time is the time of the apex of the peak's elution profile. Spectral peaks appearing in spectra generated by mass spectrometers have a similar shape and can be characterized in a similar manner. FIG. 2 illustrates an exemplary chromatographic or spectral peak 202 having a peak apex 204. The FWHM and height or the peak 202 are also illustrated in FIG. 2.

For purposes of subsequent description, peaks are assumed to have a Gaussian profile as shown in FIG. 2. For a Gaussian profile, the FWHM is approximately 2.35 times the standard deviation $\sigma$ of the Gaussian profile.

Chromatographic peak width is independent of peak height and is substantially a constant characteristic of a molecule for a given separation method. In the ideal case, for a given chromatographic method all molecular species would elute with the same peak width. However, typically peak widths change as a function of retention time. For example, molecules that elute at the end of a separation can display peak widths that are several times wider than peak widths associated with molecules that elute early in the separation.

In addition to its width, a chromatographic or spectral peak has a height or area. Generally, the height and area of the peak are proportional to the amount or mass of the species injected into the liquid chromatograph. The term intensity commonly refers to either the height or area of the chromatographic or spectral peak.

Although chromatographic separation is a substantially continuous process, detectors analyzing the eluent typically sample the eluent at regularly spaced intervals. The rate at which a detector samples the eluent is referred to as the sample rate or sample frequency. Alternatively, the interval at which a detector samples the eluent is referred to as the sampling interval or sample period. Because the sample period must be long enough so that the system adequately samples the profile of each peak, the minimum sample period is limited by the chromatographic peak width. As an example, the sample period can be set so that approximately five (5) measurements are made during the FWHM of a chromatographic peak.

In an LC/MS system, the chromatographic eluent is introduced into a mass spectrometer (MS) 108 for analysis as shown in FIG. 1. MS 108 comprises a desolvation system 110, an ionizer 112, a mass analyzer 114, a detector 116, and a computer 118. When the sample is introduced into MS 108, desolvation system 110 removes the solvent, and ionizing source 112 ionizes the analyte molecules. Ionization methods to ionize molecules that evolve from LC 104 include electron-impact (EI), electrospray (ES), and atmospheric chemical ionization (APCI). Note that in APCI, the order of ionization and desolvation is reversed.

The ionized molecules are then conveyed to mass analyzer 114. Mass analyzer 114 sorts or filters the molecules by their mass-to-charge ratio. Mass analyzers, such as mass analyzer 114 that are used to analyze ionized molecules in MS 108 include quadrupole mass analyzers (Q), time-of-flight (TOF) mass analyzers, and Fourier-transform-based mass spectrometers (FTMS).

Mass analyzers can be placed in tandem in a variety of configurations, including, e.g., quadrupole time-of-flight (Q-TOF) mass analyzers. A tandem configuration enables on-line collision modification and analysis of an already mass-analyzed molecule. For example, in triple quadrupole based massed analyzers (such as Q1-Q2-Q3 or Q1-Q2-TOF mass analyzers), the second quadrupole (Q2), imports accelerating voltages to the ions separated by the first quadrupole (Q1). These ions, collide with a gas expressly introduced into Q2. The ions fragment as a result of these collisions. Those fragments are further analyzed by the third quadrupole (Q3) or by the TOF. Embodiments of the present invention are applicable to spectra and chromatograms obtained from any mode of mass-analysis such as those described above.

Molecules at each value for m/z are then detected with detection device 116. Exemplary ion detection devices include current measuring electrometers and single ion counting multi-channel plates (MCPs). The signal from an MCP can be analyzed by a descriminator followed by a time-domain-converter (TDC) or by an analog to digital (ATD) converter. For purposes of the present description, an MCP detection-based system is assumed. As a result, detector response is represented by a specific number of counts. This detector response (i.e., number of counts) is proportional to the intensity of ions detected at each mass-to-charge-ratio interval.

An LC/MS system outputs a series of spectra or scans collected over time. A mass-to-charge spectrum is intensity plotted as a function of m/z. Each element, a single mass-to-charge ratio, of a spectrum is referred to as a channel. Viewing a single channel over time provides a chromatogram for the corresponding mass-to-charge ratio. The generated mass-to-charge spectra or scans can be acquired and recorded by computer 118 and stored in a storage medium such as a hard-disk drive that is accessible to computer 118. Typically, a spectrum or chromatogram is recorded as an array of values and stored by computer system 118. The array can be displayed and mathematically analyzed.

The specific functional elements that make up an MS system, such as MS 108, can vary between LC/MS systems. Embodiments of the present invention can be adapted for use with any of a wide range of components that can make up an MS system.

After chromatographic separation and ion detection and recordation, the data is analyzed using a post-separation data analysis system (DAS). In an alternate embodiment of the present invention, the DAS performs analysis in real-time or near real-time. The DAS is generally implemented by computer software executing on a computer such as computer 118 shown in FIG. 1. Computers that can be configured to execute the DAS as described herein are well known to those skilled in the art. The DAS is configured to perform a number of tasks, including providing visual displays of the spectra and/or chromatograms as well as providing tools for performing mathematical analysis on the data. The analyses provided by the DAS include analyzing the results obtained from a single injection and/or the results obtained from a set of injections to be viewed and further analyzed. Examples of analyses applied to a sample set include the production of calibration curves for analytes of interest, and the detection of novel compounds present in the unknowns, but not in the controls. A DAS according to embodiments of the present invention is described herein.

Figure 3C:
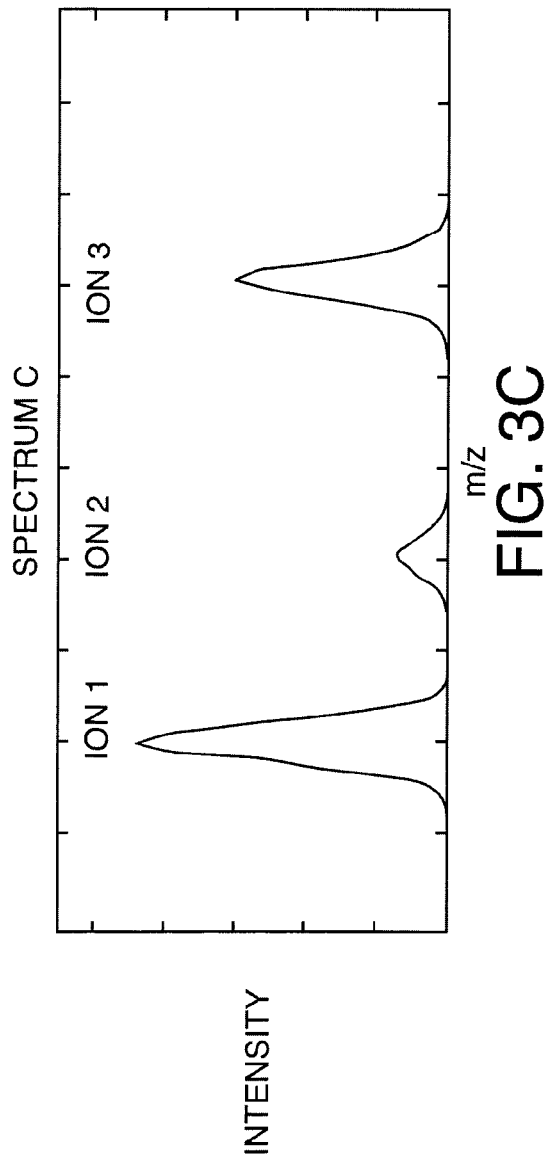
FIG. 3 illustrates exemplary spectra for three ions produced during an exemplary LC/MS experiment for three times.

FIG. 3 illustrates exemplary spectra for three ions (ion 1, ion 2 and ion 3) produced during an exemplary LC/MS experiment. Peaks associated with ion 1, ion 2 and ion 3 appear within a limited range of retention time and m/z. For the present example, it is assumed that the mass-to-charge ratios of ion 1, ion 2 and ion 3 are different, and that the molecular parents of the ions eluted at nearly, but not exactly, identical retention times. As a result, the elution profiles of the respective molecules overlap or co-elute. Under these assumptions, there is a time when all three molecules are present in the ionizing source of the MS. For example, the exemplary spectrum illustrated in FIG. 3 were collected when all three ions were present in the MS ionization source. This is apparent because each spectrum exhibits a peak associated with each of ions 1, 2 and 3. As can be seen in the exemplary spectra illustrated in FIG. 3, there is no overlap of spectral peaks. The lack of overlap indicates that the mass spectrometer resolved these spectral peaks. The location of the apex of the peaks corresponding to each of ions 1, 2 and 3 represents its mass-to-charge ratio.

It is not possible to determine precise retention times or even relative retention times at which ions in a spectrum elute using only a single spectrum. For example, it can be seen that at the time the data for Spectrum B was collected, all three molecules associated with ions 1, 2 and 3 were eluting from the column. However, analyzing only Spectrum B, it is not possible to determine a relationship between the elution times of ions 1, 2 and 3. Thus, Spectrum B could have been collected at a time corresponding to the beginning of a chromatographic peak, as the molecule began to elute from the column, or from the end of the chromatographic peak, when the molecule was nearly finished eluting or at some time in between.

More accurate information related to retention time can be obtained by examining successive spectra. This additional information can include the retention time of the eluting molecules or at least the elution order. For example, assume Spectra A, B, and C shown in FIG. 3 were collected successively such that Spectrum A was collected at time tA; Spectrum B was collected at a later time tB; and Spectrum C was collected at time tC, which is a time later than time tB. Then, the elution order of the respective molecules can be determined by examining the relative heights of the peaks appearing in spectra successively collected as time progresses from tA to tC. Such examination reveals that as time progresses ion 2 decreases in intensity relative to ion 1, and that ion 3 increases in intensity relative to ion 1. Therefore, ion 2 elutes before ion 1, and ion 3 elutes after ion 1.

Figure 4A:
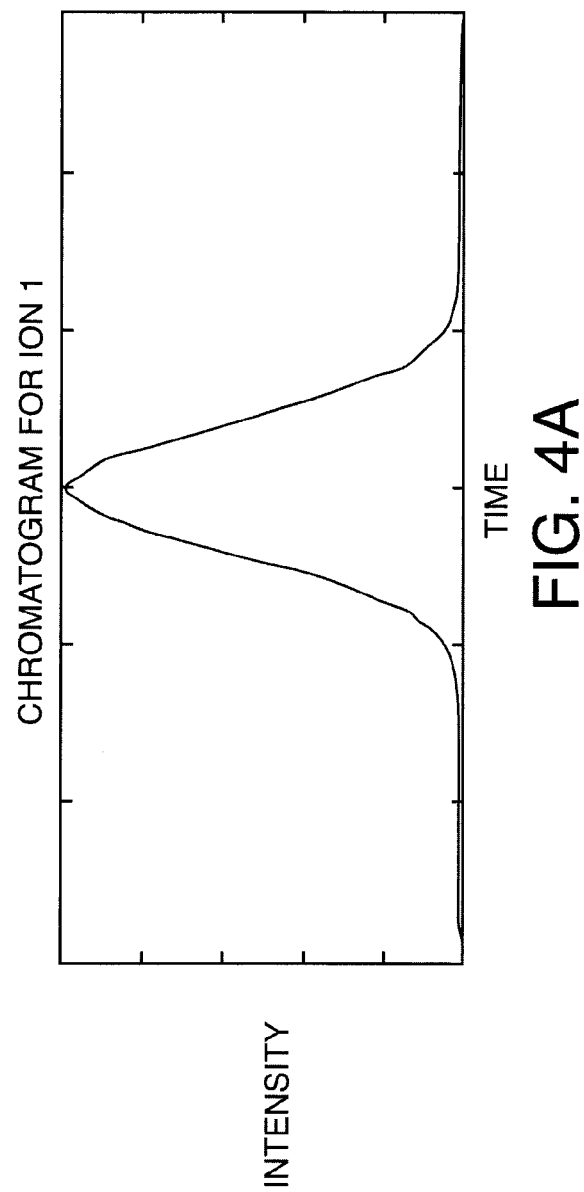
FIG. 4 illustrates chromatograms corresponding to the exemplary ions of FIG. 3.

This elution order can be verified by generating chromatograms corresponding to each peak found in a spectrum. This can be accomplished by obtaining the m/z value at the apex of each of the peaks corresponding to ions 1, 2 and 3. Given these three m/z values, the DAS extracts from each spectrum the intensity obtained at that m/z for each scan. The extracted intensities are then plotted versus elution time. Such a plot is illustrated in FIG. 4. It can be seen that the plots in FIG. 4 represent the chromatograms for ions 1, 2, and 3 at the m/z values obtained by examining the peaks in FIG. 3. Each chromatogram contains a single peak. Examination of the chromatograms for ions 1, 2 and 3 as illustrated in FIG. 4 confirms that ion 2 elutes at the earliest time and that ion 3 elutes at the latest time. The apex location in each of the chromatograms shown in FIG. 4 represents the elution time for the molecule corresponding to the respective ions.

With this introduction in mind, embodiments of the present invention relate to analyzing experimental analysis outputs, such as spectra and chromatograms, to optimally detect ions and quantify parameters related to the detected ions. Moreover, embodiments of the present invention can provide significantly simplified spectra and chromatograms.

Figure 5:
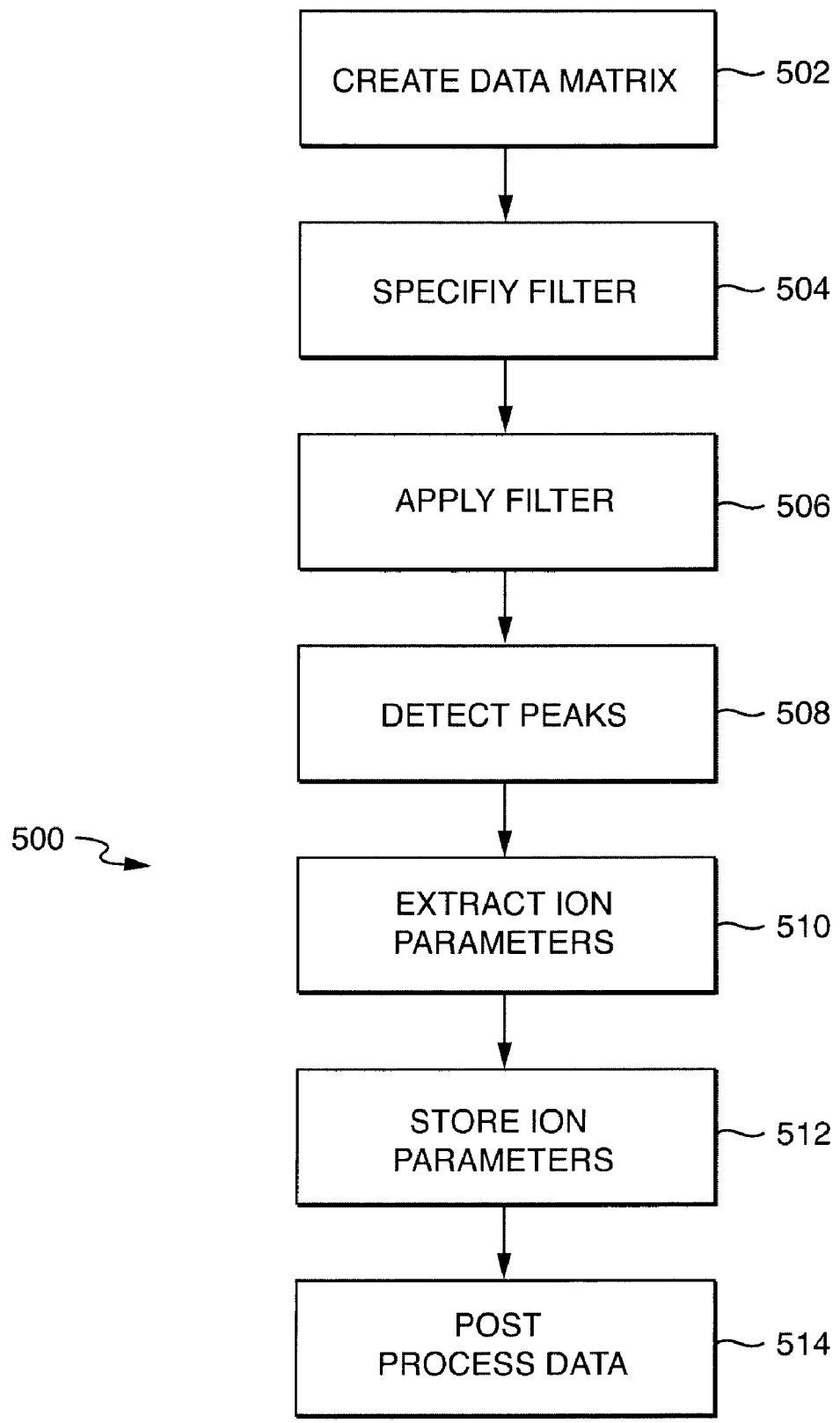
FIG. 5 is a flow chart for a method for processing data according to an embodiment of the present invention.

FIG. 5 is a flow chart 500 for processing experimental analysis output, such as spectra and chromatograms. Flow chart 500 can be embodied in a number of ways including in the DAS described above. In the embodiment of the present invention illustrated in FIG. 5, analysis proceeds as follows:

STEP 502: Create a two-dimensional data matrix having chromatographic and spectral data.

STEP 504: Specify a two-dimensional convolution filter to apply to the data matrix.

STEP 506: Apply the two-dimensional convolution filter to the data matrix. For example, the data matrix can be convolved with the two-dimensional filter.

STEP 508: Detect peaks in the output of the application of the two-dimensional filter to the data matrix. Each detected peak is deemed to correspond to an ion. Thresholding can be used to optimize peak detection.

STEP 510: Extract ion parameters for each detected peak. The parameters include ion characteristics such as retention time, mass-to-charge ratio, intensity, peak width in the spectral direction and/or peak width in the chromatographic direction.

STEP 512: Store the ion parameters associated with extracted ions in a list or table. Storage can be performed as each peak is detected or after a plurality or all of the peaks have been detected.

STEP 514: Use the extracted ion parameters to post-process the data. For example, the ion parameter table can be used to simplify the data. Such simplification can be accomplished, for example, by windowing to reduce spectral or chromatographic complexity. Properties of the molecules can be inferred from the simplified data.

Figure 6:
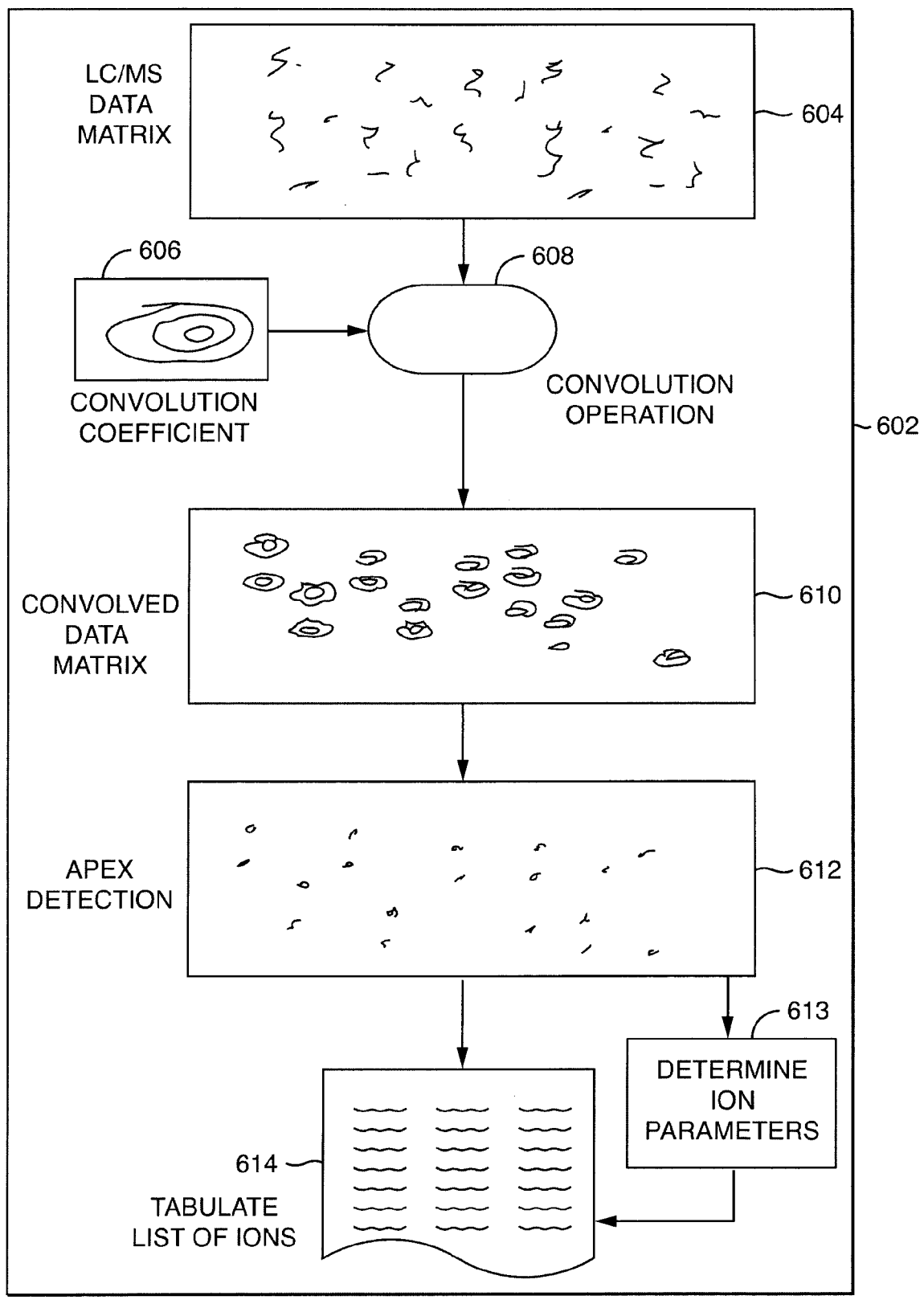
FIG. 6 is a graphical flow chart for a method for processing data according to an embodiment of the present invention.
Figure 7:
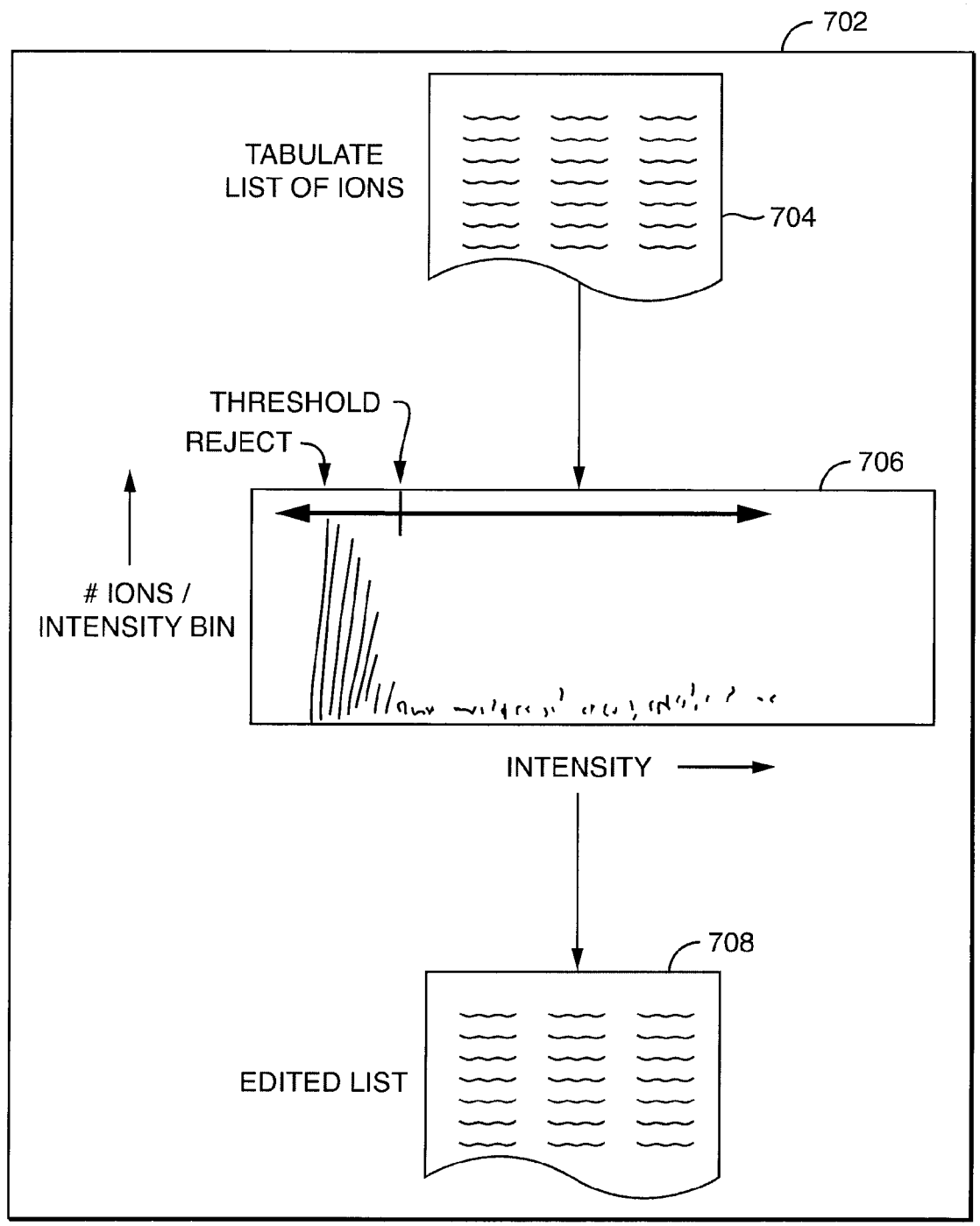
FIG. 7 is a graphical flow chart for a method for determining thresholds for use in detecting ions according to an embodiment of the present invention.

FIGS. 6 and 7 are graphical flow charts describing the foregoing steps of flow chart 500. FIG. 6 is a graphical flowchart 602 of a method for processing LC/MS data according to an embodiment of the present invention. More particularly, each element of graphical flowchart 602 illustrates the result of a step according to an embodiment of the present invention. Element 604 is an exemplary LC/MS data matrix created according to an embodiment of the present invention. As described below, the LC/MS data matrix can be created by placing LC/MS spectra collected at successive times in successive columns of a data matrix. Element 606 is an exemplary two-dimensional convolution filter that can be specified according to desired filtering characteristics. Considerations for specifying the two-dimensional filter are described in more detail below. Element 608 represents application of the two-dimensional filter of element 606 to the LC/MS data matrix of element 604 according to an embodiment of the present invention. An exemplary such application of the two-dimensional filter to the LC/MS data matrix is a two-dimensional convolution wherein the LC/MS data matrix is convolved with the two-dimensional convolution filter. The output of the filtering step is the output data matrix, an example of which is illustrated as element 610. Where the application of the filter to the data matrix comprises a convolution, the output is an output convolved matrix.

Element 612 illustrates an exemplary result of performing peak detection on the output data matrix to identify or detect peaks associated with ions. Thresholding can be used to optimize the peak detection. At this point, the ions are considered detected. Element 614 is an exemplary list or table of the ion properties created using the detected ions.

FIG. 7 is a graphical flowchart 702 illustrating results of determining a detection threshold and its application to further consolidate the ion parameter table according to an embodiment of the present invention. Element 706 represents exemplary peak data accessed from the ion parameter list, Element 704. Element 706 illustrate results of determining a detection threshold using the accessed data. The determined threshold is applied to the ion parameter list generated as Step 704 to generate an edited ion parameter list an example of which is illustrated as Step 708. The foregoing steps are now explained in more detail.

Step 1: Create Data Matrix

Figure 8:
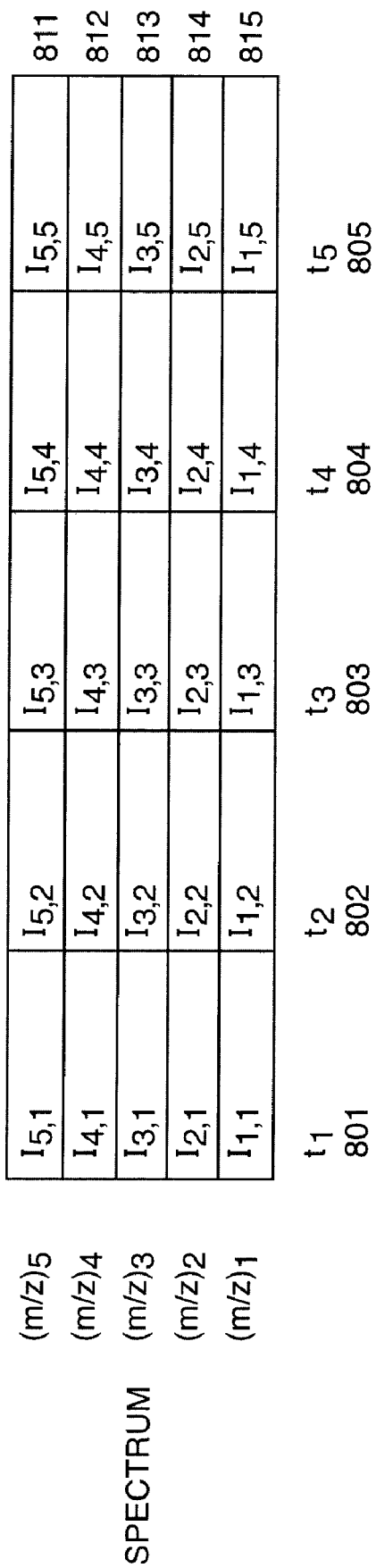
FIG. 8 illustrates an exemplary data matrix according to an embodiment of the present invention.

Rather than view the output of an LC/MS analysis as distinct series of spectra and chromatograms, it is advantageous to configure the LC/MS output as a data matrix of intensities. In an embodiment of the present invention, the data matrix is constructed by placing the data associated with each successive spectrum collected at increasing time in successive columns of a data matrix thereby creating a two-dimensional data matrix of intensities. FIG. 8 illustrates an exemplary such data matrix 800 in which five (5) spectra successively collected in time are stored in successive columns 801-805 of data matrix 800. When the spectra are stored in this manner, the rows of data matrix 800 represent chromatograms at corresponding m/z values in the stored spectra. These chromatograms are indicated by rows 811-815 in data matrix 800. Thus, in matrix form, each column of the data matrix represents a spectrum collected at a particular time, and each row represents a chromatogram collected at a fixed m/z. Each element of the data matrix is an intensity value collected at a particular time (in the corresponding chromatogram) for a particular m/z (in the corresponding spectrum). Although the present disclosure assumes column-oriented spectral data and row-oriented chromatographic data, in alternate embodiments of the present invention, the data matrix is oriented such that rows represent spectra and columns represent chromatograms.

Figure 9:
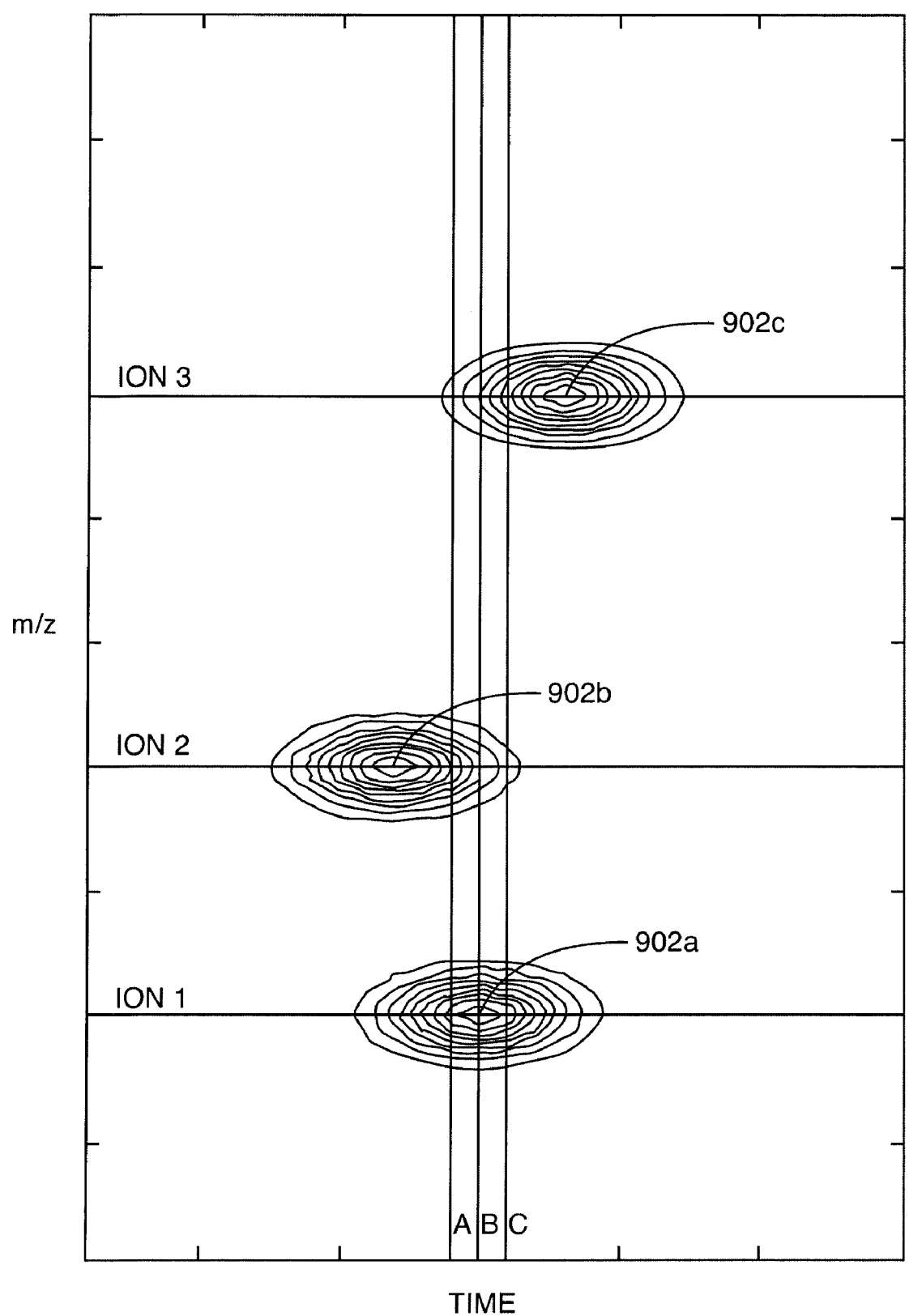
FIG. 9 illustrates a contour plot representation of an exemplary data matrix created from the data of FIGS. 3 and 4 according to an embodiment of the present invention.

FIG. 9 is an exemplary graphical representation (in particular, a contour plot) of a data matrix generated as described above by storing spectral data in successive columns of the data matrix. In the contour plot illustrated in FIG. 9, each of ions 1, 2 and 3 appears as an island of intensity. The contour plot distinctly shows not only the presence of the three ions, but also that the elution order is ion 2, followed by ion 1, followed by ion 3. FIG. 9 also shows three apices 902*a*, 902*b* and 902*c*. Apex 902*a* corresponds to ion 1, apex 902*b* corresponds to ion 2 and apex 902*c* corresponds to ion 3. The locations of apices 902*a*, 902*b*, and 902*c* correspond to the m/z and retention time for ions 1, 2 and 3 respectively. The height of the apex above the zero value floor of the contour plot is a measure of the ion's intensity. The counts or intensities associated with a single ion are contained within an ellipsoidal region or island. The FWHM of this region in the m/z (column) direction is the FWHM of the spectral (mass) peak. The FWHM of this region in the row (time) direction is the FWHM of the chromatographic peak.

The innermost of the concentric contours forming an island identifies the element having the highest intensity. This local maximum or maximal element has an intensity greater than its nearest neighbors. For example, for two-dimensional data contours, a local maximum or apex is any point whose amplitude is greater than its nearest-neighbor elements. In one embodiment of the present invention, a local maximum or apex must be greater than eight (8) nearest neighbor elements. For example in the Table 1, the central element is a local maximum because each of the 8 adjoining elements has a value less than 10.

TABLE 1

Example showing maximum

| 8.5 | 9.2  | 6.8 |
|-----|------|-----|
| 9.2 | 10.0 | 8.4 |
| 7.9 | 8.5  | 7.2 |

There are six lines drawn through the contour plot of FIG. 9. The three horizontal lines, labeled ion 1, ion 2 and ion 3, identify cross sections corresponding to the chromatograms for ions 1, 2 and 3 respectively as illustrated in FIG. 4. The three vertical lines, labeled A, B and C, identify cross sections corresponding to the mass spectra 3A, 3B and 3C respectively as illustrated in FIG. 3.

After the data matrix is created, ions are detected. For each detected ion, ion parameters, such as retention time, m/z and intensity, are obtained. If the data matrix is free of noise and if the ions do not interfere with one another (e.g., by chromatographic co-elution and spectral interference), then each ion produces a unique, isolated island of intensity, as illustrated in the contour plot of FIG. 9.

As shown in FIG. 9, each island contains a single maximal element. Where there is no noise, co-elution or interference, ion detection and parameter quantification according to an embodiment of the present invention proceeds as follows as shown in flow chart 1000 in FIG. 10:

STEP 1001: Form Data Matrix
STEP 1002: Interrogate each element in the data matrix.
STEP 1004: Identify all elements that are local maxima of intensity and have positive values.
STEP 1006: Label each such local maximum as an ion.
STEP 1008: Extract ion parameters.
STEP 1010: Tabulate ion parameters.
STEP 1012: Post-process ion parameters to obtain molecular properties.

In Step 1008, the parameters of each ion are obtained by examining the maximal element. An ion's retention time is the time of the scan containing the maximal element. The ion's m/z is the m/z for the channel containing the maximal element. The ion's intensity is the intensity of the maximal element itself, or alternatively, the intensity can be the sum of intensities of elements surrounding the maximal element. Interpolation techniques, described below, can be used to better estimate these parameters. Secondary observable parameters, including for example, the widths of the peak in the chromatographic and spectral directions, can also be determined.

Steps 2 and 3: Specification and Application of Filter
Need for Filters
Rarely, if ever, is co-elution, interference, or noise absent in LC/MS experiments. The presence of co-elution, interference, or noise can severely reduce the ability to accurately and reliably detect ions. Consequently, the simple detection and quantification procedure illustrated by flow chart 1000 may not be adequate in all circumstances.

Coelution

Figure 11:
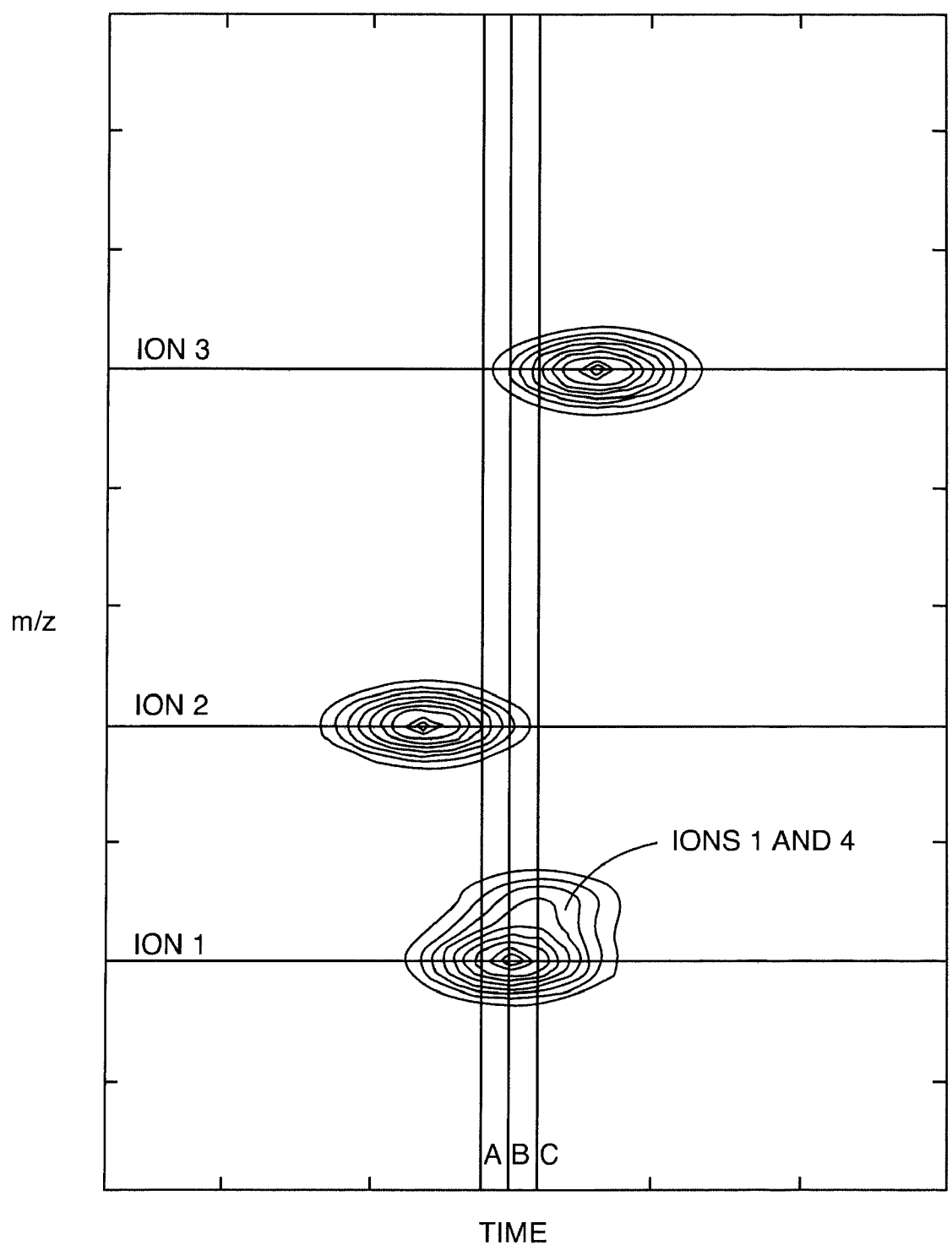
FIG. 11 illustrates an effect of a co-eluting ion on the exemplary data matrix of FIG. 9.

FIG. 11 is an exemplary contour plot showing the effects of co-elution and interference due to finite peak widths. In the example illustrated in FIG. 11, another ion, ion 4, is assumed to have m/z and retention time values somewhat larger than that of ion 1 as well as have an apex in both the spectral and chromatographic directions lying within the FWHM of the apex of ion 1. As a result, ion 4 is co-eluted with ion 1 in the chromatographic direction and interferes with ion 1 in the spectral direction.

Figure 12C:
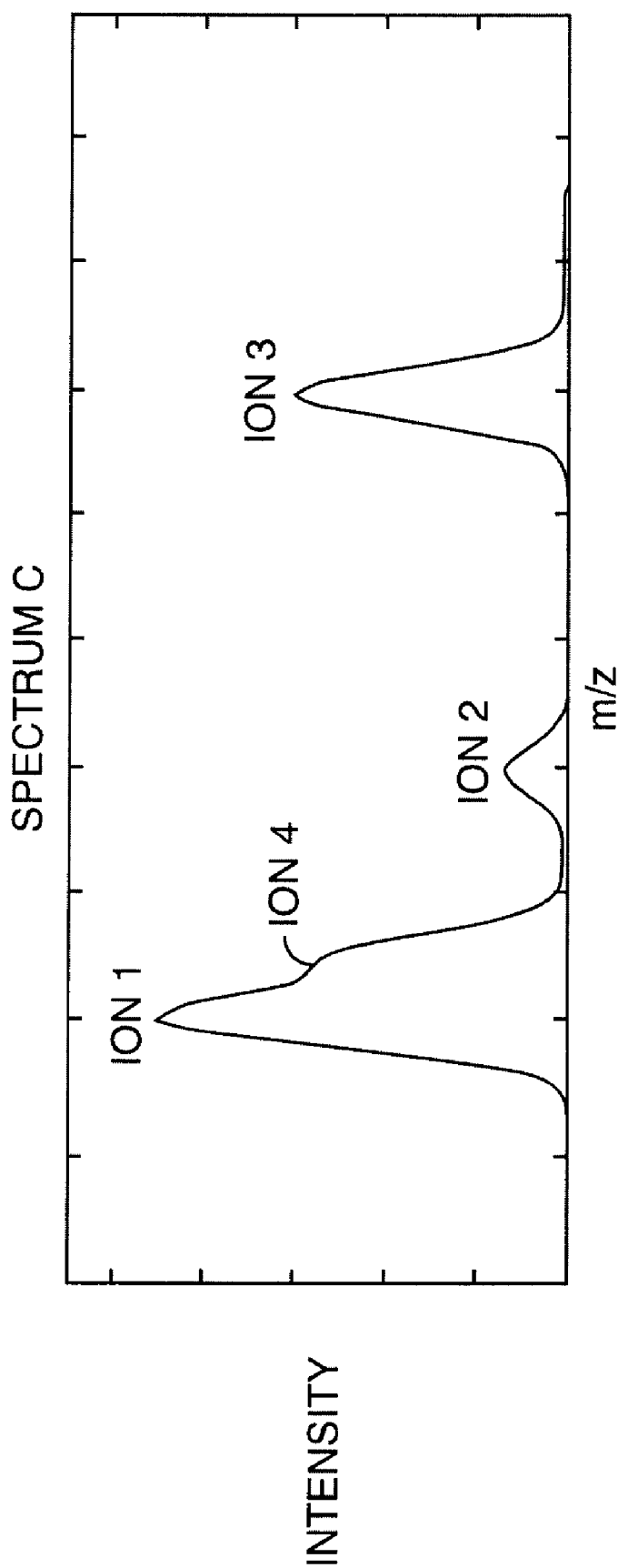
FIG. 12 illustrates a "shoulder" effect of a co-eluting ion on the exemplary data illustrated in FIG. 3.

FIG. 12 illustrates the spectral effects due to co-elution of ion 4 at the times indicated by lines A, B, and C of FIG. 11. In each spectrum shown in FIG. 12, ion 4 appears as a shoulder to ion 1. This is also apparent from the contour plot shown in FIG. 11 because there is no distinct apex associated with ion 4.

Thus one problem with detection in LC/MS systems is that pairs of ions may co-elute in time and interfere spectrally such that the pair of ions produces only a single local maximum, not two. Co-elution or interference can cause true ions, having significant intensity in the data matrix, to be missed, i.e., not detected. Such missed detection of a true peak as an ion is referred to as a false negative.

Noise

Noise encountered in LC/MS systems typically falls into two categories: detection noise and chemical noise. Detector and chemical noise combine to establish a baseline noise background against which the detection and quantitation of ions is made.

Detection noise, also known as shot or thermal noise, is inherent in all detection processes. For example, counting detectors, such as MCPs, add shot noise, and amplifiers, such as electrometers, add thermal or Johnson noise. The statistics of shot noise are generally described by Poisson statistics. The statistics of Johnson noise are generally described by Gaussian statistics. Such detection noise is inherent in the system and cannot be eliminated.

The second kind of noise encountered in LC/MS systems is chemical noise. Chemical noise arises from several sources. For example, small molecules that are inadvertently caught up in the process of separation and ionization can give rise to chemical noise. Such molecules can be a constant presence, each producing an essentially constant background intensity at a given mass-to-charge ratio, or each such molecule can be separated thereby producing a chromatographic profile at a characteristic retention time. Another source of chemical noise is found in complex samples, which can contain both molecules whose concentrations vary over a wide dynamic range and interfering elements whose effects are more significant at lower concentrations.

Figure 13:
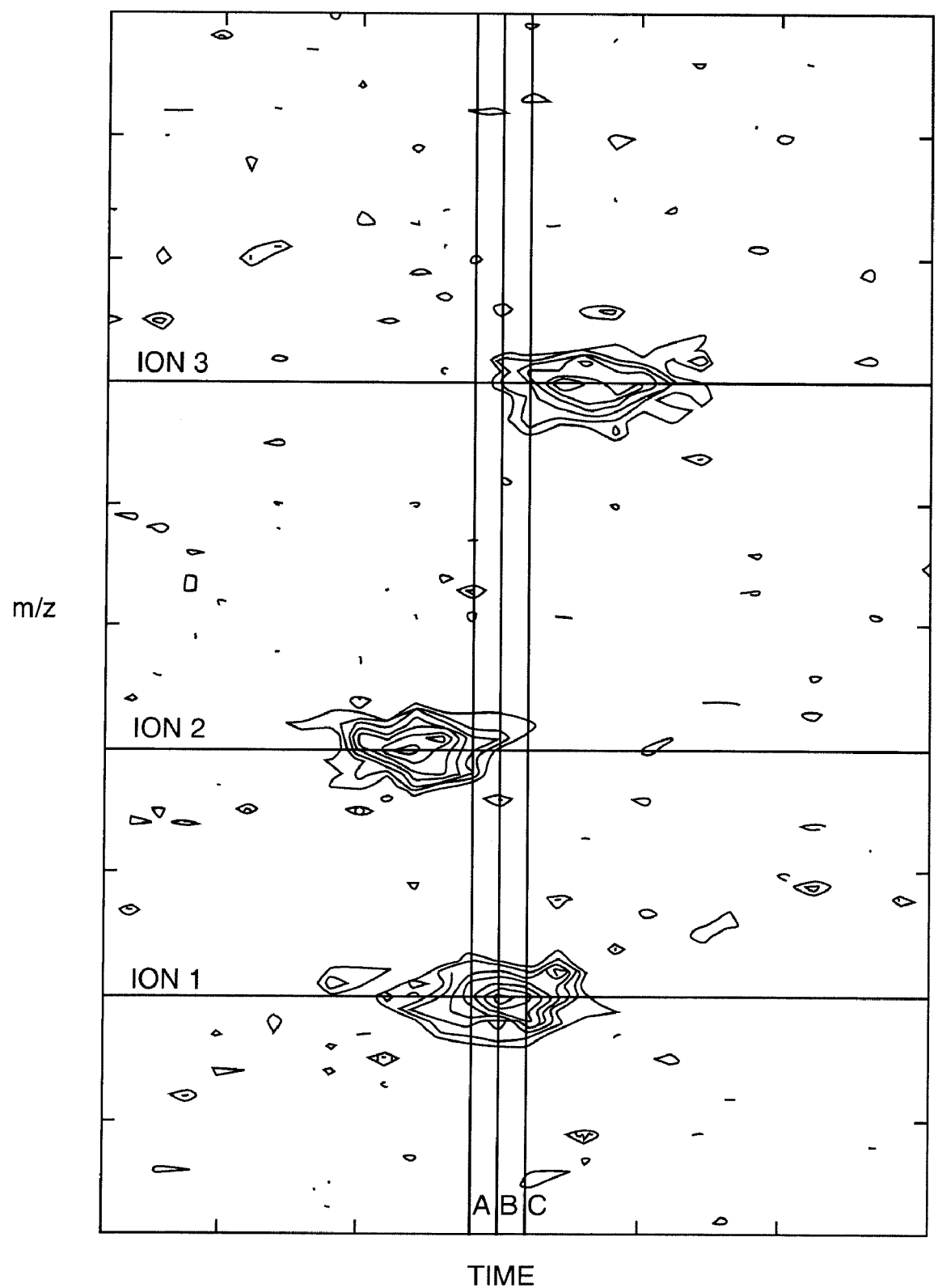
FIG. 13 illustrates how noise affects exemplary data in a data matrix created according to embodiments of the present invention.
Figure 14A:
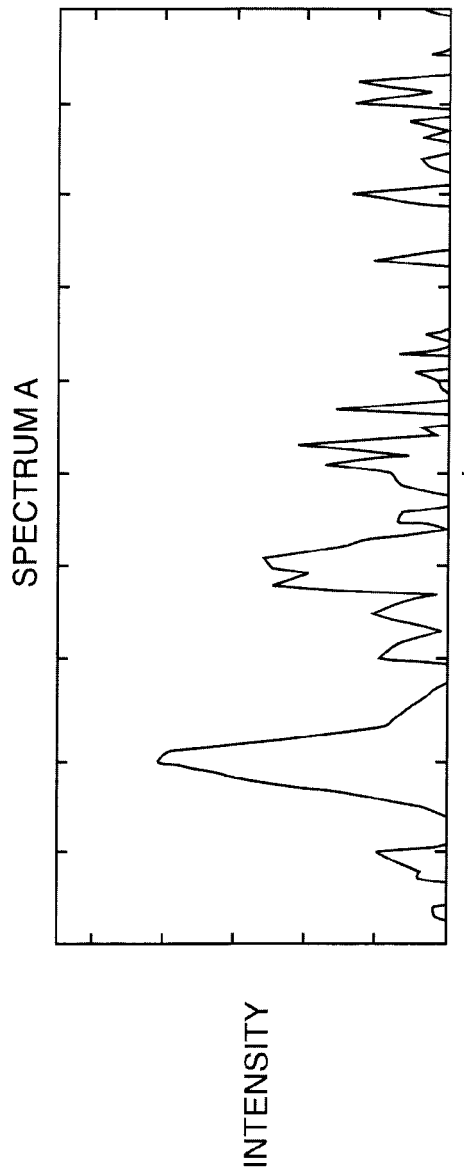
FIG. 14A illustrates spectra for three ions corresponding to the exemplary data illustrated in the data matrix shown in FIG. 13.
Figure 14B:
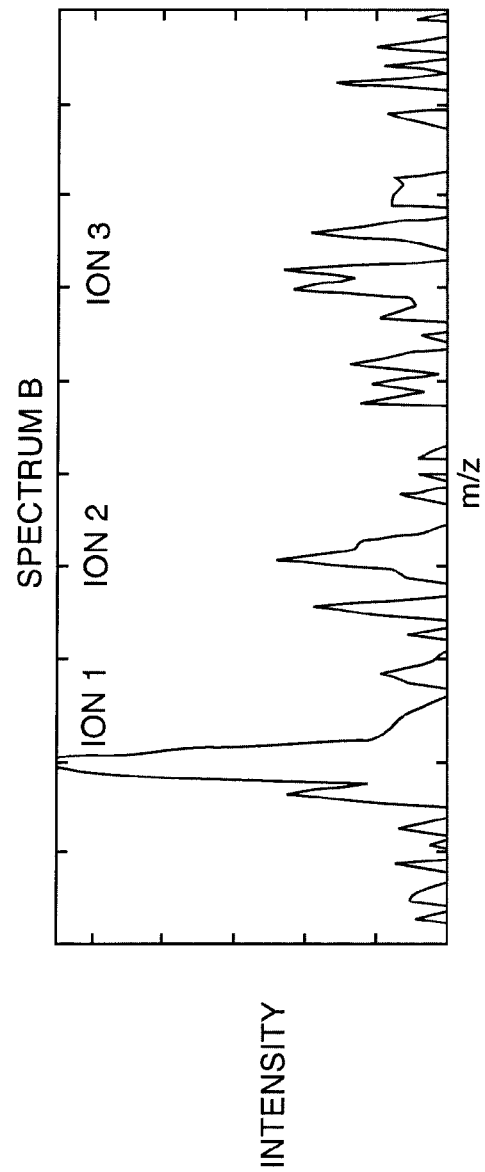
FIG. 14B illustrates chromatograms for three ions corresponding to the exemplary data illustrated in the data matrix shown in FIG. 13.
Figure 14C:
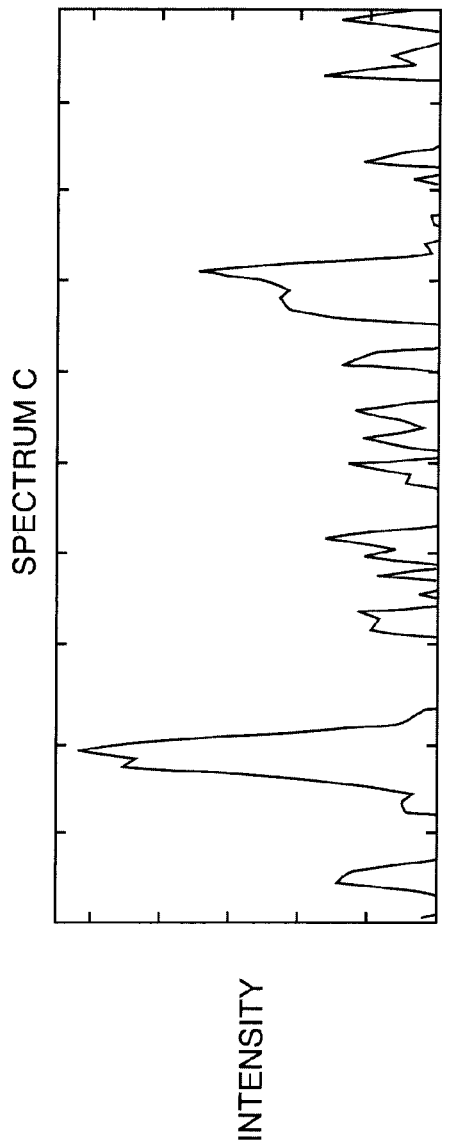
Figure 14D:
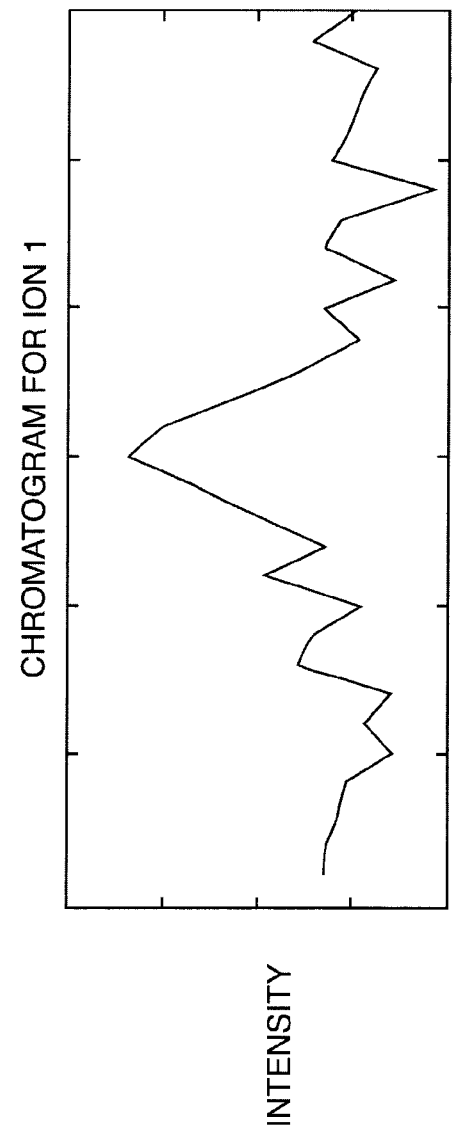
Figure 14E:
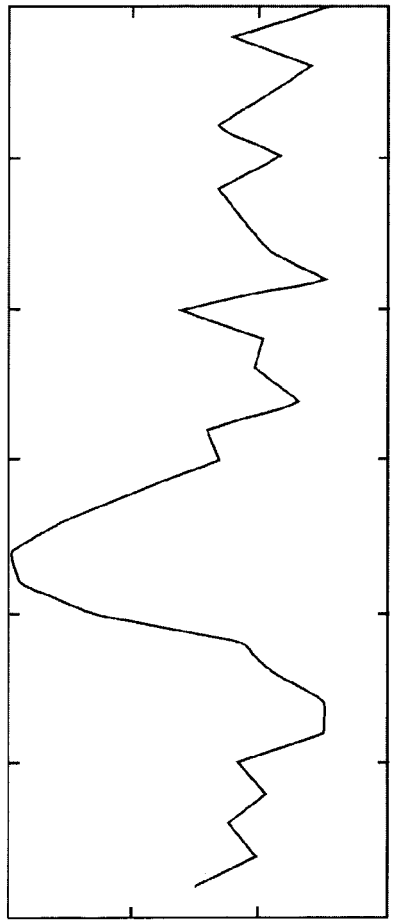
Figure 14F:
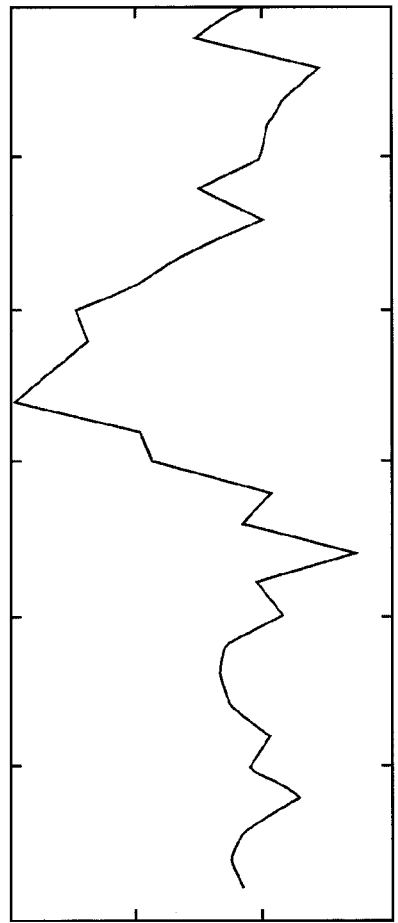

FIG. 13 is an exemplary contour plot illustrating the effects of noise. In FIG. 13, numerically generated noise is added to an ion peak contour plot to simulate the effects of chemical and detector noise. FIG. 14A illustrates mass spectra (Spectra A, B and C) corresponding to lines A, B and C respectively in FIG. 13, FIG. 14B illustrates chromatograms for ions 1, 2, 3 corresponding to lines labeled ion 1, ion 2 and ion 3 respectively in FIG. 13. As can be seen in FIG. 13, one detrimental effect of the additive noise is that it causes apices to appear throughout the plot, including within the FWHM of the nominal apex locations associated with ions 1 and 2. These noiseinduced apices can be erroneously identified as peaks corresponding to ions, thereby resulting in false positive ion detections.

Thus, local maxima may be due to the noise rather than ions. As a result, false peaks, i.e., peaks not associated with an ion, may be counted as an ion. Moreover, noise might produce more than one multiple local maximum for an ion. These multiple maxima could result in detection of peaks that do not represent true ions. Thus, peaks from a single ion could be multiply counted as separate ions when in fact the multiple peaks are due only to a single ion. Such detection of false peaks as ions is referred to as false positives.

Figure 10:
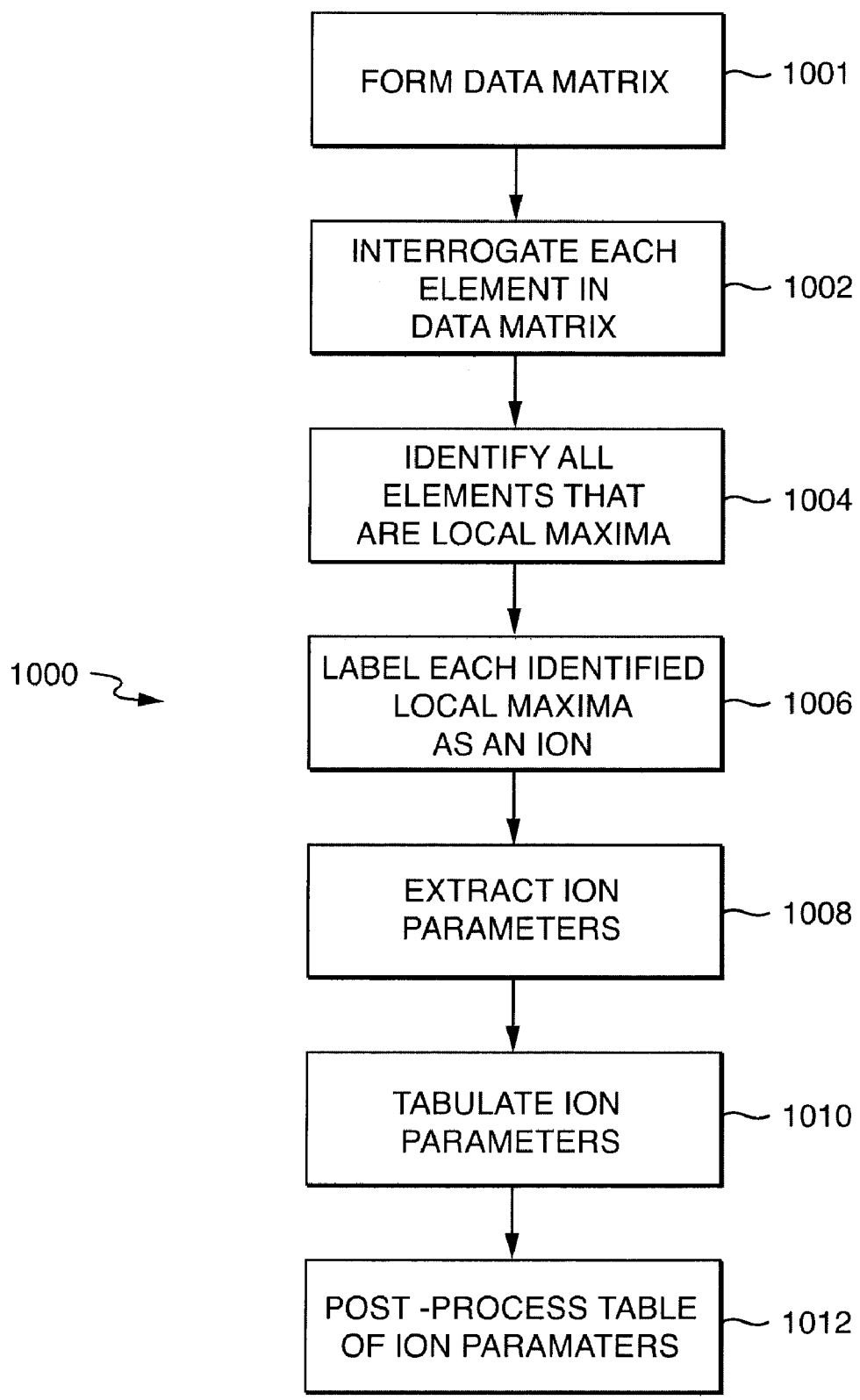
FIG. 10 is a flow chart for a simplified method of processing data in the absence of noise according to an embodiment of the present invention.

In addition to disregarding noise effects, the simple ion detection algorithm described in FIG. 10 is generally not statistically optimal. This is because the variance in the estimates of retention time, m/z and intensity are determined by the noise properties of a single maximal element. The simplified algorithm does not make use of the other elements in the island of intensities surrounding the maximal element. As described in more detail below, such neighboring elements can be used to reduce variance in the estimate.

Role of Convolution

According to embodiments of the present invention, the LC/MS data matrix is a two-dimensional array. Such a data matrix can be processed by convolving it with a two-dimensional array of filter coefficients.

The convolution operation employed in embodiments of the present invention provides a more general and powerful approach to peak detection than the simple signal-averaging schemes employed in conventional systems. The convolution operation employed in embodiments of the present invention addresses the limitations of the method described in FIG. 10.

The filter coefficients can be chosen to provide estimates of ion parameters that have better signal-to-noise ratios than those obtained from analyzing single channels or scans.

The convolution filter coefficients can be chosen to produce estimates of ion parameters that have the greatest precision or least statistical variance for a particular data set. These benefits of embodiments of the present invention provide more reproducible results for ions at low concentration than do conventional systems.

Another advantage of embodiments of the present invention is that filter coefficients can be chosen to resolve ions that are co-eluted and interfering. For example, the apices of ions appearing as shoulders to other ions in a mass spectrum can be detected using appropriately specified filter co-efficients in embodiments of the present invention. Such detection overcomes limitations associated with conventional techniques in analyzing complex chromatograms, where co-elution and ion-interference are a common problem.

Another advantage of embodiments of the present invention is that filter coefficients can be chosen to subtract baseline signals, producing more accurate estimates of ion intensity.

Another advantage of embodiments of the present invention is that filter coefficients can be chosen to minimize the computation burden of convolution, resulting in high-speed operation of peak detection and the estimation of ion parameters.

In general, numerous filter shapes can be used in the convolution, including, for example, Savitzky-Golay (SG) smoothing and differentiating filters. The filter shapes can be chosen to perform a number functions including smoothing, peak identification, noise reduction and baseline reduction. Filter shapes used in preferred embodiments of the present invention are described below Implementation of Convolution in this Invention The convolution operation according to embodiments of the present invention is linear, non-iterative and not dependent on the values of the data in the data matrix. In an embodiment of the present invention, the convolution operation is implemented by means of a general purpose programming language using a general purpose computer such as computer 118. In an alternate embodiment of the present invention, the convolution operation is implemented in a special purpose processor known as digital-signal-processor (DSP). Typically, DSP-based filtering provides enhanced processing speed over general purpose computer-based filtering.

In general, convolution combines two inputs to produce one output. Embodiments of the present invention employ a two-dimensional convolution. One input to the two-dimensional convolution operation is the data matrix of intensities created from the spectral output of an LC/MS experiment. The second input to the two-dimensional convolution operation is a matrix of filter coefficients. The convolution operation outputs an output convolved matrix. Generally, the output convolved matrix has the same number of rows and column elements as the input LC/MS matrix.

For simplicity in the present description, assume that the LC/MS data matrix is rectangular and that the size of the matrix of filter coefficients is comparable to the size of a peak. In this case the size of the filter coefficient matrix is smaller than the size of the input data matrix or output convolved matrix.

An element of the output matrix is obtained from the input LC/MS data matrix as follows: the filter matrix is centered on an element in the input data matrix, and then the input data matrix elements are multiplied by the corresponding filter matrix elements and the products are summed, producing an element of the output convolved data matrix. By combining neighboring elements, convolution filters reduce variance in the estimates of an ion's retention time, mass-to-charge ratio, and intensity.

The edge-values of the output convolved matrix are those elements that are within half the filter width from the edge of the output convolved matrix. Generally these elements can be set to an invalid value in embodiments of the present invention to indicate invalid filtering values. Generally, ignoring these edge values is not a significant limitation for embodiments of the present invention and these invalid values can be ignored in subsequent processing.

One-Dimensional Convolution

Convolution for a one-dimensional case is clearly described in detail. This description is followed by generalizing convolution to the two-dimensional case. It is useful to first describe the one-dimensional case because the two-dimensional convolution operation that is used in the preferred embodiment of the present invention is implemented by applying a series of one-dimensional convolutions to the data matrix.

In one dimension, the convolution operation is defined as follows. Given a one-dimensional, N-element, input array of intensities $d_i$ and a one-dimensional, M-element, array of convolution filter coefficients $f_j$, the convolution operation is defined as:

$$c_i = \sum_{j=-h}^{h} f_j d_{i-j} \quad (1)$$

where $c_i$ is the output convolved array, and i=1, . . . , N. For convenience, M is chosen to be an odd number. The index j varies from j=−h, . . . , 0, . . . , h, where h is defined ash h≡(M−1)/2.

Thus, the value of $c_i$ corresponds to a weighted sum of the h elements surrounding $d_i$. Spectra and chromatograms are examples of one-dimensional input arrays that contain peaks. The width of the convolution filter $f_j$ is set to be approximately the width of a peak. Thus, M is on the order of the number of array elements that span the width of a peak. Peaks have a width which typically is much smaller than the length N of the input array, so that in general M☐N.

Although the index i for $d_i$ ranges from 1 to N, in some embodiments of the present invention, $c_i$ is defined only for i>h or i≦(N−h) to account for edge effects. The value for $c_i$ near the array boundaries, i.e. when i≦h or i>(N−h), is not defined for the summation. Such edge effects can be handled by limiting the values for $c_i$ to be i>h or i≦(N−h), where the summation is defined. In this case, the summation applies only to those peaks far enough away from the array edges so that the filter $f_j$ can be applied to all points within the neighborhood of the peak. That is, filtering is not performed at the edges of the data array $d_i$. Generally, ignoring edge effects is no a significant limitation for embodiments of the present invention.

If filtered values are needed near the edge for 1<i<h or N≧i>(N−h), either the data array and/or the filter coefficients can be modified for these edge elements. The data matrix can be modified by append h elements to each end the array, and apply the M coefficient filter to an array that contains N+2h elements.

Alternatively, edge effects can be considered by appropriately modifying the limits of the filtering function to account for there being less than M points for filtering near the edges.

Two-Dimensional Convolution

The one-dimensional convolution operation described above can be generalized to the case of two-dimensional data for use in embodiments of the present invention. In the two-dimensional case, one input to the convolution operation is a data matrix $d_{i,j}$ subscripted by two indices, (i,j), wherein i=1, . . . , M and j=1, . . . , N. The data values of the input data matrix can vary from experiment to experiment. The other input to the convolution is a set of fixed filter coefficients, $f_{p,q}$, that is also subscripted by two indices. The filter coefficients matrix, $f_{p,q}$, is a matrix that has P×Q coefficients. Variables h and l are defined as h≡(P−1)/2 and l≡(Q−1)/2. Thus, p=−h, . . . , h, and q=−l, . . . , l.

Convolving $d_{i,j}$ with $f_{p,q}$ yields the output convolved matrix $c_{i,j}$:

$$c_{i,j} = \sum_{p=-h}^{h} \sum_{q=-l}^{l} f_{p,q} d_{i-p,j-q}. \qquad (2)$$

Generally, the size of the filter is much less than the size of the data matrix, so that P<<M and Q<<N. The above equation indicates that $c_{i,j}$ is computed by centering $f_{p,q}$ on the (i,j) th element of $d_{i,j}$ and then using the filter coefficients $f_{p,q}$ to obtain the weighed sum of the surrounding intensities. Thus, each element of the output matrix $c_{i,j}$ corresponds to a weighted sum of the elements of $d_{i,j}$, wherein each element $d_{i,j}$ is obtained from a region centered on the $_{i,j}$th element.

Although the index i and j for $d_{i,j}$ ranges from i=1 to N, and j from 1 to M, in some embodiments of the present invention, $c_{i,j}$ is defined only for i≧h or i≦(N−h) and j≧l or j≦(M−l) to account for edge effects. The value for $c_i$ near the array boundaries, i.e. when i<h or i>(N−h) and/or j≦l or j≦(M−l) is not defined for the summation. Such edge effects can be handled by limiting the values for $c_{i,j}$ to be those where the summation is defined. In this case, the summation applies only to those peaks far enough away from the array edges so that the filter $f_{p,q}$ can be applied to all points within the neighborhood of the peak. That is, filtering is not performed at the edges of the data array $d_{i,j}$. Generally, ignoring edge effects is no a significant limitation for embodiments of the present invention.

If filtered values are needed near the edge for 1≦i<h and N≧i>(N−h), either the data matrix and/or the filter coefficients matrix can be modified for these edge elements. One approach is to append h elements to the end of each row, and/or elements to the end of each column. The two-dimensional convolution filter is then applied to a data matrix that contains (N+2h)×(M+2l) elements.

Alternatively, edge effects can be considered by appropriately modifying the limits of the filtering function to account for there being less than P points for filtering near the row edges and Q points for filtering near the column edges.

The computational burden for implementation of equation (2) can be determined as follows. If $f_{p,q}$ contains P×Q coefficients then the number of multiplications needed to compute a value for $c_{i,j}$ is P×Q. For example, where P=20 and Q=20, it follows that 400 multiplications are needed to determine each output point $c_{i,j}$ in the output convolved matrix. This is a high computation burden that can be eased by other approaches to two-dimensional convolution.

Two-Dimensional Convolution with Rank-1 Filters

The two-dimensional convolution filter described in equation (2) applies a filter matrix that contains P×Q independently specified coefficients. There are other ways for specifying the filter coefficients. Although the resulting convolution coefficients are not as freely specified, the computation burden is eased.

One such alternate way of specifying the filter coefficients is as a rank-1 filter. To describe a rank-1 convolution filter, consider that a two-dimensional convolution of the LC/MS data matrix can be accomplished by the successive application of two one-dimensional convolutions. See for example, in JOHN H. KARL, INTRODUCTION TO DIGITAL SIGNAL PROCESSING, PG. 320 (ACADEMIC PRESS 1989) ("KARL"), which is hereby incorporated by reference herein. For example, a one-dimensional filter, $g_q$, is applied to each row of the LC/MS data matrix, producing an intermediate convolved matrix. To this intermediate convolved matrix, a second one-dimensional filter, $f_p$, is applied to each column. Each one-dimensional filter can be specified with a different set of filter coefficients. Equation (3) illustrates how the filters comprising a rank-1 convolution filter are applied in succession, wherein the intermediate matrix is enclosed in the parentheses.

$$c_{i,j} = \sum_{p=-h}^{h} f_p \left( \sum_{q=-l}^{l} g_q d_{i-p,j-q} \right) \qquad (3)$$

$$= \sum_{p=-h}^{h} \sum_{q=-l}^{l} f_p g_q d_{i-p,j-q}. \qquad (4)$$

The computational burden for implementation of equation (3) can be determined as follows. If $f_p$ contains P coefficients and $g_q$ contains Q coefficients, then the number of multiplications needed to compute a value for $c_{i,j}$ is P+Q. For example, where P=20 and Q=20, only 40 multiplications are needed to determine each output point $c_{i,j}$ in the output convolved matrix. As can be seen, this is more computationally efficient than the general case of two-dimensional convolution described in Eq. (2) where 20×20=400 are required to determine each $c_{i,j}$.

Equation (4) is a rearrangement of equation (3) that illustrates that the successive operations are equivalent to a convolution of the data matrix with a single coefficient matrix whose elements are pair-wise products of the one dimensional filters. An examination of equation (4) shows that in using the rank-1 formulation, the effective two-dimensional convolution matrix is a rank-1 matrix formed by the outer product of two one-dimensional vectors. Thus, equation (4) can be rewritten as:

$$c_{i,j} = \sum_{p=-h}^{h} \sum_{q=-l}^{l} F_{pq} d_{i-p,j-q} \quad (5)$$

$$F_{pq} \equiv f_p g_q. \quad (6)$$

The two-dimensional coefficient matrix $F_{pq}$ emerges from the convolution operation. $F_{pq}$ has the form of a rank-1 matrix, where a rank-1 matrix is defined as the outer product of a column vector (here, $f_p$) and a row vector (here, $g_q$). See for example, in GILBERT STRANG, INTRODUCTION TO APPLIED MATHEMATICS, 68FF (WELLESLEY-CAMBRIDGE PRESS 1986) ("STRANG"), which is hereby incorporated by reference herein.

In embodiments of the present invention using a rank-1 filter implementation, the rank-1 filter is characterized by two orthogonal cross sections, one for each filter. The filter for each orthogonal cross-section is specified by a one-dimensional filter array.

Two-Dimensional Convolution with Rank-2 Filters

A two-dimensional convolution operation can be carried out with a rank-2 filter. Two-dimensional convolution with a rank-2 filter is carried out by computing two rank-1 filters and summing their result. Thus, four filters: $f_p^1$, $g_q^1$, $f_p^2$, and $g_q^2$ are required to implement a rank-2 filter for the two-dimensional convolution performed in embodiments of the present invention.

Two of the filters $f_p^1$ and $g_q^1$ are associated with the first rank-1 filter and two of the filters $f_p^2$ and $g_q^2$ are associated with the second rank-1 filter. These four filters $f_p^1, f_p^2$ and $g_q^1, g_q^2$ are implemented as follows:

$$c_{i,j} = \sum_{p=-h}^{h} f_p^1 \left( \sum_{q=-l}^{l} g_q^2 d_{i-p,j-q} \right) + \sum_{p=-h}^{h} f_p^2 \left( \sum_{q=-l}^{l} g_q^2 d_{i-p,j-q} \right) \quad (7)$$

$$= \sum_{p=-h}^{h} \sum_{q=-l}^{l} (f_p^1 g_q^1 + f_p^2 g_q^2) d_{i-p,j-q} \quad (8)$$

Filters $f_p^1$ and $f_p^2$ are applied in the spectral direction (along the columns) and filters $g_q^1$ and $g_q^2$ are applied in the chromatographic direction (along the rows). Equation (7) illustrates how each filter pair can be applied in succession, where the intermediate matrix is enclosed in the braces, and how the results from the two rank-1 filters are summed. Equation (7) shows the preferred manner of implementing the rank-2 filter according to embodiments of the present invention.

Equation (8) is a rearrangement of equation (7) to show that the successive operations in the rank-2 filter configuration are equivalent to a convolution of the data matrix with a single coefficient matrix whose elements are the sum of pair-wise products of the two one-dimensional filter pairs.

To analyze the computational requirements of a rank-2 filter, consider that if $f_p^1$ and $f_p^2$ both contain P coefficients and $g_q^1$ and $g_q^2$ both contain Q coefficients, then the number of multiplications needed to compute a value for an element of the output convolution matrix $c_{i,j}$ is 2(P+Q). Thus, in the case where P=20 and Q=20, only 80 multiplications are needed to compute each element of the output convolution matrix, whereas in the general case as shown in equation (2), 20×20=400 are required to compute each $c_{i,j}$.

Thus, an embodiment of the present invention employing a rank-2 filter, the effective two-dimensional convolution matrix is formed from the sum of the outer product of two pairs of one-dimensional vectors. Equation (8) can be rewritten as $$c_{i,j} = \sum_{p=-h}^{h} \sum_{q=-l}^{l} F_{pq} d_{i-p,j-q} \quad (9)$$

$$F_{pq} \equiv f_p^1 g_q^1 + f_p^2 g_q^2. \quad (10)$$

Two-dimensional coefficient matrix $F_{pq}$ emerges from the convolution operation. The two-dimensional coefficient matrix $F_{pq}$ has the form of a rank-2 matrix, where a rank-2 matrix is defined as the sum of two linearly independent rank-1 matrices as described in STRANG. Here $f_p^1 g_q^1$ and $f_p^2 g_q^2$ are each rank-1 matrices.

Filter Specifications

Equations (2), (3), and (7) are all embodiments of two-dimensional convolution filters of the present invention. Equation (2) specifies the filter coefficients as a matrix $f_{p,q}$, equation (3) specifies the filter coefficients as a set of two one-dimensional filters, $f_p$ and $g_q$, and equation (7) specifies the filters as a set of four one-dimensional filters, $f_p^1$, $g_q^1$ and $f_p^2$, $g_q^2$.

Equations (2), (3), and (7) do not specify the preferred values of these coefficients. The values of the filter coefficients for the present invention are chosen to address the limitations of the method of FIG. 10. The filter coefficients are chosen to accomplish several goals which include the reduction of the effects of detector and chemical noise, the partial resolution of coeluted and interfered peaks, the subtraction of baseline noise, and achievement of computational efficiency and high-speed operation.

The Matched Filter Theorem (MFT) is a prescriptive method, known in the prior art, to obtain filter coefficients than can be implemented using Equation (2). See for example, KARL at 217; BRIAN D. O. ANDERSON & JOHN B. MOORE, OPTIMAL FILTERING 223ff (PRENTICE-HALL INC. 1979) ("ANDERSON") at 223ff which is hereby incorporated by referral herein. Filters obtained from the MFT are designed to detect the presence of signals and to reduce the effects of detector noise. Such filters can then be used to detect ions in the LC/MS data matrix and can be used to determine the retention time, mass-to-charge ratio, and intensity of ions. A filter obtained from the MFT is an improvement over the method of FIG. 10. In particular such filters reduce variance and improve precision by combining data from elements within a peak that neighbor the peak apex. However, such filters are not designed to subtract baseline noise or to resolve coeluted and interfered peaks. Filters obtained from the MFT and are not designed to achieve high speed operation.

The MFT and a set of filter coefficients that can be obtained from it represent an improvement over the method of FIG. 10 are described, then modified filters that subtract baselines, reduce the effects of coelution and interference, while still reducing the effect of detector and chemical noise are described. Such filters employ a combination of smoothing and second-derivative filters and are implemented using Equations (3) and (7). The preferred embodiment uses equation (7) with a combination of smoothing and second-derivative filters that together reduce noise, resolve interfering peaks, subtract baselines, and reduce the computational burden to allow for high-speed operation.

Matched Filter Theorem for One-Dimensional Convolution

The MFT is first described for one-dimensional convolution. It is then generalized to two-dimensional convolution.

Coefficients for $f_j$ are chosen to perform a detection function. For example, the matched filter theorem (MFT) provides a set of filter coefficients known as a matched filter that can be used to perform the detection function.

The MFT assumes that the data array $d_i$ can be modeled as a sum of a signal $r_o s_i$ plus additive noise, $n_i$:

$$d_i = r_o s_{i-i_o} + n_i.$$

The shape of the signal is fixed and described by a set of coefficients, $s_i$. The scale factor $r_o$ determines the signal amplitude. The MFT also assumes that the signal is bounded. That is, the signal is zero (or small enough to be ignored) outside some region. The signal is assumed to extend over M elements. For convenience, M is typically chosen to be odd and the center of the signal is located at $s_o$. If h is defined as $h \equiv (M-1)/2$, then $s_i = 0$ for $i < -h$ and for $i > h$. In the above expression, the center of the signal appears at $i = i_o$.

For purposes of simplifying the present description the noise elements $n_i$ are assumed to be uncorrelated Gaussian deviates, with zero mean and a standard deviation of $\sigma_o$. More general formulations for the MFT accommodate correlated or colored noise. See example, ANDERSON at 288-304.

Under these assumptions, the signal-to-noise ratio (SNR) of each element is $r_o s_i / \sigma_o$. The SNR of a weighted sum of the data that contains the signal $s_i$ can be determined by considering an M-element set of weights $w_i$, centered to coincide with the signal where $h \equiv (M-1)/2$, and $i = -h, \ldots, 0, \ldots, h$. Assuming the weights are centered to coincide with the signal, the weighted sum S is defined as:

$$S = \sum_{i=-h}^{h} w_i d_{i-i_0} = r_0 \sum_{i=-h}^{h} w_i s_i + \sum_{i=-h}^{h} w_i n_{i-i_0}.$$

The mean value of the noise term in an ensemble average is zero. Consequently, the average value of S over an ensemble of arrays, where the signal in each array is the same, but the noise is different is:

$$\langle S \rangle = r_0 \sum_{i=-h}^{h} w_i s_i.$$

To determine the noise contribution, the weights are applied to a region containing only noise. The ensemble mean of the sum is zero. The standard deviation of the weighted sum about the ensemble mean is:

$$\sigma \equiv \sqrt{\langle (S - \langle S \rangle)^2 \rangle} = \sigma_0 \sqrt{\sum_{i=-h}^{h} w_i^2}.$$

Finally, the SNR is determined as:

$$\frac{\langle S \rangle}{\sigma} = \frac{r_0}{\sigma_0} \frac{\left(\sum_{i=-h}^{h} w_i s_i\right)}{\sqrt{\sum_{i=-h}^{h} w_i^2}}.$$

This result is for a general set of weighting coefficients $w_i$.

The MFT specifies values for $w_i$ that maximize the SNR. If the weighting factors $w_i$ are regarded as elements of an M dimensional vector w of unit length, i.e., the weighting factors are normalized so that $$\sqrt{\sum_{i=-h}^{h} w_i^2} = 1,$$

then the SNR is maximized when the vector w points in the same direction as the vector s. The vectors point in the same direction when respective elements are proportional to each other i.e., when $w_i \propto s_i$. Consequently, the MFT implies that the weighted sum has the highest signal-to-noise when the weighting function is the shape of the signal itself.

If $w_i$ is chosen such that $w_i = s_i$, then for noise with unit standard deviation, the SNR reduces to:

$$\frac{\langle S \rangle}{\sigma} = \frac{r_0}{\sigma_0} \frac{\left(\sum_{i=-h}^{h} s_i^2\right)}{\sqrt{\sum_{i=-h}^{h} s_i^2}} = \frac{r_0}{\sigma_0} \sqrt{\sum_{i=-h}^{h} s_i^2}.$$

This formulation of SNR corresponds to the signal properties of the weighted sum when the filter coefficients are centered on the signal and the noise properties when the filter is in a noise-only region.

Matched Filter Theorem for Two-Dimensional Convolution

The MFT discussed above for the one-dimensional case can also be generalized to the two-dimensional case for a bounded, two-dimensional signal embedded in a two-dimensional array of data. As before, the data is assumed to be modeled as a sum of signal plus noise:

$$d_{i,j} = r_o s_{i-i_o, j-j_o} + n_{i,j},$$

wherein the signal $S_{i,j}$ is limited in extent and whose center is located at $(i_o, j_o)$ with amplitude $r_o$. Each noise element $n_{i,j}$ is an independent Gaussian deviate of zero mean and standard deviation $\sigma_o$.

To determine the SNR of a weighted sum of the data that contains the signal $S_{i,j}$ consider a P×Q-element set of weights $w_{i,j}$, wherein $h = (P-1)/2$ and $l = (Q-1)/2$, such that $i = -h, \ldots, h$, and $j = -l, \ldots, l$. The weights are centered to coincide with the signal. The weighted sum S is:

$$S = \sum_{i=-h}^{h}\sum_{j=-l}^{l} w_{i,j} d_{i-i_0, j-j_0} = r_0 \sum_{i=-h}^{h}\sum_{j=-l}^{l} w_{i,j} s_{i,j} + \sum_{i=-h}^{h}\sum_{j=-l}^{l} w_{i,j} n_{i-i_0, j-j_0}.$$

The average value of S over the ensemble is:

$$\langle S \rangle = r_0 \sum_{i=-h}^{h}\sum_{j=-l}^{l} w_{i,j} s_{i,j}.$$

The standard deviation of the noise is:

$$\sigma = \sigma_0 \sqrt{\sum_{i=-h}^{h}\sum_{j=-l}^{l} w_{i,j}^2}.$$

and the signal-to-noise ratio is:

$$\frac{\langle S \rangle}{\sigma} = \frac{r_o}{\sigma_o} \frac{\sum_{i=-h}^{h}\sum_{j=-l}^{l} w_{i,j} s_{i,j}}{\sqrt{\sum_{i=-h}^{h}\sum_{j=-l}^{l} w_{i,j}^2}}$$

As in the one-dimensional case described above, the SNR is maximized when the shape of the weighting function is proportional to the signal, that is when $w_{i,j} \propto s_{i,j}$. The signal properties of the weighted sum correspond to where the filter coefficients are centered on the signal, and the noise properties of the weighted sum correspond to where the filter is in the noise-only region.

The Matched Filter achieves maximum signal-to-noise by optimally combining neighboring elements. Convolution filters that employ matched filter coefficients produce minimum variance in the estimates of an ion's retention time, mass-to-charge ratio, and intensity.

Matched Filters Guaranteed to Produce Unique Maximum

In general, signal detection using convolution proceeds by moving the filter coefficients along the data array and obtaining a weighted sum at each point. For example, where the filter coefficients satisfy MFT, i.e., $w_i = s_i$ (the filter is matched to the signal) then in the noise-only region of the data, the amplitude of the output is dictated by the noise. As the filter overlaps the signal, the amplitude increases, and must reach a unique maximum when the filter is aligned in time with the signal.

One-Dimensional Gaussian Matched Filter

As an example of the foregoing technique for one-dimensional convolution, consider the case where the signal is a single peak resulting from a single ion. The peak (spectral or chromatographic) can be modeled as a Gaussian profile whose width is given by the standard deviation $\sigma_p$, where the width is measured in units of sample elements. The signal is then:

$$r_i = r_o \exp\left(-\frac{1}{2}\frac{(i - i_o)^2}{\sigma_p^2}\right).$$

Assume the filter boundary is set to $\pm 4\sigma_p$. According to the Matched Filter Theorem, the filter is the signal shape itself, i.e., a Gaussian, centered on zero and bounded by $\pm 4\sigma_p$. The coefficients of such a matched filter are given by:

$$f_i = \exp\left(-\frac{1}{2}\frac{i^2}{\sigma_p^2}\right), \text{ for } i > -4\sigma_p \text{ and } i < 4\sigma_p.$$

Assume further that the system samples four points per standard deviation. As a result, $\sigma_p = 4$, so $i = -16, \ldots, 16$, and the filters are 33 points wide for the present example. For the Gaussian matched filter (GMF) in one-dimension, the maximum signal of the convolved output array is 7.09 $r_o$, and the noise amplitude is 2.66 $\sigma_o$. The SNR associated with using the matched filter is $2.66(r_o/\sigma_o)$.

Gaussian Matched Filter Contrasted with Boxcar Filter in One Dimension

We contrast the GMF with a simple boxcar filter in one-dimension. Again, the signal is assumed to be a peak that is modeled by Gaussian shape described above. Assume the filter boundary for the boxcar is also set to $\pm 4\sigma_p$. The coefficients of the boxcar filter are given by:

$$f_i = \frac{1}{M} = \frac{1}{8\sigma_p + 1}.$$

The output of the boxcar filter is the average value of the input signal over M points ($M = 8\sigma_p + 1$).

Again, assume further that the system samples four points per standard deviation, so the boxcar filter is 33 points wide. For a Gaussian peak of unit height, the average signal over the peak using the boxcar filter is 0.304 $r_o$, and the standard deviation of the noise is $\sigma_o/\sqrt{33} = 0.174\sigma_o$. The SNR using the boxcar filter is $1.75(r_o/\sigma_o)$.

Thus, the SNR of the Gaussian matched filter relative to the boxcar is $2.66/1.75 = 1.52$, or more than 50% higher than that provided by the boxcar filter.

Both the matched filter and the boxcar filter are linear. The convolution of either of these filters with the Gaussian peak shape produces an output that has a unique maximum value. Thus, either of these filters can be used in the convolution of embodiments of the present invention. However, in the case of Gaussian noise, because of its higher SNR at the local maximum, the matched filter is preferred.

Gaussian Noise and Poisson Noise

The Gaussian Matched Filter is an optimum filter when the noise has Gaussian statistics. For counting detectors the boxcar filter will be optimal because it is simply a sum of all counts associated with a peak. In order to sum all the counts associated with a peak the width of the boxcar filter should be related to the width of the peak. Typically the width of the boxcar filter will be between 2 and 3 times the FWHM of the peak.

Two-Dimensional Gaussian Matched Filter

As an example of the Matched Filter technique for two-dimensional convolution, consider the case where the signal is a single peak resulting from a single ion. The peak can be modeled as a Gaussian profile in both the spectral and chromatographic directions. The spectral width is given by the standard deviation $\sigma_p$, where the width is measured in units of sample elements, and the chromatographic width is given by the standard deviation $\sigma_q$, where the width is measured in units of sample elements. The signal, centered on data matrix element $i_o, j_o$ is then:

$$r_{i,j} = r_o \exp\left(-\frac{1}{2}\frac{(i-i_o)^2}{\sigma_p^2}\right)\exp\left(-\frac{1}{2}\frac{(j-j_o)^2}{\sigma_p^2}\right).$$

Assume the filter boundary is set to $\pm 4\sigma_p$ and $\pm 4\sigma_q$. According to the Matched Filter Theorem, the filter is the signal shape itself, i.e., a Gaussian, centered on zero and bounded by $\pm 4\sigma_p$ and $\pm 4\sigma_q$. The coefficients of such a matched filter are given by:

$$f_{p,q} = \exp\left(-\frac{1}{2}\frac{p^2}{\sigma_p^2}\right)\exp\left(-\frac{1}{2}\frac{q^2}{\sigma_q^2}\right),$$

for $p > -4\sigma_p$ and $p < 4\sigma_p$ and $q > -4\sigma_q$ and $q < 4\sigma_q$.

Assume further that the system samples four points per standard deviation for both the spectral and chromatographic directions. As a result, $\sigma_p = 4$ and $\sigma_q = 4$, so that $p = -16, \ldots, 16$ and $q = -16, \ldots, 16$, and the filters are 33×33 points for the present example. For the Gaussian matched filter (GMF) in two-dimensions, the maximum signal in the convolved output matrix is $50.3\, r_o$, and the noise amplitude is $7.09\, \sigma_o$. The SNR associated with using the matched filter is 7.09 ($r_o/\sigma_o$).

A two-dimensional convolution filter performs a filter operation on the LC/MS data matrix in both the chromatographic and in the mass spectrometric directions. As a result of the convolution operation, the output convolution matrix will contain peaks whose shapes are, in general, widened or other wise distorted relative to the input LC/MS data matrix. In particular the Matched Gaussian Filter will always produce peaks in the output convolution matrix that are widened by a factor of $\sqrt{2}$ in both the chromatographic and spectral directions relative to the input peaks.

At first glance, it may seem that the widening produced by the GMF may be detrimental to the accurate estimate of critical parameters of retention time, mass-to-charge ratio, or intensity. But the Matched Filter Theorem shows that two-dimensional convolution produces apex values whose retention time, mass-to-charge ratio and intensity result form the effective combination of all spectral and chromatographic elements associated with the peak such that the resulting apex-associated values produce statistically optimum estimates of retention time, m/z, and intensity for that peak.

Gaussian Matched Filter Contrasted with Boxcar Filter in Two-Dimensions

We contrast the GMF with a simple boxcar filter in two-dimension. Again, the signal is assumed to be a peak that is modeled by Gaussian shape described above. Assume the filter boundary for the boxcar is also set to $\pm 4\sigma_p$. The coefficients of the boxcar filter are given by:

$$f_{i,j} = \frac{1}{M \times N} = \frac{1}{8\sigma_p + 1} \times \frac{1}{8\sigma_q + 1}.$$

The output of the boxcar filter is the average value of the input signal over M×N points.

Again, assume further that the system samples four points per standard deviation, so the boxcar filter is 33×33 points wide. For a Gaussian peak of unit height, the average signal over the peak using the boxcar filter is $0.092\, r_o$, and the standard deviation of the noise is $0.303\, \sigma_o$. The SNR using the boxcar filter is 3.04 ($r_o/\sigma_o$).

Thus, the SNR of the Gaussian matched filter relative to the boxcar is 7/3=2.3, or more than twice that provided by the boxcar filter.

Both the matched filter and the boxcar filter are linear. The convolution of either of these filters with the Gaussian peak shape produces an output that has a unique maximum value. Thus, either of these filters can be used in the convolution of embodiments of the present invention. However, in the case of Gaussian noise, because of its higher SNR at the local maximum, the matched filter is preferred.

Gaussian Noise and Poisson Noise

The Gaussian Matched Filter in two-dimensions is an optimum filter when the noise has Gaussian statistics. For counting detectors the boxcar filter will be optimal because it is simply a sum of all counts associated with a peak. In order to sum all the counts associated with a peak the widths of the boxcar filter should be related to the width of the peak in the spectral and chromatographic directions. Typically the widths of the boxcar filter will be between 2 and 3 times the respective FWHMs of the peak in the spectral and chromatographic directions.

Gaussian Matched Filter for the Detection of Ions in LC/MS Data Matrix

For the Gaussian Matched Filter, the specification (Step 2) of the two-dimensional convolution filter is the coefficients are Gaussian filter coefficients $f_{p,q}$ as described above, and the application (Step 3) of the filter is then according to Eq. (2) using these filter coefficients. This embodiment of Step 2 and Step 3 then provides a method to detect ions, and to determine their retention time, mass-to-charge ratio, and intensity. The results from such a method reduce the effects of detector noise and are an improvement over the method of FIG. 10.

Filters Coefficients that are not Matched Filters.

Linear weighting coefficients other than those that follow the signal shape can also be used. While such coefficients may not produce the highest possible SNR, they may have other counter-balancing advantages. The advantages include the ability to partially resolve coeluted and interfered peaks, the subtraction of baseline noise, and computational efficiency leading to high-speed operation. We analyze the limitations of the Gaussian Matched Filter and describe linear filter coefficients that address these limitations.

Issues with Gaussian Matched Filters

For a Gaussian peak, the Matched Filter Theorem (MFT) specifies the Gaussian Matched Filter (GMF) as the filter whose response has the highest signal-to-noise ratio as compared to any other convolution filter. However, the Gaussian Matched Filter (GMF) may not be optimal in all cases.

One disadvantage of the GMF is that it produces a widened or broadened output peak for each ion. To help explain peak broadening, it is well known that if a signal having positive values and a standard width, $\sigma_s$, is convolved with a filter having positive values and a standard width, $\sigma_f$, the standard width of the convolved output is increased. The signal and filter width combine in quadrature to produce an output width of $\sigma_o = \sqrt{\sigma_s^2 + \sigma_f^2}$. In the case of the GMF, where the widths of the signal and filter are equal, the output peak is wider than the input peak by a factor of approximately $\sqrt{2} \approx 1.4$, i.e., 40%.

Peak broadening can cause the apex of a small peak to be masked by a large peak. Such masking could occur, for example, when the small peak is nearly co-eluted in time and nearly coincident in mass-to-charge with the larger peak. One way to compensate for such co-elution is to reduce the width of the convolution filter. For example, halving the width of the Gaussian convolution filter produces an output peak that is only 12% more broad than the input peak. However, because the peak widths are not matched, the SNR is reduced relative to that achieved using a GMF. The disadvantage of reduced SNR is offset by the advantage of increased ability to detect nearly coincident peak pairs.

Another disadvantage of the GMF is that it has only positive coefficients. Consequently, the GMF preserves the baseline response underlying each ion. A positive-coefficient filter always produces a peak whose apex amplitude is the sum of the actual peak amplitude plus the underlying baseline response. Such background baseline intensity can be due to a combination of detector noise as well as other low-level peaks, sometimes termed chemical noise.

To obtain a more accurate measure of amplitude, a baseline subtraction operation is typically employed. Such an operation typically requires a separate algorithm to detect the baseline responses surrounding the peak, interpolate those responses to the peak center, and subtract that response from the peak value to obtain the optimal estimate of the peak intensity.

Alternately, the baseline subtraction can be accomplished by specifying filters that have negative as well as positive coefficients. Such filters are sometimes referred to as deconvolution filters, and are implemented by filter coefficients that are similar in shape to filters that extract the second derivatives of data. Such filters can be configured to produce a single local-maximum response for each detected ion. Another advantage of such filters is that they provide a measure of deconvolution, or resolution enhancement. Thus, not only do such filters preserve the apex of peaks that appear in the original data matrix, but they can also produce apices for peaks that are visible only as shoulders, not as independent apices, in the original data. Consequently, deconvolution filters can address problems associated with co-elution and interference.

A third disadvantage of the GMF is that it generally requires a large number of multiplications to compute each data point in the output convolved matrix. Thus, convolution using a GMF is typically more computationally expensive and slower than convolution using other filters. As described below, filter specifications other than the GMF can be used in embodiments of the present invention.

Advantages of Second Derivative Filters

Filters that extract the second derivative of a signal are of particular use in detecting ions according to embodiments of the present invention. This is because the second derivative of a signal is a measure of the signal's curvature, which is the most prominent characteristic of a peak. Whether considered in one or two, or more, dimensions, a peak's apex is generally the point of the peak that has the highest magnitude of curvature. Shouldered peaks are also represented by regions of high curvature. Consequently, because of their responsiveness to curvature, second derivative filters can be used to enhance peak detection as well as provide improved detection for the presence of a shouldered peak against the background of a larger, interfering peak.

The second derivative at the apex of a peak has a negative value, because the curvature of a peak at its apex is maximally negative. Some illustrative, non-limiting embodiments of the present invention will use inverted second derivative filters. Inverted second derivative filters are second derivative filters all of whose coefficients have been multiplied by −1. The output of an inverted second derivative filters is positive at a peak apex. Unless otherwise specified, all second derivative filters referred to in some examples of the present invention are taken to be inverted second derivative filters. All plots of second derivative filters are inverted second derivative filters.

Figure 15:
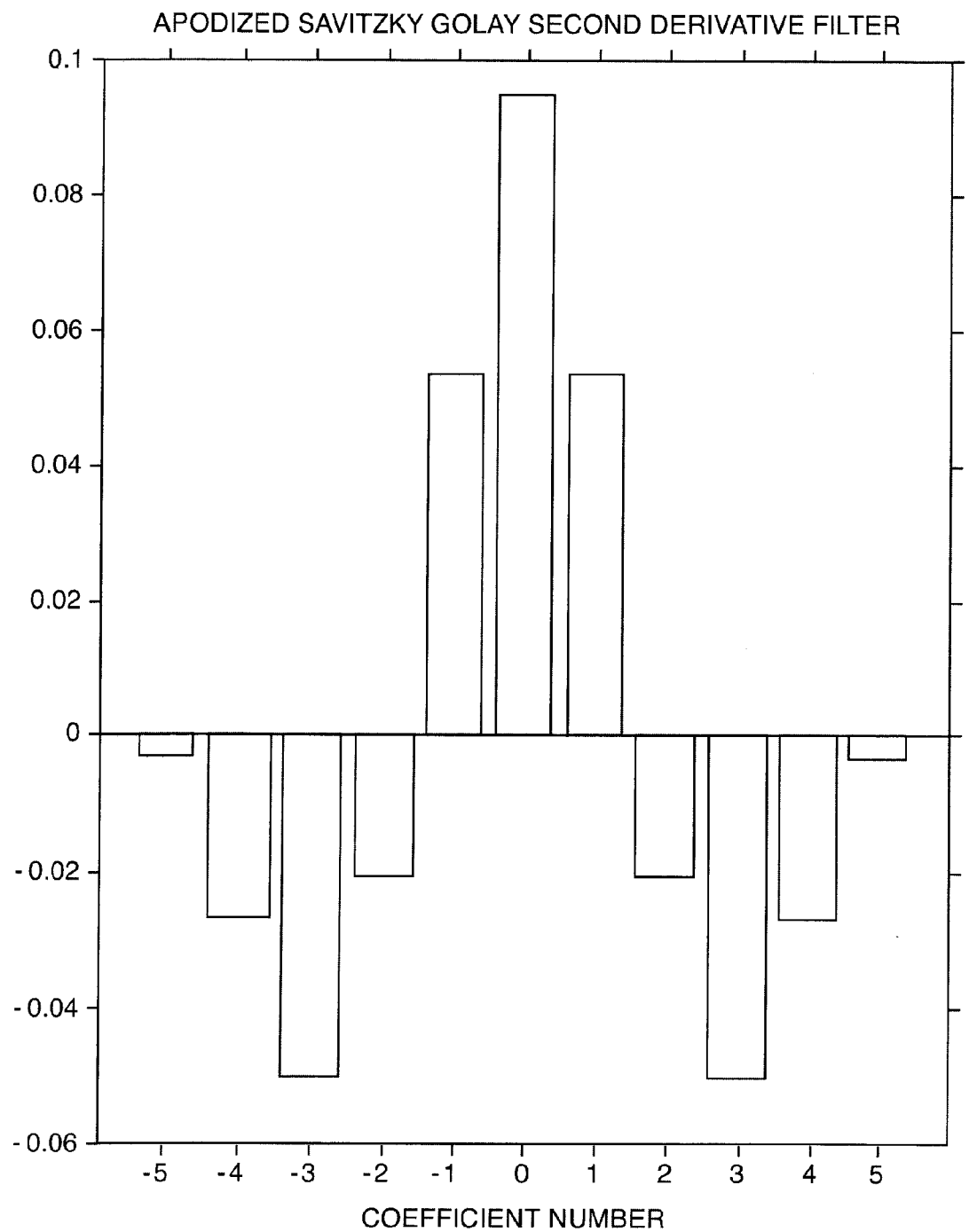
FIG. 15 illustrates an exemplary one-dimensional apodized Savitzky-Golay second-derivative filter according to an embodiment of the present invention.

The response of a second derivative filter to a constant or straight line (having zero curvature) is zero. Thus the second derivative filter has zero response to the baseline response underlying a peak. The second derivative filter responds to the curvature at the apex of the peak and not to the underlying baseline. Thus the second derivative filter carries out, in effect, the baseline subtraction. FIG. 15 illustrates the cross section of an exemplary second derivative filter that can be applied in either or both the chromatographic and spectral directions.

Second Derivative Filters in One-Dimension

In a one-dimensional case, a second derivative filter is advantageous over a smoothing filter because the amplitude of the second derivative filter at the apex is proportional to the amplitude of the underlying peak. Moreover, the second derivative of the peak does not respond to the baseline. Thus, in effect, a second derivative filter performs the operation of baseline subtraction and correction automatically.

A disadvantage of second derivative filters is that they can have the undesirable effect of increasing noise relative to the peak apex. This noise-increasing effect can be mitigated by pre-smoothing the data or increasing the width of a second-derivative filter. For example, in one embodiment of the present invention, the width of the second-derivative convolution filter is increased. Increasing the width of the second-derivative convolution filter improves its ability to smooth the data in the input data matrix during convolution.

Savitzky-Golay Filters for Smoothing and Obtaining a Second-Derivative

For a single-channel of data (spectrum or chromatogram), a conventional method for smoothing data (i.e., reducing the effects of noise) or for differentiating data is through the application of a filter. In an embodiment of the present invention, smoothing or differentiating is performed on a one-dimensional data array by convolving that data array corresponding to the single spectrum or chromatogram with a set of fixed-value filter coefficients.

For example, well-known finite impulse response (FIR) filters can be specified with appropriate coefficients to perform a variety of operations including those of smoothing and differentiation. See example, KARL. Suitable smoothing filters generally have a symmetric, bell shaped curve, with all positive values, and a single maximum. Exemplary smoothing filters that can be used include filters having Gaussian, triangular, parabolic, trapezoidal shapes and co-sinusoidal shapes, each of which is characterized as a shape having a single maximum. Smoothing filters having asymmetric, tailed curves can also be used in embodiments of the present invention.

A family of FIR filters that can be specified to smooth or differentiate one-dimensional arrays of data is the well-known Savitzky-Golay filters. See example, in A. SAVITZKY & M. J. E. GOLAY, ANALYTICAL CHEMISTRY, VOL. 36, PP. 1627-1639 which is hereby incorporated by reference herein. The Savitzky-Golay (SG) polynomial filters provides a suitable family of smoothing and differentiating filters that are specified by sums of weighted polynomial shapes. The 0th order smoothing filter in this family of filters is a flat top (boxcar) filter. The second order smoothing filter in this family of filters is a parabola that has a single, positive maximum. The second order filter that obtains a second derivative in this family of filters is a parabola that has a single, negative maximum with zero mean. The corresponding inverted second derivative SG filter has a positive maximum.

Apodized Savitsky-Golay Filters

A modification of SG filters yields a class of smoothing and second derivative filters that work well in the present invention. These modified SG filters are known as Apodized Savitksy-Golay (ASG) filters. The term apodization refers to filter coefficients that are obtained by applying an array of weight coefficients to a least-squares derivation of SG filter coefficients. The weight coefficients are the apodization function. For the ASG filter used in embodiments of the present invention, the apodization function is a cosine window (defined by COSINEWINDOW) in the software code below. This apodization function is applied, via weighted least-squares to a box-car filter to obtain the ASG smoothing filter, and to a second derivative SG quadratic polynomial, to obtain the ASG second derivative filter. The box car filter and second derivative quadratic are, by themselves, examples of Savitzky-Golay polynomial filters.

Every SG filter has a corresponding Apodized Savitzky-Golay (ASG) filter. An ASG filter provides the same basic filter function as the corresponding SG filter, but with higher attenuation of unwanted high-frequency noise components. Apodization preserves the smoothing and differentiation properties of SG filters, while producing much improved high-frequency cutoff characteristics. Specifically, apodization removes sharp transitions of the SG filter coefficients at the filter boundaries, and replaces them with smooth transitions to zero. (It is the cosine apodization function that forces the smooth transition to zero.). Smooth tails are advantageous because they reduce the risk of double counting due to high-frequency noise described above. Examples of such ASG filters include cosine smoothing filters and cosine-apodized second order polynomial Savitzky-Golay second derivative filters.

In the preferred embodiment of the present invention, these smoothing and second derivative ASG filters are specified for application to the column and rows of the LC/MS data matrix.

Example of Rank-1 Filter for Two-Dimensional Convolution

As an example of the application of a rank-1 formulation for two-dimensional convolution, we could choose $f_p$ and $g_q$ in Eq. (3) to have Gaussian profiles. The resulting $F_{pq}$ has a Gaussian profile in each row and column. The values for $F_{pq}$ will be close, but not identical to $f_{p,q}$ for the two-dimensional GMF. Thus, this particular rank-1 formulation will perform similarly to the GMF, but with a reduction in computation time. For example, in the example provided above, for example, where P and Q were equal to 20, computational load by using the rank-1 filter computational requirements reduced by a factor of 400/40=10.

The choice of $f_p$ and $g_q$ to have Gaussian profiles and the application of these filters according to Eq. (3) constitutes one embodiment of Step 2 and Step 3 according to the present invention.

But for other embodiments of the present invention, we can apply separate filters for each dimension of a rank-1 filter. In an embodiment of the present invention, for example, $f_p$ (the filter applied in the spectral direction) is a smoothing filter and $g_q$ (the filter applied in the chromatographic direction) is a second derivative filter. Through such filter combinations, different rank-1 filter implementations can be specified that overcome problems typically associated with filtering. For example, the filters comprising a rank-1 filter can be specified to address the aforementioned problems associated with GMFs.

The aforementioned rank-1 filters, implemented by Eq. 3 are more computationally efficient and therefore faster than the GMF implemented by Eq. 2. Moreover, the specified combination of filters provides a linear, baseline corrected response that can be used for quantitative work.

Furthermore, the combination of filters sharpens, or partially deconvolves fused peaks in the chromatographic direction.

An exemplary rank-1 filter for use in embodiments of the present invention that has the aforementioned advantages comprises a first filter, $f_p$, that is a co-sinusoidal ASG smoothing filter, whose FWHM is about 70% of the FWHM of the corresponding mass peak and a second filter, $g_q$, that is an ASG second-derivative filter, whose zero crossing width is about 70% of the FWHM of the corresponding chromatographic peak. Other filters and combinations of filters can be used as the rank-1 filters in other embodiments of the present invention.

Figure 16A:
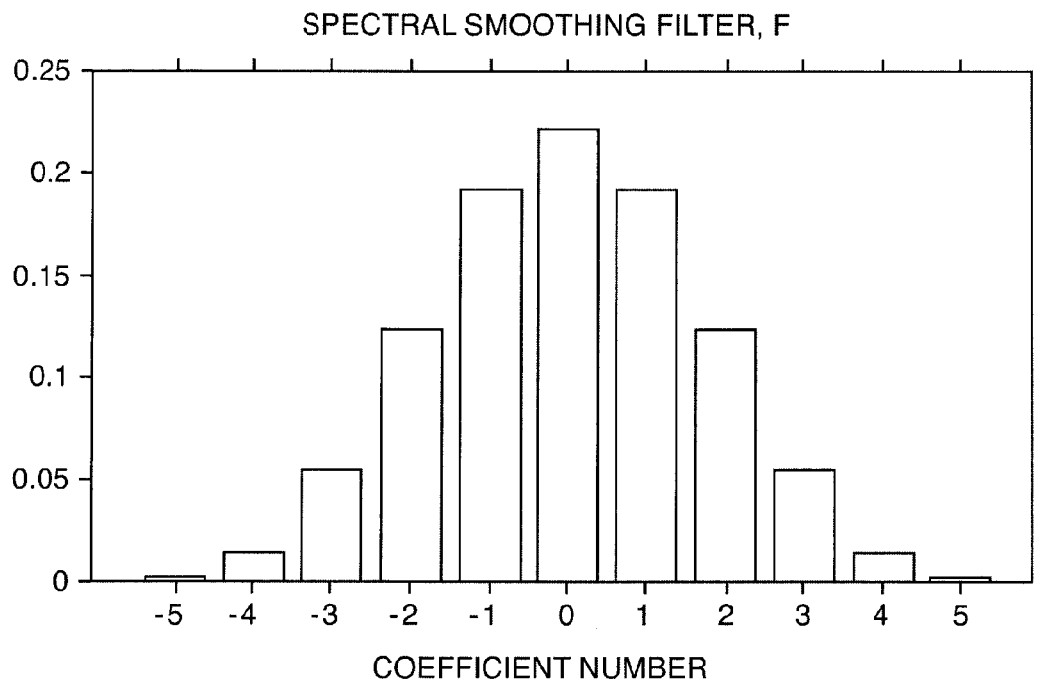
FIG. 16A illustrates the cross section of an exemplary one-dimensional filter in the spectral (m/z) direction according to an embodiment of the present invention.
Figure 16B:
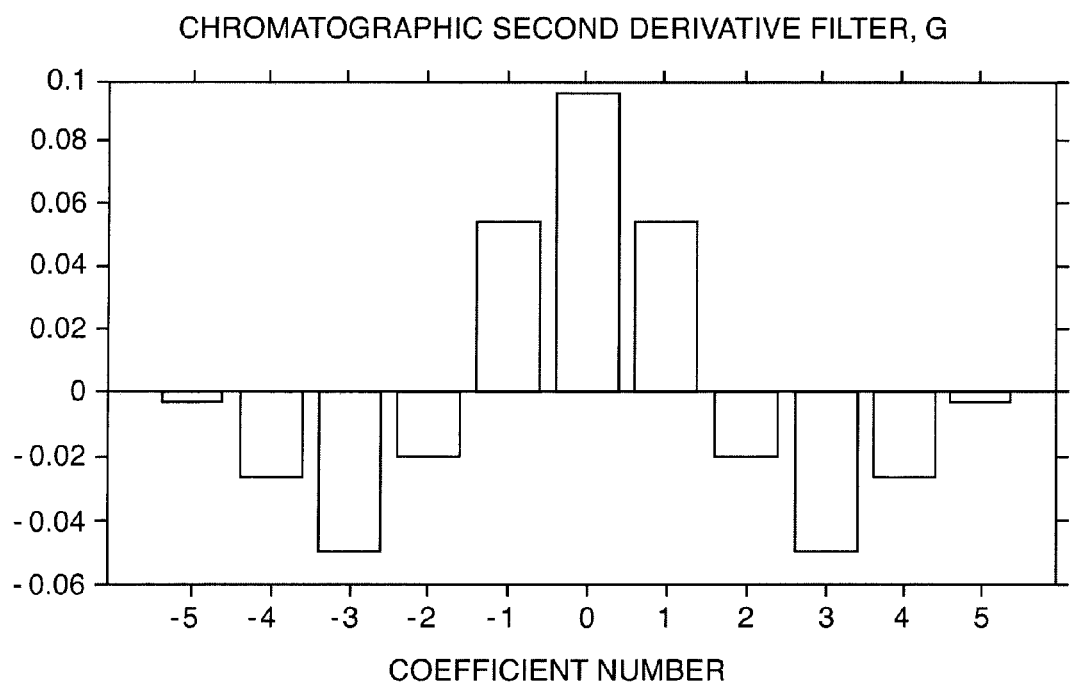
FIG. 16B illustrates the cross section of an exemplary one-dimensional filter in the chromatographic (time) direction according to an embodiment of the present invention.
Figure 16D:
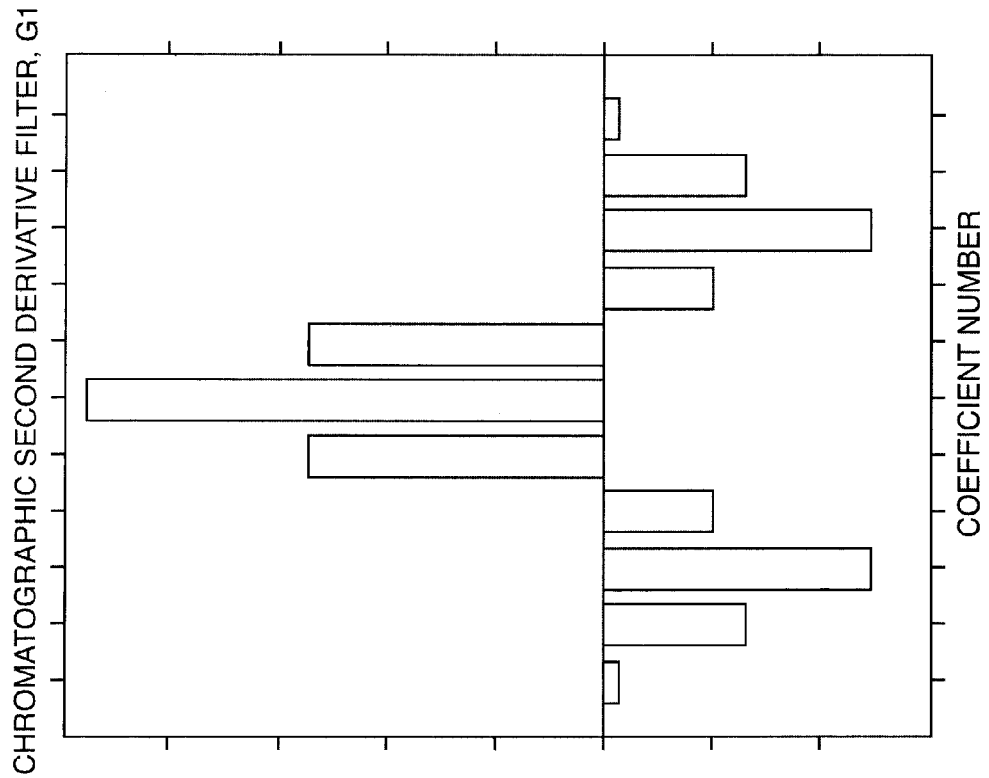
FIG. 16D illustrates the cross section of an exemplary one-dimensional second derivative filter g1 in the chromatographic direction according to an embodiment of the present invention.
Figure 16C:
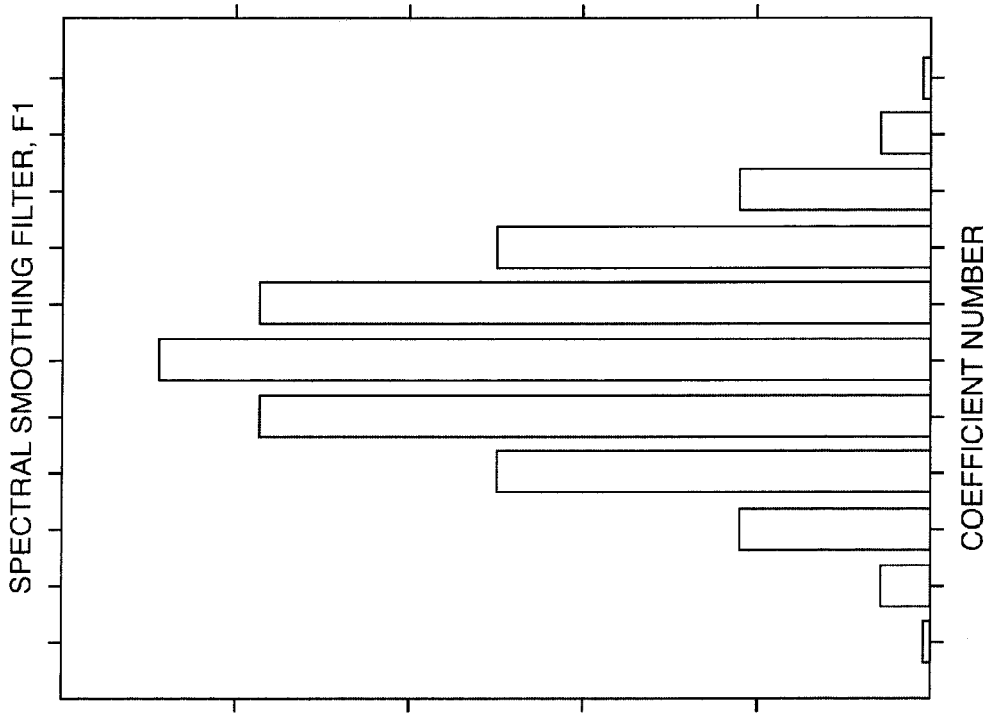
FIG. 16C illustrates the cross section of an exemplary one-dimensional smoothing filter f1 in the spectral (m/z) direction according to an embodiment of the present invention.

FIG. 16A illustrates a cross section in the spectral direction of an exemplary co-sinusoidal ASG smoothing filter for use in a rank-1 filter to apply to the columns of the LC/MS data matrix to form an intermediate matrix. FIG. 16B illustrates a cross section in the chromatographic direction of an exemplary, ASG second derivative filter to apply to the rows of the generated intermediate matrix.

The filter functions of $f_p$ and $g_q$ can be reversed. That is, $f_p$ can be the second derivative filter and $g_q$ can be the smoothing filter. Such a rank-1 filter deconvolves shouldered peaks in the spectral direction, and smoothes in the chromatographic direction.

Note that both $f_p$ and $g_q$ should not be second derivative filters. The rank-1 product matrix resulting where both $f_p$ and $g_q$ are second derivative filters contains not one, but a total of five, positive local maxima when convolved with an ion peak. The four additional positive apices are side-lobes that arise from the products of the negative lobes associated with these filters. Thus, this particular combination of filters results in a rank-1 filter that is not suitable for the proposed method.

The rank-2 formulation described below implements a filter that has properties of smoothing filters and second-derivative filters in both the spectral and chromatographic directions.

Several filter combinations for embodiments of the present invention that use a rank-1 convolution filters are provided Table 2.

TABLE 2

| Filter combinations for rank-1 filter | |
|---|---|
| m/z | Time |
| Smoothing | Smoothing |
| Smoothing | $2^{nd}$ derive |
| $2^{nd}$ derive | Smoothing |

Each filter combination is an embodiment of Step 2, and each, being a rank-1 filter, is applied using Eq. (3), thereby embodying Step 3. Other filters and combinations of filters can be used as the rank-1 filters in other embodiments of the present invention.

Example of Rank-2 Filter for Two-Dimensional Convolution, which is the Preferred Embodiment The rank-2 filter requires specification of two filters for each of two dimensions. In a preferred embodiment of the present invention, the four filters are specified to address the problems associated with the GMF as described above in a computationally efficient manner.

For example, in an embodiment of the present invention, the first rank-1 filter comprises a spectral smoothing filter as $f_p^1$ and a chromatographic second derivative filter as $g_q^1$. An exemplary such smoothing filter is a co-sinusoidal filter, whose FWHM is about 70% of the FWHM of the corresponding mass peak. An exemplary such second-derivative filter is ASG second-derivative filter, whose zero crossing width is about 70% of the FWHM of the corresponding chromatographic peak. The second rank-1 filter comprises a spectral second derivative filter as $f_p^2$ and a chromatographic smoothing filter as $g_q^2$. An exemplary such second derivative filter is a second derivative ASG filter, whose zero-crossing width is about 70% of the FWHM of the corresponding mass peak. An exemplary such smoothing filter is a co-sinusoidal filter, whose FWHM is about 70% of the FWHM of the corresponding chromatographic peak. Other filters and filter combinations can be used in embodiments of the present invention. The cross sections of such filters are illustrated in FIGS. 16C, 16D, 16E, and 16F respectively.

The rank-2 filter described above has several advantages over the GMF. Because it is a rank-2 filter, it is more computationally efficient then the GMF and consequently faster in execution. Moreover, because each cross-section is a second derivative filter whose coefficients sum to zero, it provides a linear, baseline corrected response that can be used for quantitative work and it sharpens, or partially deconvolves, fused peaks in the chromatographic and spectral directions.

In a preferred rank-2 filter embodiment of the present invention, the filter widths of each of the column filters (in terms of number of coefficients) are set in proportion to the spectral peak width and the filter widths of each of the row filters (in terms of number of coefficients) are set in proportion to the chromatographic peak width. In the preferred embodiment of the present invention, the widths of the column filters are set equal to each other, and in proportion to the FWHM of a spectral peak. For example, for a spectral peak width FWHM of 5 channels, the filter width may be set to 11 points, so the filter width of both the smoothing and second derivative spectral filter will be set to the same value of 11 points. Analogously, in the preferred embodiment, the widths of the row filters are set equal to each other, and in proportion to the FWHM of a chromatographic peak. For example, for a chromatographic peak width FWHM of 5 channels, the filter width can be set to 11 points, so the filter width of both the smoothing and second derivative spectral filters will be set to the same value of 11 points. Choosing the filter widths in this manner results in rank-1 filters comprising the rank-2 filter having equal dimensions. That is, if the first rank-1 filter has dimension M×N, then the dimension of the second rank-1 filter also has dimension M×N. It should be noted that the a rank-2 filter need not be comprised of rank-1 filters having equal dimensions and that any suitable rank-1 filters can be summed to produce a rank-2 filter.

The rank-1 filters are summed to construct the rank-2 filter, therefore the filters must be normalized in a relative sense prior to summing. In the preferred embodiment, the first rank-1 filter is a smoothing filter in the spectral direction and is a second derivative filter in the chromatographic direction. If this filter is weighted more than the second rank-1 filter, then the combined filter gives more emphasis to smoothing in the spectral direction and baseline-subtraction and deconvolution of peaks in the chromatographic direction. Thus the relative normalization of the two rank-1 filters determines the relative emphasis of smoothing and differentiation in the chromatographic and spectral directions.

For example, consider two rank-1 filters:

$$F_{p,q}^1 = f_p^1 g_q^1 \quad (11)$$

$$F_{p,q}^2 = f_p^2 g_q^2 \quad (12)$$

where, equation (11) is the first rank-1 filter, and equation (12) is the second rank-1 filter. In a preferred embodiment of the present invention, each rank-1 filter is normalized so that the sum of its coefficients squared equals one. This normalization gives equal weight for smoothing and differentiation to the spectral and chromatographic directions. That is, for rank-1 filters, each having dimensions of M×N:

$$\sum_{q=1}^{N} \sum_{p=1}^{M} (f_p^1 g_q^1)^2 = 1$$

$$\sum_{q=1}^{N} \sum_{p=1}^{M} (f_p^2 g_q^2)^2 = 1.$$

The smoothing filters and second derivative filters of the preferred embodiments can be normalized to satisfy this criterion by applying an appropriate scaling factor to the coefficients of the respective rank-1 matrices.

Moreover, in the preferred embodiment, the row dimension of each rank-1 filter is the same, and the column dimensions of each rank-1 filter is the same. As a result, the coefficients can be added to obtain the rank-2 convolution filter's point source as follows:

$$F_{p,q} = f_p^1 g_q^1 + f_p^2 g_q^2 \quad (13)$$

From equation (13), it can be seen that the relative normalization of the two rank-1 filters is needed to determine the two-dimensional convolution filter F Filter Coefficients for Preferred Embodiment of Two-Dimensional Convolution Filter An exemplary rank-2 filter is described with respect to FIGS. 17A-K. This filter is an embodiment of Step 2 and Step 3 that can be used to detect ions, subtract baseline response, resolved partially fused peaks, and perform with high computational efficiency.

In particular, this rank-2 filter is useful for detecting shouldered peaks. A rank-2 filter according to embodiments of the present invention can comprise a second derivative filter in both the chromatographic and spectral directions. Due to the responsive nature of second derivatives filters to curvature, such a rank-2 filter can detect shouldered peaks wherein the apex of the shouldered peak may not be evident in the data. Given that the rank-2 filter comprises a second derivative filter, which measures curvature, the apex of the second peak, which is not seen in the data directly, can be detected as a separate apex in the output convolved matrix.

Figure 17A:
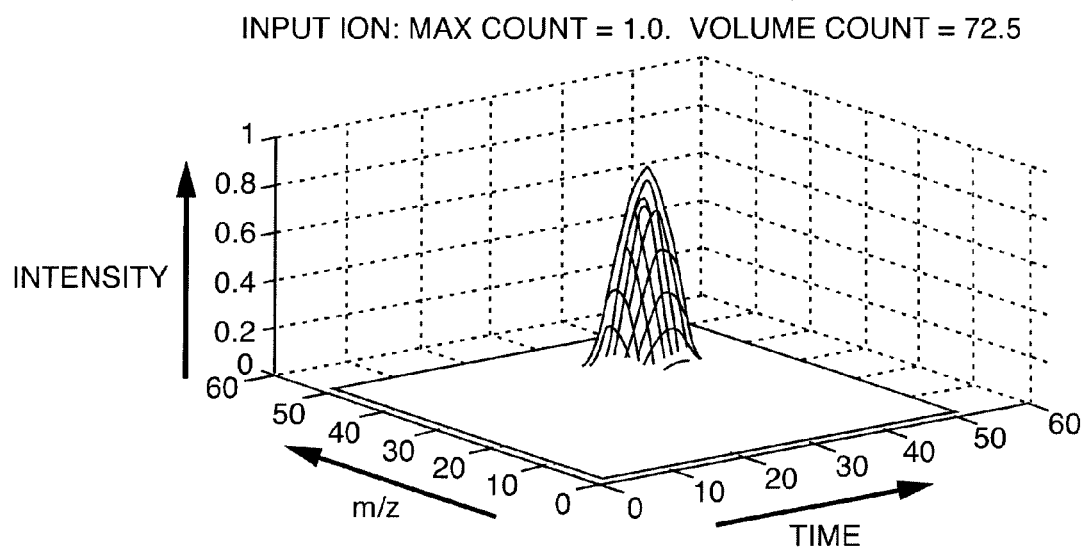
FIG. 17A illustrates an exemplary peak that can be generated by LC/MS data as stored in a data matrix according to embodiments of the present invention.
Figure 17B:
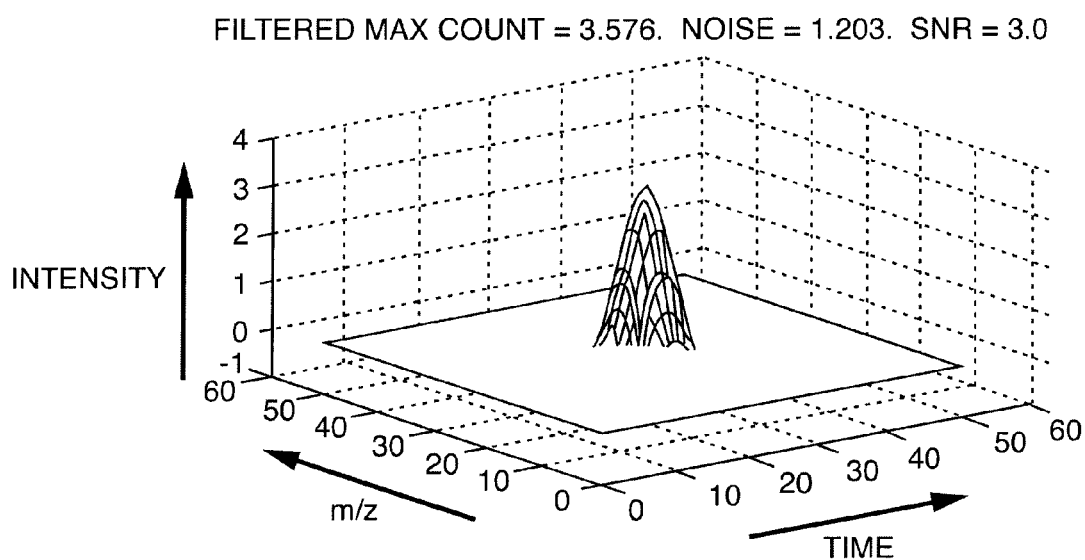
FIG. 17B illustrates a point-source response (finite impulse response) of an exemplary rank-2 filter according to an embodiment of the present invention.

FIG. 17A is a graphical representation of a simulated peak that can be generated in LC/MS data, wherein the horizontal axes represent time of scan and m/z channel as shown, and the vertical axis represents intensity. FIG. 17B illustrates the convolution filter matrix corresponding to the rank-2 filter, according to a preferred embodiment of the present invention.

In this simulation, the spectral and chromatographic peak widths of all ions are 8 points, FWHM. The number of filter coefficients for all four filters is 15 points.

FIG. 17C illustrates a simulation of two LC/MS peaks that have the same mass, and are nearly, but not identically, co-incident in time. FIG. 17D illustrates that the peak cross section is a pure peak in mass, and FIG. 17E illustrates that the peak cross section exhibits a shoulder 1704 in time. FIGS. 17F through 17H illustrate the effect of simulated counting (shot noise) on each sampled element comprising the shouldered peak illustrated in FIGS. 17D-17E. FIGS. 17G and 17H illustrate the cross sections arising due to the added counting noise. As can be seen in both FIGS. 17G and 17H, many local maxima are generated as a result of the counting noise. Thus, it can be seen that even though only two ions are present, counting noise can produce numerous spurious local maxima that could cause false positive ion detection.

FIGS. 17I-K illustrates the results of convolving a rank-2 filter with the simulated data. The resultant output convolved matrix (represented by the contour plot of FIG. 17I) comprises two distinct peaks 1702 and 1706. Peak 1702 is the peak associated with the more intense of the two ions, and peak 1706 is the peak of the less intense shouldered ion. FIG. 17J is a cross section of the output convolved matrix in the spectral (mass-to-charge ratio) direction. FIG. 17K is a cross section of the output convolved matrix in the chromatographic (time) direction.

What is observed by reviewing FIGS. 17I-K is that a rank-2 filter-based embodiment of the present invention reduces the effect of counting noise and deconvolutes shouldered peaks to produce multiple local maxima. Each local maximum is associated with an ion. As a result, this embodiment of the present invention also reduces the false positives rate. The ion parameters, m/z, retention time and intensity are obtained by analyzing the detected local maxima as described above.

Any Filter can be Used if it Produces a Single Local Maximum

The filters and convolution methods described above can be used to detect ions in an LC/MS data matrix. Other sets of filter coefficients can be chosen as embodiments of Step 2.

The input signal is a peak in the LC/MS data matrix that has a unique maximum, so the convolution filter of Step 2 must faithfully maintain that unique positive maximum through the convolution process. The general requirement that a convolution filter must satisfy for it to be an embodiment of Step 2 is as follows: the convolution filter must have an output that produces a unique maximum when convolved with an input having a unique maximum.

For an ion that has a bell-shaped response, this condition is satisfied by any convolution filter whose cross sections are all bell-shaped, with a single positive maximum. Examples of such filters include inverted parabolic filters, triangle filters, and co-sinusoidal filters. Specifically, any convolution filter that has the property that it has a unique, positive valued apex makes that filter a suitable candidate for use in embodiments of the present invention. A contour plot of the filter coefficients can be used to examine the number and location of the local maxima. All row, column and diagonal cross sections through the filter must have a single, positive, local maximum. Numerous filter shapes meet this condition and can therefore be employed in embodiments of the present invention.

Boxcar can be Used Because it Produces a Single Local Maximum

Another filter shape that is acceptable is a filter having a constant value (i.e., a boxcar filter). This is because convolution of a peak with a boxcar filter produces an output that has a single maximum. A well-known characteristic of boxcar filters that is advantageous in embodiments of the present invention is that such a shape produces minimum variance for a given number of filter points. Another advantage of boxcar filters is that in general they can be implemented with fewer multiplications than filters having other shapes such as Gaussian or co-sinusoidal filters.

The dimensions of the boxcar should match the extent of the peak in both the spectral and chromatographic directions. If the boxcar is too small, not all counts associated with a peak will be summed. If the boxcar is too large, then counts from other, neighboring peaks may be included.

However, boxcar filters also have distinct disadvantages for some applications to which the present invention might be applied. For example, the transfer function of boxcar filters reveals that they pass high frequency noise. Such noise can increase the risk of double counting peaks for low amplitude signals (low SNR), which might be undesirable in some applications of the present invention. Consequently, filter shapes other than boxcar shapes are generally preferred in applications of the present invention.

Second Derivative Filters can Produce a Single Local Maximum

Another suitable class of convolution filters that have an output that produces a unique maximum when convolved with an input having a unique maximum are filters that have a single, positive local maximum, but have negative sidelobes. Examples of such filters include second derivative filters, which are responsive to curvature. A suitable second derivative filter can be specified by subtracting the mean from a smoothing filter. Though such filters can be assembled from combinations of boxcar, triangular and trapezoidal shapes, the most common specification of filters that differentiate data are Savitzky-Golay polynomial filters.

Gaussian Noise and Poisson Noise

The Gaussian Matched Filter is an optimum filter when the noise has Gaussian statistics. The noise from counting detectors has Poisson statistics. In the case of Poisson noise the boxcar filter may be an optimal filter for use in detection because the boxcar simply sums all counts associated with a peak. However, many of the limitations described for GMF still apply to the boxcar filter, even in the case of Poisson noise. The boxcar filter cannot subtract baseline noise and cannot resolve interfered and coeluted peaks. In addition, the transfer function of the boxcar filter may allow for double counting for peak apices.

The rank-2 filter of the preferred embodiments is a compromise in SNR for both the case of Gaussian noise and Poisson noise. This rank-2 this filter has the advantage of baseline subtraction and partial resolution of overlapped peaks.

Role of Peak Width in Determining Filter Coefficients

In embodiments of the present invention, the coefficients of the convolution filter F to be convolved with the input matrix D are chosen to correspond to the typical shape and width of a peak corresponding to an ion. For example, the cross section of the central row of filter F matches the chromatographic peak shape; the cross section of the central column of filter F matches the spectral peak shape. It should be noted that although the width of the convolution filter can be matched to the FWHM of the peak (in time and in mass-to-charge), such width matching is not required.

Interpretation of Ion Intensity and Scaling of Filter Coefficients

In the present invention, the intensity measurement estimate is the response of the filter output at the local maximum. The set of filter coefficients with which the LC/MS data matrix is convolved determines the scaling of the intensity. Different sets of filter coefficients result in different intensity scalings, so this estimate of intensity of the present invention does not necessarily correspond exactly to peak area or peak height.

However, the intensity measurement is proportioned to peak area or to peak height since the convolution operation is a linear combination of intensity measurements. Thus the response of the filter output at local maximum is in proportion to the molecule's concentration in the sample that gave rise to the ion. The response of the filter output at local maximum can then be used for the purpose of quantitative measurement of molecules in the sample in the same was as the area of height of the peak of the ion's response.

Provided a consistent set of filters is used to determine the intensities of standards, calibrators and sample, the resulting intensity measurements produce accurate, quantifiable results regardless of the intensity scaling. For example, intensities generated by embodiments of the present invention can be used to establish concentration calibration curves which can thereafter be used to determine the concentration of analytes.

Asymmetric Peak Shapes

The examples above have assumed that an ion's peak shapes in the spectral and in the chromatographic directions are Gaussians, and therefore symmetric. In general, peak shapes are not symmetric. A common example of an asymmetric peak shape is that of a tailed Gaussian; a Gaussian convolved with a step-exponential. The methods described here still apply to peak shapes that are asymmetric. In the case where a symmetric filter is applied to an asymmetric peak, the location of the apex in the output convolved matrix will not, in general, correspond exactly to the apex location of the asymmetric peak. However, any offset originating from peak asymmetry (in either the chromatographic or the spectral direction) will be, effectively a constant offset. Such an offset is easily corrected for by conventional mass spectrometric calibration, and by retention time calibration using an internal standard.

According to The Matched Filter Theorem, the optimum shape for detection for an asymmetric peak will be the asymmetric peak shape itself. However, provided the width of the symmetric filter matches the width of the asymmetric peak, the difference in detection efficiency between a symmetric filter and a matched asymmetric filter will be minimal for the purposes of this invention.

Changing Filter Coefficients to Interpolate and Offset Data

Another use of coefficient modification is to provide interpolation to account for small changes due to calibration of the mass spectrometer. Such coefficient modification can occur from spectrum to spectrum. For example, if a change in mass calibration causes an offset of a fraction of a channel by 0.3, then column filters (both smoothed and second derivative) can be derived that estimate what the output would be in the absence of such a mass offset. In this manner, a real-time mass correction can be made. Typically, the resulting filter is slightly asymmetric.

Dynamic Filtering

Filter characteristics such as the filter width scaling can be changed in response to known changing characteristics of the LC separation or of the MS scans. For example, in a TOF mass spectrometer, the peak width (FWHM) is known to change from low values (such as 0.010 amu) to wider values (such as 0.130 amu) over the course of each scan. In a preferred embodiment of the present invention, the number of coefficients of the smoothing and differentiating filters is set equal to approximately twice the FWHM of the spectral peak. As the MS scan progresses, for example, from low to high mass, the filter width of both the smoothing and second derivative column filters employed by the preferred embodiment can be expanded accordingly to preserve the relationship between filter width and peak width. Analogously, if the width of the chromatographic peak is known to change during a separation, the width of the row filters can be expanded or contracted to preserve the relationship between filter width and peak width.

Real-Time Embodiments of Rank-1 and Rank-2 Filters

In conventional LC/MS systems, spectra are acquired as the separation progresses. Typically spectra are written to computer memory at a constant sample rate (e.g., at a rate of once per second). After one or more complete spectra are collected, they are written to more permanent storage, such as to a hard disk memory. Such post collection processing can be performed in embodiments of the present invention as well. Thus, in one embodiment of the present invention, the convolution matrix is generated only after the acquisition is complete. In such an embodiment of the present invention, the original data and the convolved matrix itself are stored as is the ion parameter list obtained from analyzing the detected local maxima.

In addition, embodiments of the present invention using rank-1 and rank-2 filters can be configured to operate in real time. In a real-time embodiment of the present invention, the columns of the convolution matrix are obtained while the data is being acquired. Thus, the initial columns (corresponding to spectra) can be obtained, analyzed, and have their ion parameters written to disk before the acquisition of all spectra is complete.

This real-time embodiment of the present invention essentially analyzes the data in computer memory, writing only the ion parameter list to the permanent hard disk drive. In this context, real time means that rank-1 and rank-2 filtering is performed on the spectra in computer memory as the data is being acquired. Thus, ions detected by the LC/MS in the beginning of the separation are detected in the spectra written to disk, and the portion of the ion parameter list containing parameters associated with these ions is also written to disk as the separation proceeds.

There is typically a time delay associated with beginning real-time processing. The spectra that contain ions that elute in a chromatographic peak at time, t, and width, $\Delta t$, can be processed as soon as they are collected. Typically, real-time processing begins at time $t+3\Delta t$, i.e., after 3 spectra are initially collected. Ion parameters determined by analysis of this chromatographic peak are then appended to an ion parameters list being created and stored in permanent storage, such as a computer disk. The real-time processing proceeds according to the techniques described above.

Advantages of real-time processing include: (1) quick acquisition of the ion parameter list; (2) triggering real-time processes based upon information in the ion parameter list. Such real-time processes include fraction collection and stop flow techniques to store eluent for analysis. An exemplary such stop-flow technique traps the eluent in a nuclear-magnetic-resonance (NMR) spectral detector.

Figure 18:
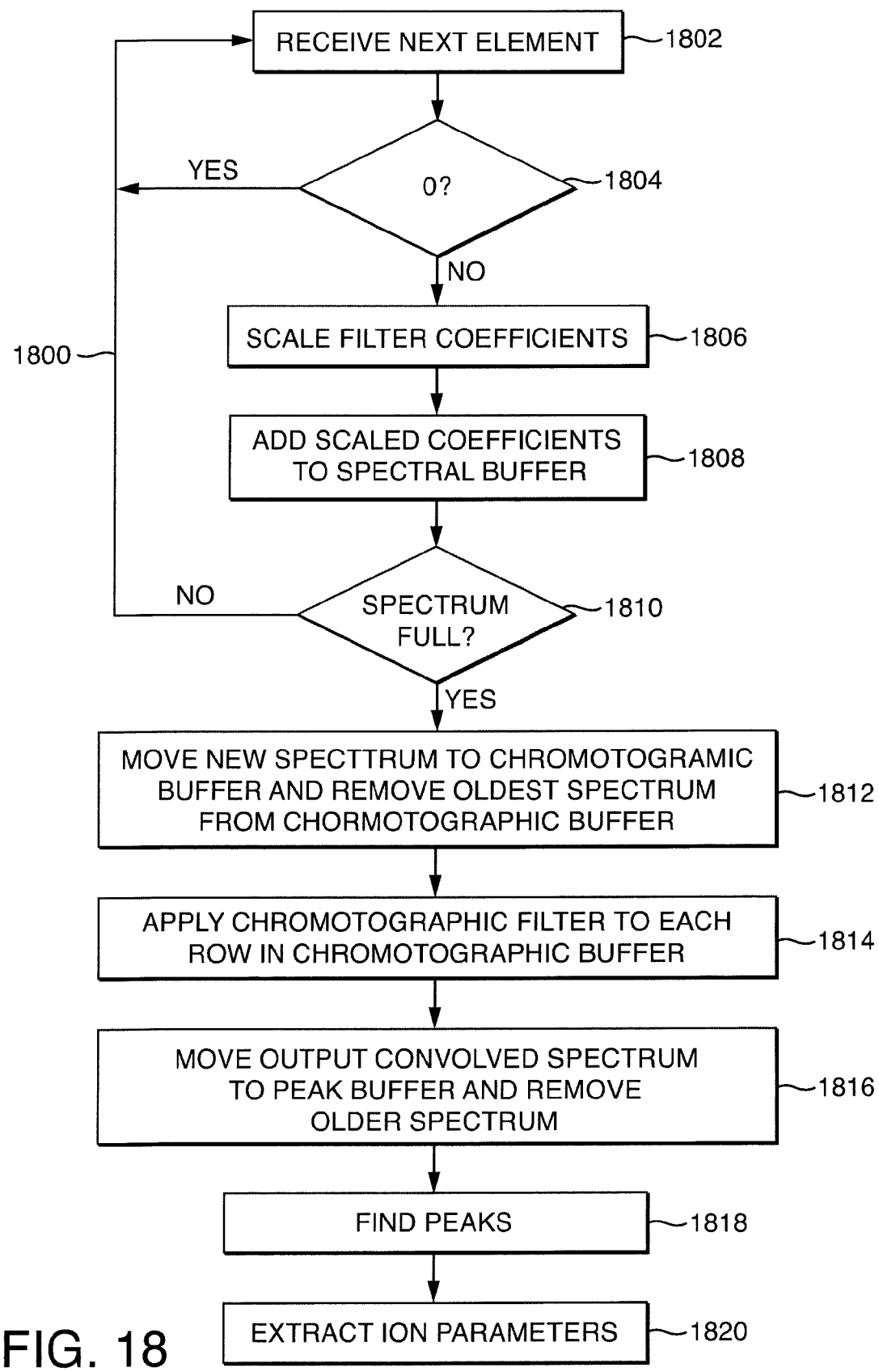
FIG. 18 illustrates a flow chart for performing real-time processing of data according to an embodiment of the present invention.
Figure 19A:
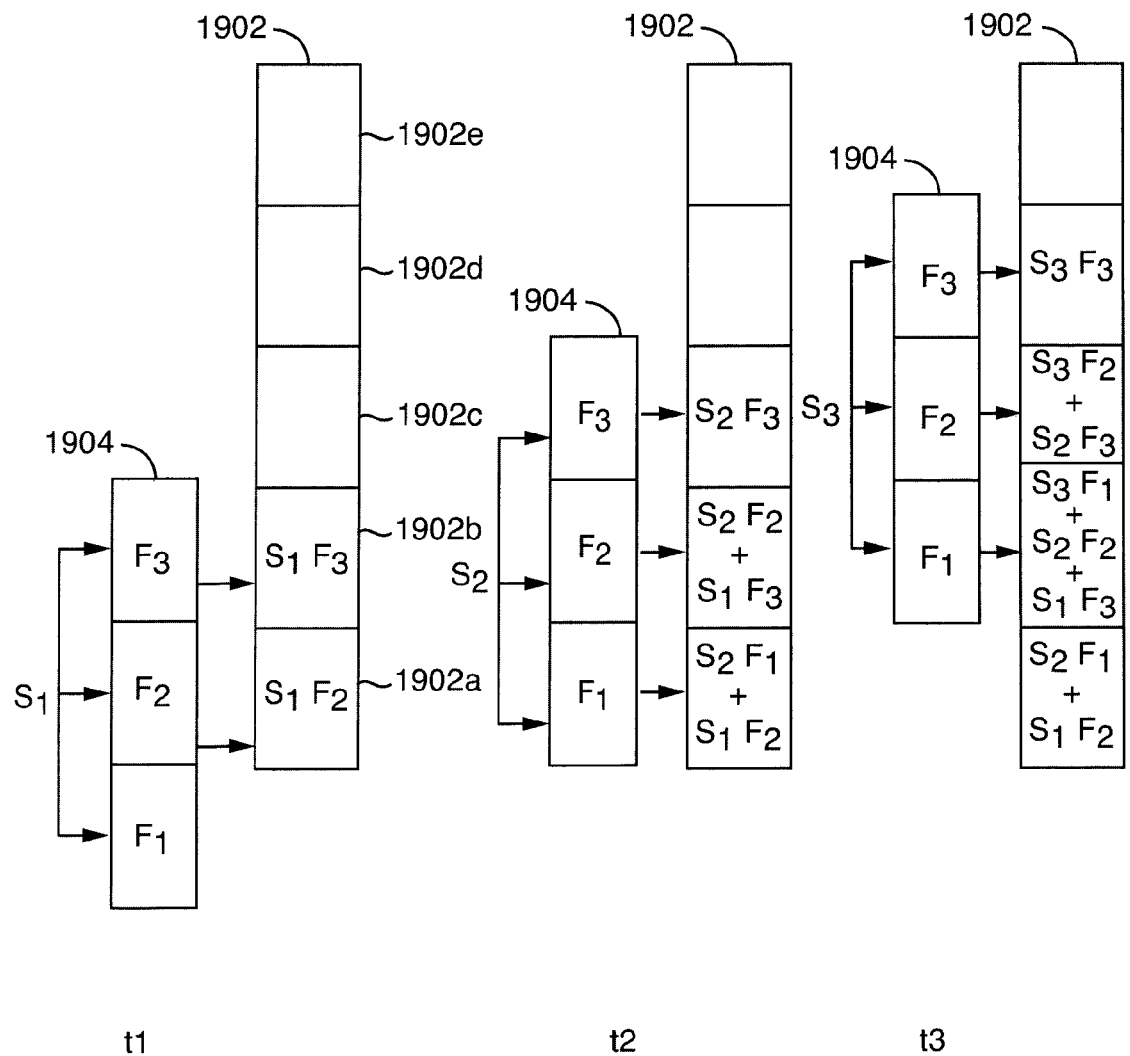
FIG. 19 is a graphical illustration of a method for performing real-time processing of a data according to the method of the flow chart of FIG. 18.
Figure 19B:
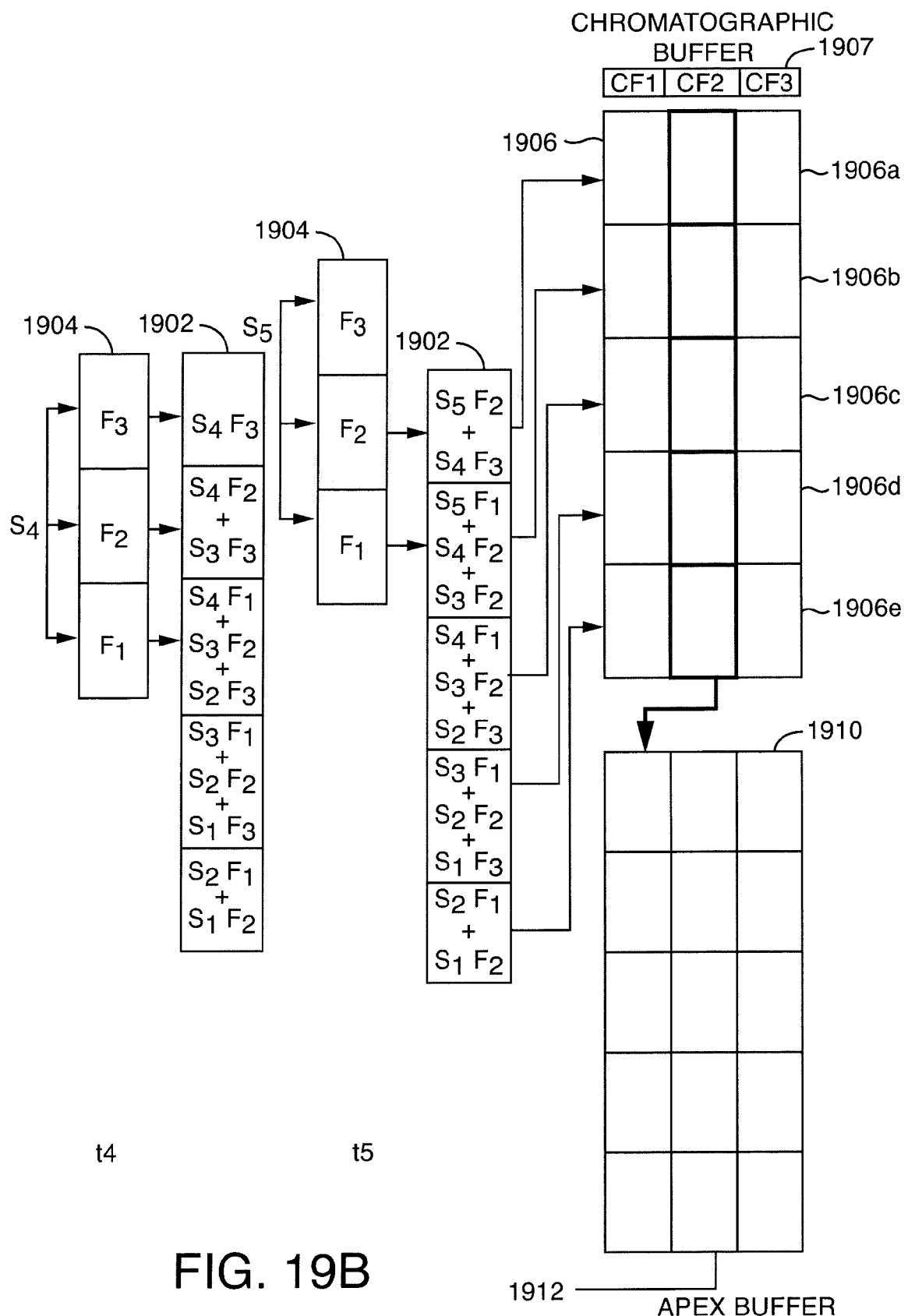

FIG. 18 is a flow chart 1800 illustrating a method for real-time processing according to a preferred embodiment of the present invention. The method can be executed in hardware, for example, for example in a DSP-based design or in software, such as in the DAS described above. It would be apparent to those skilled in the art how to configure such hardware or software based on the following description. For ease of description, the method is described as if performed by the DAS executing software. FIG. 19 illustrates a spectral buffer 1902, chromatographic buffer 1906 and an apex buffer 1910 and how they are manipulated in performing the method illustrated in flow chart 1800.

The DAS begins the method in step 1802 by receiving the next spectral element. In FIG. 19, these spectral elements are shown as S1, S2, S3, S4 and S5 and correspond to spectral elements received at times T1, T2, T3, T4 and T5 respectively. In step 1804, the DAS determines whether the received spectral element is 0 or not. If the received spectral element is 0, the DAS continues the method in step 1802 by receiving the next spectral element. If the spectral element is not zero, its intensity is used to scale the coefficients of a spectral filter 1904. In the example illustrated in FIG. 19, spectral filter 1904 is a 3-element filter having filter coefficients F1, F2 and F3. The scaling can be accomplished by multiplying each filter coefficient by the intensity of the received spectral element.

In step 1808, the scaled spectral filter coefficients are added to a spectral buffer. The spectral buffer is an array. The number of elements in the spectral buffer equals the number of elements in each spectrum.

For performing the summation, filter 1904 is aligned so that the element of the spectral buffer corresponding to the received spectral element is aligned with the center of filter 1904. Thus, at time T1, when spectral element S1 is received, the center of filter 1904, F2, is aligned with spectral buffer element 1902*a*; at time T2, when spectral element S2 is received, the center of filter 1904, F2, is aligned with spectral buffer element 1902*b*, and so on. These steps are illustrated in FIG. 19, wherein the scaling of filter coefficients F1, F2, and F3 and addition to spectral buffer 1902 is illustrated for times, T1, T2, T3, T4 and T5, which, in the present example, is the time required to receive sufficient spectral elements to fill spectral buffer 1902. The resulting scaled sums are also shown in the spectral buffer elements of FIG. 19.

In step 1810, the DAS determines whether the spectral buffer is full, that is, whether the number of spectral elements received and processed is the same as the number of elements in the spectral filter. If not, then the DAS continues the method in step 1802 by waiting for the next spectral element. If the spectral buffer is full, the DAS continues the method in step 1812.

In step 1812, the DAS moves the new spectrum to chromatographic buffer 1906. Chromatographic buffer 1906 contains N-spectra, where N is the number of coefficients in the chromatographic buffer. In the present example, N is 3. Chromatographic buffer 1906 is configured as a first in, last out (FILO) buffer. Consequently, when a new spectrum is added, the oldest spectrum is dropped. When a new spectrum is added in step 1812, the oldest spectrum is discarded. In step 1814, the DAS applies a chromatographic filter 1907 to each row of chromatographic buffer 1906. After application of the filter, central column 1908 corresponds to a single column convolved spectrum of the output convolved matrix. In step 1816, the DAS transfers the convolved spectrum to an apex buffer 1910.

In an embodiment of the present invention, apex buffer 1910 is three spectra in width, that is, apex buffer 1910 comprises three columnar spectra. Each of the spectral columns preferably has the length of a complete spectrum. Apex buffer 1910 is a FILO buffer. Thus, when the new column from chromatographic buffer 1906 is appended to apex buffer 1910 in step 1816, the oldest columnar spectrum is discarded.

Peak detection algorithms as described below can be performed on the central column 1912 of apex buffer 1910. Central column 1912 is used to provide more accurate analysis of peaks and ion parameters by using nearest neighbor values. Analysis of the peaks allows the DAS to extract ion parameters (such as retention time, m/z and intensity) in step 1820 to store in the ion parameter list. Moreover, spectral peak width information can also be obtained by examining points adjacent to the local maxima along the column.

Apex buffer 1910 can also be expanded beyond 3 spectra in width. For example, to measure chromatographic peak width, it would be necessary to expand the apex buffer to include a number of spectra at least equal to the FWHM of the chromatographic peak, for example twice the FWHM of a chromatographic peak.

In a real-time embodiment of the present invention, original spectra need not be recorded. Only the filtered spectra are recorded. Thus, the mass storage requirements for a real time embodiment of the present invention are reduced. Generally, however, additional storage memory, for example, RAM, is required for real-time embodiments of the present invention. For a rank-1 filter-based real time embodiment of the present invention, only a single spectrum buffer is needed. For rank-2 filter-based real time embodiment of the present invention, two spectral buffers are needed, one for the smoothing, and one for the second derivative spectral filters.

Step 4: Peak Detection

The presence of an ion produces a peak having a local maximum of intensity in the output convolved matrix. The detection process of embodiments of the present invention detects such peaks. In one embodiment of the present invention, the detection process identifies those peaks whose maximal intensity satisfy a detection threshold as peaks that correspond to ions. As used herein, satisfaction of a detection threshold is defined as meeting any criterion for overcoming the detection threshold. For example, the criterion could be meeting the detection threshold or meeting or exceeding the detection threshold. In addition in some embodiments of the present invention, the criterion may be falling below a detection threshold or meeting or falling below a detection threshold.

Each local maximum of intensity in the output convolved matrix is a candidate for a peak that corresponds to an ion. As described above, in the absence of detector noise, every local maximum would be deemed to correspond to an ion. However, in the presence of noise, some local maxima (especially low-amplitude local maxima) are due only to the noise, and do not represent genuine peaks corresponding to detected ions. Consequently, it is important to set the detection threshold to make it highly unlikely that a local maximum that satisfies the detection threshold is due to noise.

Each ion produces a unique apex or maximum of intensity in the output convolved matrix. The characteristics of these unique maxima in the output convolved matrix provide information on the number and properties of the ions present in the sample. These characteristics include location, width and other properties of the peaks. In one embodiment of the present invention, all local maxima in the output convolved matrix are identified. Subsequent processing eliminates those determined not to be associated with ions.

According to embodiments of the present invention, a local maximum of intensity is deemed to correspond to a detected ion only if the value of the local maximum satisfies a detection threshold. The detection threshold itself is an intensity against which local maxima of intensities are compared. The value of the detection threshold can be obtained by subjective or objective means. Effectively, the detection threshold divides the distribution of true peaks into two classes: those that satisfy the detection threshold and those that do not satisfy the detection threshold. Peaks that do not satisfy the detection threshold are ignored. Consequently, true peaks that do not satisfy the detection threshold are ignored. Such ignored true peaks are referred to as false negatives.

The threshold also divides the distribution of noise peaks into two classes: those which satisfy the detection threshold and those which do not satisfy the detection threshold. Any noise peaks that satisfy the detection threshold are deemed ions. Noise peaks that are deemed ions are referred to as false positives.

In embodiments of the present invention, the detection threshold typically is set to achieve a desired false positive rate, which is usually low. That is, the detection threshold is set so that the probability that a noise peak will satisfy the detection threshold in a given experiment is unlikely.

To obtain a lower false positive rate, the detection threshold is set to a higher value. Setting the detection threshold to a higher value to lower the false positive rate has the undesirable effect of raising the false negative rate, i.e., the probability that low-amplitude, true peaks corresponding to ions will not be detected. Thus, the detection threshold is set with these competing factors in mind.

The detection threshold can be determined subjectively or objectively. The goal of any thresholding method, whether subjective or objective is to determine a detection threshold to use to edit the ion list. All peaks whose intensities do not satisfy the detection threshold are considered noise. These "noise" peaks are rejected and not included in further analysis.

A subjective method for setting the detection threshold is to draw a line that is close to the maximum of the observed noise. Any local maxima satisfying the detection threshold are considered peaks corresponding to ions. And any local maxima not satisfying the detection threshold are considered noise. Although the subjective method for determining threshold can be used, objective techniques are preferred.

One objective method for selecting the detection threshold according to embodiments of the present invention uses a histogram of the output convolved matrix data. FIG. 20 is a flow chart for a method for objectively determining a detection threshold according to an embodiment of the present invention. The method is also graphically illustrated in FIG. 7. The method proceeds according to the following steps:

STEP 2002: Sort the intensities of all positive local maxima found in the output convolved matrix in ascending order
STEP 2004: Determine standard deviation of intensity data in output convolved data matrix as the intensity that is at the 35.1 percentile in the list.
STEP 2006: Determine the detection threshold based on a multiple of the standard deviation.
STEP 2008: Generate edited ion list or ion parameter list using peaks satisfying the detection threshold.

The above method is applicable when most of the local maxma are due to Gaussian noise. For example, if there 1000 intensities, then Step 2004 would determine that the 351th intensity represents a Gaussian standard deviation. If the distribution of maximal intensities were due only to Gaussian noise processes, then local maxima whose values exceeded the 351st intensity would occur at frequency that is predicted by a Gaussian noise distribution.

The detection threshold is then a multiple of the 351th intensity. As an example, consider two detection thresholds. One corresponds to 2 standard deviations. One corresponds to 4 standard deviations. The 2-deviation threshold yields few false negatives, but a large number of false positives. From the properties of a Gaussian noise distribution a 2-standard deviation threshold means that about 5% of peaks would be falsely identified as ions. The 4-deviation threshold yields more false negative, but significantly fewer false positives. From the properties of a Gaussian noise distribution a 4-standard deviation threshold means that about 0.01% of peaks would be falsely identified as ions.

Rather than sorting the list of intensities of all local maxima, a histogram display can be used where the number of intensities per interval of intensities are recorded. A histogram is obtained by selecting a series of uniformly spaced intensity values, each pair of values defining an interval, and counting the number of maximal intensities that fall within each bin. The histogram is the number of intensities per bin versus the mean intensity value defining each bin. The histogram provides a graphical method for determining the standard deviation of the distributions of intensities.

A variation of the empirical method uses the relationship between the standard deviation $\sigma$ of the convolved output noise and the standard deviation $\sigma_o$ of the input noise to set the detection threshold. From the filter analysis above, this relationship is given as $$\sigma = \sigma_o \sqrt{\sum_{j=-l}^{l} \sum_{i=-h}^{h} F_{i,j}^2}$$

assuming that the input noise is uncorrelated Gaussian deviates. The input noise $\sigma_o$ can be measured from the input LCL/MS data matrix as the standard deviation of the background noise. A region of the LC/MS containing only background noise can be obtained from a blank injection, that is LC/MS data is obtained from a separation with no sample injected.

Thus, the standard deviation of the output can be inferred using only the values of the filter coefficients $F_{i,j}$ and the measured background noise $\sigma_o$. The detection threshold can then be set based upon the derived output noise standard deviation $\sigma$.

Step 5: Peak Parameter Extraction

After identifying those local maxima that are peaks corresponding to ions, parameters for each peak are estimated. In one embodiment of the present invention the parameters that are estimated are the retention time, mass-to-charge ratio, and intensity. Additional parameters such as chromatographic peak width (FWHM) and mass-to-charge peak width (FWHM) can also be estimated.

The parameters of each identified ion are obtained from the characteristics of the local maximum of the detected peaks in the output convolved data matrix. In an embodiment of the present invention, these parameters are determined as follows: (1) the ion's retention time is the time of the (filtered) scan containing the (filtered) maximal element (2) The ion's m/z is the m/z of the (filtered) channel containing the (filtered) maximal element; (3) The ion's intensity is the intensity of the (filtered) maximal element itself.

The width of a peak in the spectral or chromatographic directions can be determined by measuring the distance between the locations of the nearest zero crossing points that straddle the peak or by measuring the distance between the nearest minima that straddle a peak. Such peak widths can be used to confirm that a peak is resolved from its neighbors. Other information can be gathered by considering peak width. For example, an unexpectedly large value for a peak width may indicate coincident peaks. Consequently, the locations of zero crossings or local minima can be used as inputs to estimate the effect of interfering coincidence or to modify parameter values stored in the ion parameter list.

The parameters determined by analyzing the peaks can be further optimized by considering the neighboring elements. Because the elements of the convolved matrix represent a digital sample of data, the true apex of a peak in the chromatographic (time) dimension may not coincide exactly with a sample time and the true apex of a peak in the spectral (mass-to-charge ratio) dimension may not coincide exactly with a mass-to-charge ratio channel. As a result, typically the actual maximum of the signal in the time and mass-to-charge ratio dimensions is offset from the available sampled values by a fraction of the sample period or the mass-to-charge ratio channel interval. These fractional offsets can be estimated from the values of the matrix elements surrounding the element having the local maximum corresponding to the peak using interpolation, such as curve fitting techniques.

For example, a technique for estimating the fractional offset of the true apex from an element of the output convolved matrix containing a local maxima corresponding to an ion in the two-dimensional context is to fit a two-dimensional shape to the elements of the data matrix containing a local maxima and its nearest neighbors. In embodiments of the present invention, a two-dimensional parabolic shape is used because it is a good approximation to the shape of the convolved peak near its apex. For example, a parabolic shape can be fit to a nine element matrix comprising the peak and its 8 nearest neighbors. Other fits can be used for this interpolation within the scope and spirit of the present invention.

Using the parabolic fit an interpolated value of the peak apex is calculated from which to determine the ion parameters. The interpolated value provides more accurate estimates of retention time, m/z and intensity than those obtained by reading values of scan times and spectral channels. The value of the parabola at the maximum, and its interpolated time and m/z values corresponding to that maximum, are the estimates of ion intensity, retention time and m/z.

The interpolated location in the row direction of the maximum of the two-dimensional parabolic fit is an optimal estimate of retention time. The interpolated location in the column direction of the maximum of the two-dimensional parabolic fit gives an optimum estimate of mass-to-charge ratio. The interpolated height of the apex above baseline gives an optimum estimate (scaled by filter factors) of ion intensity or concentration.

Embodiments of the present invention can also be configured to extract peak parameters from the results of intermediate convolved matrices. For example, the methods discussed above for locating a single peak corresponding to a detected ion can also be used to locate peaks in each row or column of the matrix. These peaks may be useful to store a spectra or chromatograms at known times or mass values.

For example, spectra or chromatograms obtained from the second derivative filters can be obtained for each row and column from the intermediate convolved matrices described above. These intermediate results can be examined for local maxima as well. These maxima are, in effect smoothed versions of the chromatograms and spectra. Local maxima can be extracted and saved, giving additional detail as to the spectral content of the sample at a particular time or time range, or the chromatographic content at a typical mass or mass range.

Measurement Error

Because each ion parameter measurement produced by embodiments of the present invention is an estimate, there is a measurement error associated with each such measurement. These associated measurement errors can be statistically estimated.

Two distinct factors contribute to the measurement errors. One factor is a systematic or calibration error. For example, if the mass spectrometer m/z axis is not perfectly calibrated, then any given m/z value contains an offset. Systematic errors typically remain constant. For example, calibration error remains essentially constant over the entire m/z range. Such an error is independent of signal-to-noise or amplitude of a particular ion. Similarly, in the case of mass-to-charge ratio, the error is independent of the peak width in the spectral direction.

The second factor contributing to measurement error is the irreducible statistical error associated with each measurement. This error arises due to thermal or shot-noise related effects. The magnitude or variance of this error for a given ion depends on the ion's peak width and intensity. Statistical errors measure reproducibility and therefore are independent of calibration error. Another term for the statistical error is precision.

The statistical error associated with each measurement can in principle be estimated from the fundamental operating parameters of the instrument on which the measurement is made. For example in a mass spectrometer, these operating parameters typically include the ionization and transfer efficiency of the instrument coupled with the efficiency of the micro-channel counting plate (MCP). Together, these operating parameters determine the counts associated with an ion. The counts determine the statistical error associated with any measurement using the mass spectrometer. For example, the statistical error associated with the measurements discussed above typically follows a Poisson distribution. A numerical value for each error can be derived from counting statistics via the theory of error propagation. See example, in P. R. BEVINGTON, DATA REDUCTION AND ERROR ANALYSIS FOR THE PHYSICAL SCIENCES at 58-64 (McGRAW-HILL 1969)

In general, statistical errors also can be inferred directly from the data. One way to infer statistical errors directly from the data is to investigate the reproducibility of the measurements. For example, replicate injections of the same mixture can establish the statistical reproducibility of m/z values for the same molecules. Differences in the m/z values through the injections are likely due to statistical errors.

In the case of errors associated with retention time measurements, statistical reproducibility is more difficult to achieve because systematic errors arising from replicate injections tend to mask the statistical error. A technique to overcome this difficulty is to examine ions at different m/z values that were produced from a common parent molecule. Ions that originate from a common molecule would be expected to have identical intrinsic retention times. As a result, any difference between measurements of the retention times of molecules originating from a common parent is likely due to statistical errors associated with the fundamental detector noise associated with measurements of peak properties.

Each measurement made and stored using an embodiment of the present invention can be accompanied by estimates of its associated statistical and systematic errors. Though these errors apply to the parameter estimates for each detected ion, their values can be inferred generally by analyzing sets of ions. After a suitable error analysis, the errors associated with each measurement for a detected ion can be included in each row of the table corresponding to the detected ion measurement. In such an embodiment of the present invention, each row of the table can have fifteen measurements associated with each ion. These measurements are the five measurements for the detected ion corresponding to the row and their associated statistical and systematic errors, which are retention time, mass-to-charge ratio, intensity, spectral FWHM, and chromatographic FWHM.

As described above, the statistical component of measurement error, or precision, in retention time and m/z depends on the respective peak widths and intensities. For a peak that has a high SNR, the precision can be substantially less than the FWHM of the respective peak widths. For example, for a peak that has a FWHM of 20 milli-amu and high SNR, the precision can be less than 1 milli-amu. For a peak that is barely detectable above the noise, the precision can be 20 milli-amu. For purposes of the present discussion of statistical error, the FWHM is considered to be the FWHM of the peak in the LC/MS chromatogram prior to convolution.

Precision is proportional to the peak width and inversely proportional to peak amplitude. Generally, the relationship between precision, peak width and peak amplitude can be expressed as:

$$\sigma_m = k \frac{w_m}{h_p}.$$

In this relationship, $\sigma_m$ is the precision of the measurement of m/z (expressed as a standard error), $w_m$ is the width of the peak (expressed in milli-amu at the FWHM), $h_p$, is the intensity of the peak (expressed as a post-filtered, signal to noise ratio) and k is a dimensionless constant on the order of unity. The exact value for k depends on the filter method used. This expression shows that $\sigma_m$ is less than $w_m$. Thus, the present invention allows estimates of m/z for a detected ion to be made with a precision that is less than the FWHM of the m/z peak width as measured in the original LC/MS data.

Similar considerations apply with respect to the measurement of retention time. The precision to which retention time of a peak can be measured depends on the combination of peak width and signal intensity. If the FWHM max of the peak is 0.5 minutes, the retention time can be measured to a precision, described by a standard error, of 0.05 minutes (3 seconds). Using the present invention, estimates of retention time for a detected ion can be made with a precision that is less than the FWHM of the retention time peak width as measure in the original LC/MS data.

Step 6: Store Extracted Parameters

As described above, one output of embodiments of the present invention is a table or list of parameters corresponding to detected ions. This ion parameter table, or list has a row corresponding to each detected ion, wherein each row comprises one or more ion parameters and, if desired, their associated error parameters. In one embodiment of the present invention, each row in the ion parameter table has three such parameters: retention time, mass-to-charge ratio and intensity. Additional ion parameters and associated errors can be stored for each detected ion represented in the list. For example, a detected ion's peak width as measured by its FWHM or its zero-crossing width in the chromatographic and/or spectral directions also can be determined and stored.

The zero-crossing width is applicable when filtering is performed with a second derivative filter. The zero value of the second derivative occurs at inflection points of a peak on both the up-slope and down-slope sides of the peak. For a Guassian peak profile, the inflection points occur at +/1 standard deviation distance from the peak apex. Thus the width as measured by the inflection points correspond to the 2-standard deviation width of the peak. Thus the zero-crossing width is a height-independent measure of peak width corresponding to approximately 2 standard deviations. In an embodiment of the present invention, the number of rows in the table corresponds to the number of ions detected.

The present invention also provides a data compression benefit. This is because the computer memory needed to store the information contained in the ion parameter table is significantly less than the memory needed to store initially generated original LC/MS data. For example, a typical injection that contains 3600 spectra (for example, spectra collected once per second for an hour), with 400,000 resolution elements in each spectrum (for example, 20,000:1 MS resolution, from 50 to 2,000 amu) requires in excess of several gigabytes of memory to store the LC/MS data matrix of intensities.

In a complex sample, using embodiments of the present invention, on the order of 100,000 ions can be detected. These detected ions are represented by a table having 100,000 rows, each row comprising ion parameters corresponding to a detected ion. The amount of computer storage required to store the desired parameters for each detected ion is typically less than 100 megabytes. This storage amount represents only a small fraction of the memory needed to store the initially generated data. The ion parameter data stored in the ion parameter table can be accessed and extracted for further processing. Other methods for storing the data can be employed in embodiments of the present invention.

Not only are storage requirements significantly reduced, but computational efficiency of post-processing LC/MS data is significantly improved if such analysis is performed using the ion parameter list rather than the originally produced LC/MS data. This is due to the significant reduction in number of data points that need to be processed.

Step 7: Simplify Spectra and Chromatograms

The resulting ion list or table can be interrogated to form novel and useful spectra. For example, as described above, selection of ions from the table based upon the enhanced estimates of retention times produces spectra of greatly reduced complexity. Alternatively, selection of ions from the table based upon the enhanced estimates of m/z values produces chromatograms of greatly reduced complexity. As described in more detail below, for example, a retention time window can be used to exclude ions unrelated to the species of interest. Retention-time selected spectra simplify the interpretation of mass spectra of molecular species, such as proteins, peptides and their fragmentation products, that induce multiple ions in a spectrum. Similarly an m/z window can be defined to distinguish ions having the same or similar m/z values.

Using the concept of a retention window, simplified spectra from an LC/MS chromatogram can be obtained. The width of the window can be chosen to be no larger than the FWHM of the chromatographic peak. In some cases, smaller windows such as one tenth the FWHM of a peak are selected. The retention-time window is defined by selecting a particular retention time, which is generally associated with the apex of a peak of interest, and then choosing a range of values about the chosen particular retention time For example, the ion having the highest intensity value can be selected and retention time recorded. A retention time window is selected around the recorded retention time. Then, the retention times stored in the ion parameter table are examined. Only those ions having retention times falling within the retention time window are selected for inclusion in the spectrum. For a peak having a FWHM of 30 seconds, a useful value of retention time window can be as large as +/−15 seconds or as small as +/−1.5 seconds.

The retention time window can be specified to select ions that elute nearly simultaneously, and are thus candidates for being related. Such a retention time window excludes unrelated molecules. Thus, the spectra obtained from the peak list using the retention window contains only the ions corresponding to the species of interest thereby, significantly simplifying the produced spectrum. This is a large improvement over spectra generated by conventional techniques, which typically contain ions unrelated to the species of interest.

Using the ion parameter table also provides a technique for analyzing chromatographic peak purity. Peak purity refers to whether a peak is due to a single ion or the result of co-eluting ions. For example, by consulting the ion parameter list generated by embodiments of the present invention an analyst can determine how many compounds or ions elute within the time of a principle peak of interest. A method for providing a measure or metric of peak purity is described with reference to FIG. 21.

In step 2102, a retention time window is chosen. The retention time window corresponds to the lift off and touch down of the peak corresponding to the ion of interest. In step 2104, the ion parameter table is interrogated to identify all ions eluting within the chosen retention time window. In step 2106, the intensities of the identified ions (including the ion of interest) are summed. In step 2108, a peak purity metric is calculated. The peak purity metric can be defined in a number of ways. In one embodiment of the present invention, the peak purity metric is defined as:

purity=100*(intensity of peak of interest)/(sum of intensity of all peaks in retention window).

Alternatively, in another embodiment of the present invention, peak purity is defined as:

purity=100*(intensity of most intense)/(sum of intensity of all peaks in retention window).

In both definitions of peak purity, the peak purity is expressed as a percent value.

The spectra simplifying properties of the present invention can also be used to study biological samples more easily. Biological samples are an important class of mixtures commonly analyzed using LC/MS methods. Biological samples generally comprise complex molecules. A characteristic of such complex molecules is that a singular molecular species may produce several ions. Peptides occur naturally at different isotopic states. Thus, a peptide that appears at a given charge will appear at several values of m/z, each corresponding to a different isotopic state of that peptide. With sufficient resolution, the mass spectrum of a peptide exhibits a characteristic ion cluster.

Proteins, which typically have high mass, are ionized into different charge states. Although isotopic variation in proteins may not be resolved by a mass spectrometer, ions that appear in different charge states generally can be resolved. Such ions produce a characteristic pattern that can be used to help identify the protein. The methods of the present invention would then allow one to associate those ions from a common protein because they have a common retention time. These ions then form a simplified spectrum that can be analyzed by for example, the method disclosed in U.S. Pat. No. 5,130,538 to Fenn et al.

Mass spectrometers measure only the ratio of mass-to-charge, not mass by itself. It is possible however, to infer the charge state of molecules such as peptides and protein from the pattern of ions they produce. Using this inferred charge state, the mass of the molecule can be estimated. For example, if a protein occurs at multiple charge states, then it is possible from the spacing of m/z values to infer the charge, to calculate the mass of each ion knowing the charge and ultimately to estimate the mass of the uncharged parent. Similarly, for peptides, where the m/z charges are due to charge in the isotopic value for a particular mass m, it is possible to infer the charge from the spacing between adjoining ions.

There are a number of well-known techniques that use the m/z values from ions to infer the charge and parent mass. An exemplary such technique is described in U.S. Pat. No. 5,130, 538, which is hereby incorporated by reference herein in its entirety. A requirement for each of these techniques is selection of the correct ions and the use of accurate values for m/z. Ions represented in the detected ion parameter table provide high precision values that can be used as inputs to these techniques to produce results with enhanced precision.

In addition, several of the cited methods attempt to reduce the complexity of spectra by distinguishing between ions that may appear in a spectrum. Generally, these techniques involve selecting a spectrum centered on a prominent peak or combing spectra associated with a single peak, to obtain a single extracted MS spectra. If that peak were from a molecule that produced multiple, time-coincident ions, the spectra would contain all those ions including ions from unrelated species.

These unrelated species can be from ions that elute at the exact same retention time as the species of interest or, more commonly, the unrelated species are from ions that elute at different retention times. However, if these different retention times are within a window of approximately the FWHM of the chromatographic peak width, the ions from the front or tails of these peaks are likely to appear in the spectrum. The appearance of the peaks associated with unrelated species requires subsequent processing to detect and remove them. In some instances where they coincide, they may be biasing measurements.

Figure 22A:
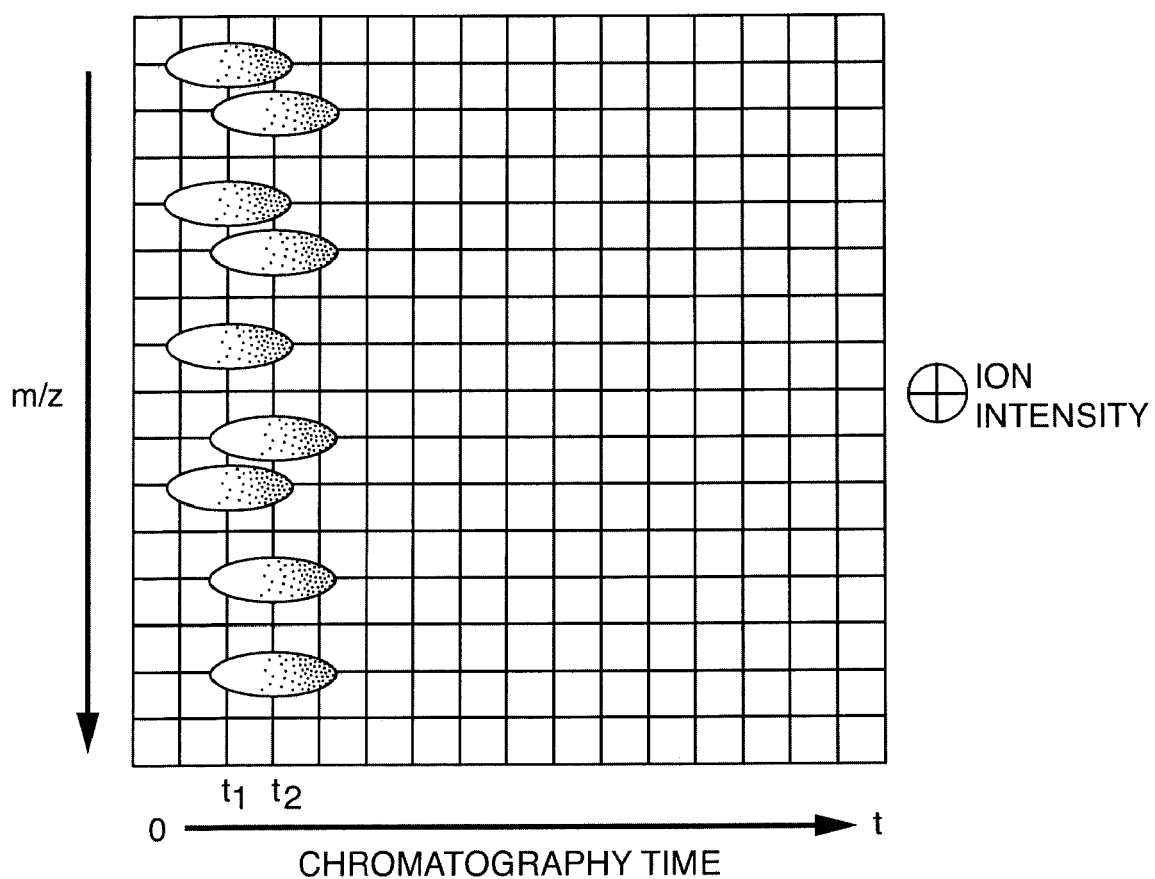
FIG. 22A illustrates an exemplary LC/MS data matrix resulting from two parent molecules and the resulting multiplicity of molecules.
Figure 22B:
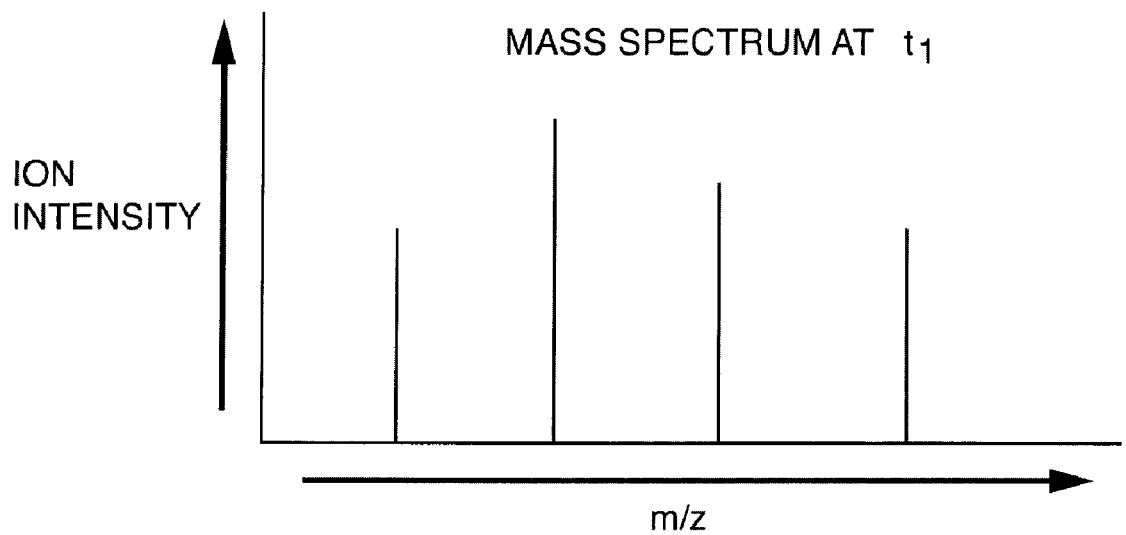
FIG. 22B illustrates an exemplary complex spectrum corresponding to the data of FIG. 22A at a time t1.
Figure 22C:
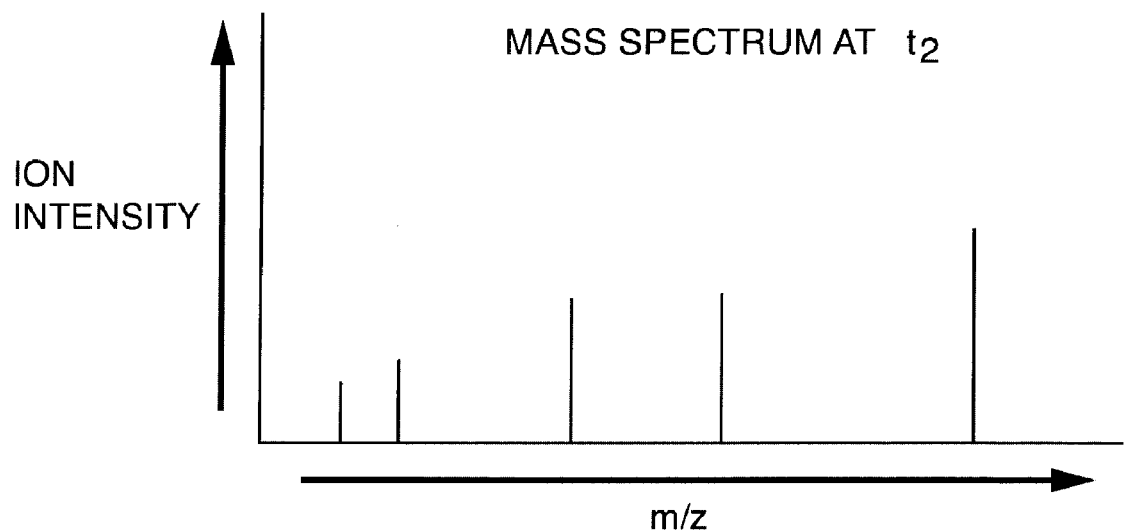
FIG. 22C illustrates an exemplary complex spectrum corresponding to the data of FIG. 22A at a time t2.

FIG. 22A illustrates an exemplary LC/MS data matrix that results from two parent molecules, and the resulting multiplicity of ions. In this example a species elutes at time t1 producing 4 ions and another species elutes at time t2 producing 5 ions in the LC/MS data matrix. Even though there are two distrinct species, if a spectrum were to be extracted at time t1 or time t2, the result spectrum would contain nine peaks one from each of the nine ions. However the present invention would obtain 9 accurate retentions times (as well as m/z and intensities) for each of these 9 ions. If a spectrum were then constructed only of ions that had retention times substantially equal to t1, then only four ions would be present. This simplified spectrum appears in FIG. 22B. Similarly, tf a spectrum were then constructed only of ions that had retention times substantially equal to t2, then only five ions would be present. This simplified spectrum appears in FIG. 22C.

Applications

As a sample is collected with an LC/MS system, a plurality of spectra is typically collected across the chromatographic peak in order for the retention time to be accurately inferred. For example, in embodiments of the present invention 5 spectra per FWHM are collected.

It is possible to alternate the configuration of an LC/MS system on a spectrum by spectrum basis. For example, all even spectra can be collected in one mode and all odd interleaving spectra can be collected with the MS configured to operate in a different mode. An exemplary dual mode collection operation can be employed in LC/MS alternating with LC/MSE where in one mode (LC/MS) unfragmented ions are collected and in the second mode (LC/MSE), fragments of the unfragmented ions collected in the first mode are collected. The modes are distinguished by the level of a voltage applied to ions as they traverse a collisional cell. In the first mode the voltage is low, and in the second mode, the voltage is elevated. (Bateman et al.)

In such a system, the fragments or ions collected with the system in one mode appear with a chromatographic profile having the same retention time as the unmodified ions. This is because the unfragmented and fragmented ions are common to the same molecular species, so the elution profile of the molecule is imprinted upon all unfragmented and fragmented ions that derive from it. These elution profiles are substantially in time alignment because the extra time required to switch between modes in online MS is short as compared to the peak width or FWHM of a chromatographic peak. For example, the transit time of a molecule in an MS is typically on the order of milli- or micro-seconds, while the width of a chromatographic peak is typically on the order of seconds or minutes. Thus, in particular, the retention times of the unfragmented and fragmented ions are substantially identical. Moreover, the FWHM of the respective peaks will be the same, and further, the chromatographic profiles of the respective peaks will be substantially the same.

The spectra collected in the two modes of operation can be divided into two independent data matrices. The operations of convolution, apex detection, parameter estimation and thresholding described above can be applied independently to both. Although such analysis results in two lists of ions, the ions appearing in the lists bear a relationship to one another. For example, an intense ion having a high intensity that appears in the list of ions corresponding to one mode of operation may have counterpart in the list of modified ions collected according to the other mode of operation. In such a case, the ions will typically have a common retention time. To associate such related ions with one another for analysis, a window restricting retention time as described above can be applied to ions found in both data matrices. The result of applying such a window is to identify ions in the two lists having a common retention time and are therefore likely to be related.

Even though the retention times of these related ions are identical, the effects of detector noise will result in the measured values of retention time of these ions to differ somewhat. This difference is a manifestation of statistical error and measures the precision of the measurement of retention time of an ion. In the present invention, the difference in estimate retention times of ions will be less than the FWHM of the chromatographic peak width. For example if the FWHM of a peak is 30 seconds, the variation in retention times between ions will be less than 15 seconds for low-intensity peaks, and less then 1.5 seconds for high-intensity peaks. The window widths used to collect ions of the same molecule (and to reject unrelated ions) can the be as large as +/−15 seconds or as small as +/−1.5 seconds in this example.

Figure 23A:
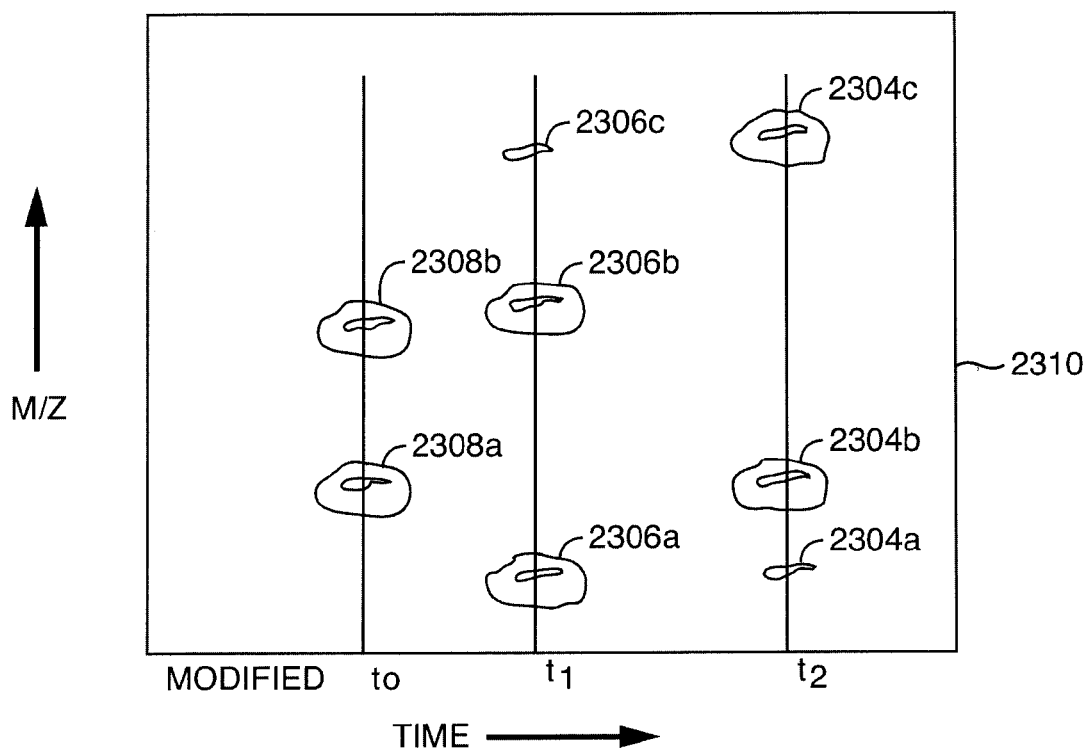
FIG. 23 is a graphical chart illustrating how related ions can be identified in the unmodified and modified ion lists generated by an embodiment of the present invention.
Figure 23B:
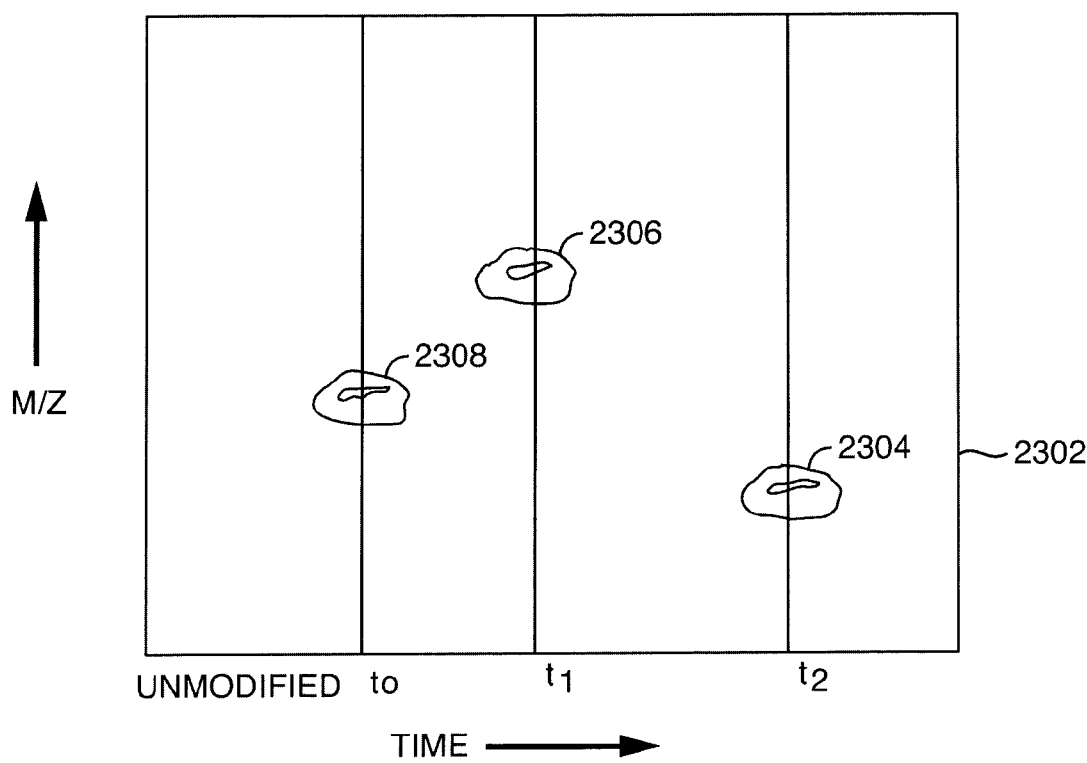

FIG. 23 is a graphical chart illustrating how related ions can be identified in the unmodified and modified ion lists generated by an embodiment of the present invention. Data matrix 2302 shows three precursor ions 2304, 2306 and 2308 that are detected in spectra resulting from an unmodified MS experiment. Data matrix 2310 shows eight ions that result from an experiment after the MS is modified for example as described above to cause fragmentation. Ions in data matrix 2302 that are related to those in the data matrix 2310 appear at the same retention time, as indicated by the three vertical lines labeled t0, t1, and t2. For example, ions 2308a and 2308b in data matrix 2310 are related to ion 2308 in data matrix 2302. Ions 2306a, 2306b, and 2306c in data matrix 2310 are related to ion 2306 in data matrix 2302. Ions 2304a, 2304b and 2304c in data matrix 2310 are related to ion 2304 in data matrix 2302. These relationships can be identified by retention time windows with appropriate widths centered at time t0, t1, and t2 respectively.

The ion parameter list can be used for a variety of analyses. One such analysis involves fingerprinting or mapping. There are numerous examples of mixtures that are, on the whole well characterized, and have essentially the same composition, and whose components exist in the same relative amounts. Biological examples include the end products of metabolism such as urine, cerebrospinal fluid, and tears. Other examples are the protein contents of cell populations found in tissues and blood. Other examples are the enzymatic digests of protein contents of cell populations found in tissues and blood. These digests contain mixtures peptides that can by analyze by dual mode LC/MS and LC/MSE. Examples in industry include perfumes, fragrances, flavors, fuel analysis of gasoline or oils. Environmental examples include pesticides, fuel and herbicides, and contamination of water and soil.

Abnormalities from what would be expected to be observed in these fluids include xenobiotics in the case of products of metabolism that result from ingestion or injection of drugs or drug substances; evidence of drugs of abuse in metabolic fluids; adulteration in products such as juices, flavors, and fragrances; or in fuel analysis. The ion parameter list generated according to embodiments of the present invention can be used as an input to methods known in the art for fingerprint or multi-variate analysis. Software analysis packages such as SIMCA (Umetrics, Sweden), or Pirouette (Infometrix, Woodenville, Wash., USA) can be configured to use fingerprint or multi-variate techniques to detect such abnormalities, by identifying changes in ions between sample populations. These analyses can determine the normal distribution of entities in a mixture, and then identify those samples that deviation from the norm.

The synthesis of a compound may produce the desired compound together with additional molecular entities. These additional molecular entities characterize the synthetic route. The ion parameter list in effect becomes a fingerprint that can be used to characterize the synthetic route of the synthesis of a compound.

Another important application to which the present invention is applicable is biomarker discovery. The discovery of molecules whose change in concentration correlates uniquely with a disease condition or with the action of a drug is fundamental to the detection of disease or to the processes of drug discovery. Biomarker molecules can occur in cell populations or in the products of metabolism or in fluids such as blood and serum. Comparison of the ion parameter lists generated for control and disease or dosed states using well known methods can be used to identify molecules that are markers for the disease or for the action of a drug.

N-Dimensional Data and LC/IMS/MS

Some embodiments of the invention involve higher dimensional data than that obtained from LC/MS instruments. Some of these embodiments involve LC/IMS/MS instruments. Although the following description is directed primarily at LC/IMS/MS data, one of skill will understand that the principles described herein have broader applicability to a variety of instruments that provide three- and higher-dimensional data.

Some of these embodiments include an LC module, an IMS module and a TOF-MS module. An example of such an instrument, with which some embodiments of the invention are suitably implemented, is described in US Patent Publication 2003/01084 to Bateman et al., published on Jan. 2, 2003.

First, for a broader context of some aspects of the invention, the collection of data of different numbers of dimensions is described. For a single-channel detector, as found, for example, in a LC-only or MS-only instrument, the one-dimensional data is typically displayed in a two-dimensional plot. One must then locate all peaks in the plot.

In the case of LC, typical detectors implement ultraviolet/visible (UV/Vis) light absorbance detection. The peak parameters are the retention time and absorbance of the peak as it elutes from the column.

In the case of MS, as performed, for example, with a quadrupole- or TOF-based MS, electromagnetic forces serve to separate ions of different m/z ratio, and a detector provides a value of ion intensity as a function of the m/z ratio. A routine is required to locate the peaks in the two-dimensional plot of the intensity versus m/z data. In combined LC/MS, peaks must be located, i.e., distinguished from artifacts in the data plotted in three dimensions (ion intensity versus retention time and m/z.)

In some LC/IMS/MS-related embodiments, described below, three separation-related dimensions are associated with ion-intensity values. The three dimensions of separation—liquid chromatography, followed by ion mobility, followed by mass spectrometry—measure three corresponding properties of the ions: retention time, ion mobility, and mass-to-charge ratio. The MS module locates an ion in its m/z value in association with the ion's peak. The peak is associated with, for example, the integrated number of ion counts of the ion's peak, as measured by a micro-channel plate.

Table 3 provides a summary of the different numbers of dimensions of data provided by some embodiments of the invention. The first column lists some specific analytical techniques and a more general reference to any technique having N dimensions of data associated with N separations. N is optionally equal to as much as three or more. The second column lists the number of dimensions of a convolution filter that is utilized, in accordance with some embodiments of the invention, to reduce artifacts and help distinguish overlapping peaks. In some preferred implementations, the number of dimensions of a convolution filter matches the number of separations.

For definitional purposes, if one chooses to treat ion intensity as a dimension of data, in addition to the dimensions of separation, the data are optionally then referred to as having a dimension one greater than the number of separation dimensions.

After convolution, peaks associated with local maxima are located in the convolved data. For example, a local maximum in a three-dimensional space is suitably defined as the data point (also referred to herein as data element) that has a value greater than all of its neighbors. For example, an element in a three-dimensional separation space has 3×3×3−1=26 neighbors. So, locating a local maximum generally requires a comparison of a central element to 26 neighboring elements.

The third column of Table 3 lists the number of comparisons to be made to establish that a point is a local maximum. The remaining columns list the separation dimensions. The local maximum identifies the apex of the peak. Each apex corresponds to an ion. The remainder of this Detailed Description will focus on LC/IMS/MS and greater dimensions of separation.

TABLE 3

| Analytic Method | Convolution Filter applied to data | Comparisons to find local maximum | Dimension of data Axis-1 | Axis-2 | Axis-3 |
|---|---|---|---|---|---|
| LC | 1-D | 3 − 1 = 2 | LC-time | | |
| MS | 1-D | 3 − 1 = 2 | m/z | | |
| LC/MS | 2-D | $3^2 − 1 = 8$ | LC-time | m/z | |
| LC/IMS/MS | 3-D | $3^3 − 1 = 26$ | LC-time | ion mobility | m/z |
| N separations | N-D | $3^N − 1$ | N axes of separation | | |

Figure 24:
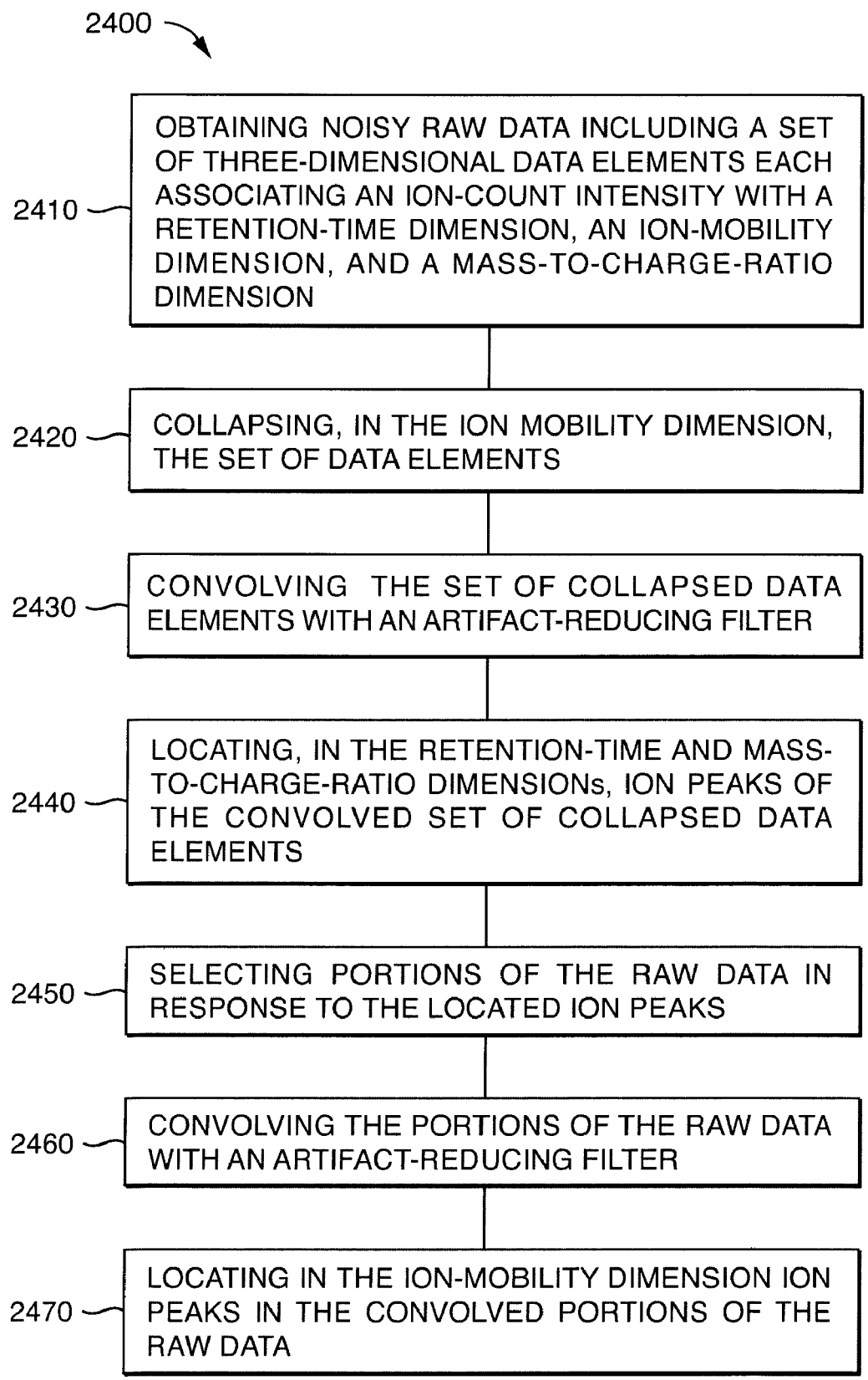
FIG. 24 is a flow diagram of a method of analysis, in accordance with one embodiment of the invention.

FIG. 24 is a flow diagram of a method 2400 of LC/IMS/MS analysis, according to one illustrative embodiment of the invention. The method 2400 includes obtaining 2410 noisy raw data from a sample. The data includes a set of three-dimensional data elements, which each associate an ion-count intensity with a retention-time dimension, an ion-mobility dimension, and a mass-to-charge-ratio dimension. The method 2400 further includes: collapsing 2420, in the ion mobility dimension, the set of data elements to obtain a set of collapsed data elements, which each associate a combined ion-count intensity with the retention-time and mass-to-charge-ratio dimensions; and convolving 2430 the set of collapsed data elements with an artifact-reducing filter that is associated, for example, with a two-dimensional matrix. The method 2400 further includes: locating 2440, in the retention-time and mass-to-charge-ratio dimensions, ion peaks of the convolved set of data elements; and, in response to the located ion peaks, selecting 2450 one or more portions of the noisy raw for further analysis. The method 2400 further includes convolving 2460 the selected portions of the noisy raw data with an artifact-reducing filter that is associated, for example, with a three-dimensional matrix; and locating 2470, in retention-time, ion mobility and mass-to-charge-ratio dimensions, ion peaks in the convolved raw data.

The one or more portions of the raw data selected 2450 for further analysis are selected in response to the located 2440 ion peaks of the convolved set of collapsed data elements. The locations, in the retention-time and mass-to-charge-ratio dimensions, of the ion peaks of the convolved collapsed set of data elements indicate locations, in the retention-time and mass-to-charge-ratio dimensions, of interest in the raw data.

Thus, suitably, the portions selected for further analysis include the full ion-mobility dimension of the raw data, but only restricted regions of the retention-time and mass-to-charge-ratio dimensions of the raw data. These restricted regions include the locations indicated by the convolved collapsed set of data elements. The portions of the raw data are then selected, for example, to be substantially centered on the located ion peaks. Thus, one avoids inefficient analysis of portions of data space that do not contain meaningful data or data of interest. Moreover, the size of the selected portions is optionally chosen in response to a peak width, as observed or predetermined. Preferably, the size of the selected portion, in each dimension, is greater than the peak width, in that dimension.

As mentioned, convolving 2460 entails a three-dimensional convolution of the raw data. For peak-information determination, local maxima are located 2440, optionally, by a search in three dimensions (retention time, ion mobility, and ion m/z); the location of a local maximum associates the three separation-related ion properties—retention time, mobility, and m/z—with an ion's intensity (corresponding to a number of ions detected via MS.) The value of the apex of a peak provides the integrated ion intensity over a whole ion peak, if a convolution filter is appropriately normalized.

Next referring to Table 4, the method 2400 exploits the different levels of resolution of the raw data in the three different dimensions (relatively high-resolution in m/z, relatively poor resolution in ion mobility, and intermediate in retention time.) Table 4 illustrates these differences in resolution. For the three dimensions, Table 4 lists a typical measurement range, sampling period, number of elements (i.e., range divided by sampling period,) peak full-width half maximum (in terms of time,) peak full-width half maximum (in terms of data point elements,) and resolution (in terms of number of resolvable peaks.)

TABLE 4

| Separation Dimension | Range | Sampling period | Number of Array Elements | Peak FWHM | Peak FWHM | Resolution |
|---|---|---|---|---|---|---|
| m/z | 75 μsec | 0.5 ns | 150,000 | 4 ns | 8 elem. | 18,000 |
| Retention | 100 min | 4 sec | 1500 | 30 sec | 7.5 elem | 200 |
| Mobility | 20 ms | 0.1 ms | 200 | 0.7 ms | 7 elem | 30 |

The MS resolution of 18,000 corresponds to 150,000 channels of intensities, with a peak width (FWHM) of 8 channels. The second highest resolution is the chromatographic dimension, with a 100 minute separation and a peak width of 30 seconds (corresponding to 7.5 scans). The lowest resolution is given by ion mobility. Assuming the illustrated example of a FWHM of 7 elements, the IMS resolution is 30 peaks for a 200 channel spectrum. This idealized example ignores the typical variation of peak width with mass and mobility.

In more detail, the method 2400 is optionally implemented as follows. Raw data from the various scans are assembled into a three dimensional data array, where one axis is the time of a scan set corresponding to chromatographic retention time, a second axis corresponds to the scan number in the scan set corresponding to mobility drift time, and the third axis is channel number, corresponding to mass-to-charge ratio. A three-dimensional convolution is applied to the three-dimensional data array. Local maxima in the three dimensions locate ion peaks. The value of the apex of the peak provides the fourth ion property, the intensity integrated over the whole body of the peak, if a convolution filter is normalized for this purpose.

The three-dimensional convolution utilizes, for example, smoothing or $2^{nd}$ derivative filters, or combinations of such filters. A convolution filter's coefficients are optionally chosen to maximize a signal-to-noise ratio, minimize statistical-error properties, remove baseline backgrounds, and/or mitigate effects of ion interference. For more efficient computation, as indicated in the above description of the method 2400, the three-dimensional convolution is optionally applied to sub-volumes of the raw data. The sub-volumes are selected in response to the LC/MS data. The collapsed 2420 data are obtained by combining (such as adding) all mobility spectra. Optionally, dead-time corrections and lock mass corrections are incorporated into the method 2400, as are auto peak-width computations for each dimension.

The method 2400 is extensible to N sequential separations that produce N dimensions of separation-related data. Such data are optionally assembled as a N-dimensional hypercube, and a N-dimensional convolution is applied to all points in the hyper cube. Local maxima are found, for example, by comparing the intensity of a point to $3^N$ neighboring elements centered on each element in the N-dimensional space. Interpolation formulas locate the N-dimensional parameters of each peak, and the value at the N-dimensional peak apex is the intensity of the peak that accounts for all the counts or signal associated with the peak after the N-dimensional separation.

The method 2400 is optionally applied to centroid data. In a centroid approach, the only information recorded for a scan, in a scan set, is the peak information, where each peak is described by a mass and intensity. Each mass-intensity pair is replaced with a Gaussian peak whose width corresponds to the mass spectrometric resolution, e.g., a continuum representation of each spectrum is reconstructed from a peak list. The reconstructed, continuum spectra are assembled into a cube and analyzed.

As noted above, for reasons of efficiency, one optionally chooses not to apply a three-dimensional convolution filter to an entire volume of raw data; an operation-count needed to manipulate the data increases as the power of the number of dimensions. Using presently available processing equipment, a general three-dimensional convolution applied to all of the data obtained in a single LC/IMS/MS-based system injection would require, for example, days of computational time. The method 2400 potentially reduces the computation time to, for example, less than 1 hour, while providing results comparable to that obtained from a complete three-dimensional convolution. Additional computational efficiency is obtained, optionally, by approximating both two-dimensional and three-dimensional convolution filters with one-dimensional filters applied in sequence to linear arrays extracted from the data.

The following is an example of data calculation for an LC/IMS/MS-based system. Ion intensities are organized in a three-dimensional volume, where each data element is an intensity, measured as counts (C), and each element is subscripted by three variables, corresponding to retention time (T), mobility (D), and mass-to-charge ratio μ. Mathematically, each element of this three-dimensional data is labeled by three indices. Chemists generally refer to such data as "four-dimensional" data, thus regarding intensity as an extra dimension of data. The notation used for each data element in this example is $C_{i,j,k}$, where C is the counts measured at a data element specified by integer indices i, j, k. These indices correspond to scan number (retention time, $T_i$), scan set number (mobility, $D_j$), and channel number (mass-to-charge, $\mu_k$). Thus, we have that $$C_{i,j,k} = C(T_i, D_j, \mu_k).$$

In this example, the response of an ion in an LC/IMS/MS system is approximated as a Gaussian peak in three dimensions, where each ion produces counts that spread across characteristic peak widths.

The width of a peak in each of the three directions is a property of the modes of separation. The standard-deviation peak widths are $\sigma_T, \sigma_D, \sigma_\mu$ for the chromatographic, mobility, and mass spectral directions. The counts are distributed over data elements as $$C_{i,j,k} = \frac{C_V}{(2\pi)^{3/2} \sigma_T \sigma_D \sigma_\mu} \exp\left(-\frac{1}{2}\left[\left(\frac{i-i_o}{\sigma_T}\right)^2 + \left(\frac{j-j_o}{\sigma_D}\right)^2 + \left(\frac{k-k_o}{\sigma_\mu}\right)^2\right]\right)$$

where $C_V$ is the integrated volume counts, and the i,j,k indices correspond to chromatographic scan time, mobility scan time, and mass-to-charge channel, respectively. The Gaussian peak is centered on $i_o, j_o$, and $k_o$ (which takes on a fractional value.) The relationship between apex counting rate and integrated volume counting rate is $$C_A = \frac{C_V}{(2\pi)^{3/2}\sigma_T\sigma_D\sigma_\mu}.$$

To detect ions in such data and measure their properties, i.e., to infer $i_o$, $j_o$, $k_o$, and $C_V$ from the array $C_{i,j,k}$, in this example, one estimates these parameters using a convolution filter. The local maxima of the convolved data locate the ions and estimate their intensity.

Given a set of filter coefficients, $F_{l,m,n}$, the output of a three-dimensional convolution is a three-dimensional volume, given by $$R_{i,j,k} = \sum_{l=-L}^{L} \sum_{m=-M}^{M} \sum_{n=-N}^{N} F_{l,m,n} C_{i-l,j-m,k-m}.$$

where $R_{i,j,k}$ as a convolution element.

The filter coefficients $F_{l,m,n}$ span a three-dimensional volume, where the width of each dimension is associated with the width of the peak in each dimension. The indices of F are symmetric about 0, and the number of elements in each dimension is (2L+1), (2M+1), and (2N+1).

In this example, the widths of $F_{l,m,n}$ are adjusted to match the changing peak widths over the MS and IMS dimensions. The computation of each output value $R_{i,j,k}$ requires as many multiplications as there are filter coefficients.

As indicated by the convolution expression, a value of $R_{i,j,k}$ is obtained by centering the coefficients $F_{l,m,n}$ on the element $C_{i,j,k}$, and performing the indicated multiplications and additions. Generally, there are as many output values $R_{i,j,k}$ as there are input values $C_{i,j,k}$.

In a three-dimensional application, $R_{i,j,k}$ is a local maximum if its value exceeds the value of all of its neighbors. That is, if $R_{i,j,k}$ is in the center of a (3×3×3=27) element cube, the value for $R_{i,j,k}$ is a maximum if its ion-peak intensity value exceeds that of its 26 nearest neighbors. A normalization coefficient is obtained by convolving the un-normalized filter with a model Gaussian peak; the peak widths of the model Gaussian peak correspond to the physically expected peak widths. An ion is detected if the value of the convolution maximum exceeds a suitably selected threshold. A value for threshold detection is set at, for example, 100 counts or less.

Given a peak-detection, the location of its apex in three-dimensions is obtained, for example, by fitting a three-dimensional quadratic curve to the 27 elements near the maximum. The interpolated index values of the maximum give the peak's properties, yielding fractional indices corresponding to retention time, mobility, and mass-to-charge ratio of the ion. Generally, spectra are uncalibrated, so the mass-to-charge is uncalibrated.

The operation count for convolution is proportional to the product of the number of acquired intensities times the number of filter coefficients. The operation count increases as the power of the dimensionality of the data. A convolution approach to a LC/IMS/MS-based system then optionally must contend with a potentially large operation count.

As mentioned above, one way to reduce the number of operations of a computation is to implement three-dimensional convolution filters as a series of one-dimensional convolution filters. Multiple applications of one-dimensional filters implements, as an approximation, a two-dimensional or three-dimensional filter matrix, as described above with reference to FIGS. 1-23. For example, a 21×21 element two-dimensional convolution matrix is replaced with four one-dimensional convolutions, two in the spectral direction and two in the retention time dimension. In the case of a three-dimensional convolution, a 21×21×21 three-dimensional convolution filter is replaced with nine one-dimensional convolutions, three one-dimensional convolutions in each dimension. This approach reduces calculation time, for example, by a factor of 6 in the two-dimensional case and a factor of 48 in the three-dimensional case.

As described above, one need not compute convolution elements for all raw data points to provide ion detection. Preferably, one only calculates enough values for $R_{i,j,k}$ to locate the local maximum of each ion. The minimum number is, for example, a cube of 3×3×3 values of $R_{i,j,k}$ for each ion. A local maximum is found if the value of $R_{i,j,k}$ in the center of that cube is greater than all surrounding 26 values. Thus, in principle, if there are 100,000 ions to be found, one only needs about 3,000,000 elements, or less than 0.01% of the $4.5 \times 10^{10}$ total number of potential convolution elements, in one illustrative example. The computation of these critical convolution values optionally requires a few seconds. In practice, more elements than this minimum are calculated. Thus, the invention, in some embodiments, exploits the realization that the addition of an IMS module to an LC/MS system optionally greatly increases the number of measured data points, most of which do not provide required information.

In this example, the raw data is collapsed in the ion-mobility dimension by constructing a two-dimensional LC/MS data matrix from the three-dimensional LC/IMS/MS data. An element $\hat{C}_{i,k}$ of the two-dimensional LC/MS matrix is obtained by summing intensities from all mobilities measured at the same chromatographic scan time and mass spectral channel, as follows, $$\hat{C}_{i,k} = \sum_{j=0}^{N_j} C_{i,j,k}.$$

As described above, one preferably sums over the mobility dimension because this dimension has the lowest resolution or peak capacity; the resulting T×µ two-dimensional array then has more resolution elements than the other two possible pairs of dimensions.

A two-dimensional convolution is applied to this collapsed array to determine an array of convolved elements $\hat{R}_{i,k}$, where $$\hat{R}_{i,k} = \sum_{l=-L}^{L} \sum_{n=-N}^{N} \hat{F}_{l,n} \hat{C}_{i-l,k-m}.$$

Here, $\hat{F}_{l,n}$ is a two-dimensional convolution filter, and $\hat{R}_{i,k}$ is the two-dimensional convolution element. The local maxima of $\hat{R}_{i,k}$ locates the retention time and m/z of each two-dimensional ion found in the two-dimensional matrix.

The present example utilizes the assumption that all ions are accounted for by these two-dimensional ion peaks (which may arise from more than one ion due to similar ion motilities.) Thus, the results of the two-dimensional convolution indicates where to apply the three-dimensional convolution, and each two-dimensional ion peak will correspond to one or more three-dimensional ions. If there is no ion interference for a particular two-dimensional ion peak, then the corresponding three-dimensional volume will yield a single ion detection with its location in the ion-mobility dimension.

For each two-dimensional ion-peak location determination, a set of three-dimensional convolution elements are calculated. In the present example, for each located peak, these elements span a three-dimensional volume that is centered on the retention time and m/z of the two-dimensional peak location and spans all 200 mobility spectra.

Thus, the three-dimensional data provide the ions' mobility characteristics, while the retention time, m/z, and/or intensity information was already provided by the convolved two-dimensional data or, preferably, also provided, more accurately, by the original three-dimensional data. Thus, it is sufficient to compute a limited selection of three-dimensional convolution elements.

To accommodate peaks, located in convolved two-dimensional data, that may include multiple ions whose apices are distributed over a width of the located peak, the following scheme is optionally adopted. Convolution elements are computed over a volume of 11 retention time elements by 11 mass-to-charge elements by 200 ion-mobility elements, centered on each two-dimensional ion detection. For this example, assuming 200 million calculational operations per second, approximately 38 minutes of processing time provides the retention time, ion mobility, mass-to-charge ratio, and ion intensity for all ions in a single sample injection in an LC/IMS/MS system. Reducing the volume over which three-dimensional convolution elements are computed additionally reduces computation time (by another factor of 20, for example) to a manageable level.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of LC/IMS/MS analysis, comprising:
   obtaining, from a sample, noisy raw data comprising a set of three-dimensional data elements each associating an ion-count intensity with a retention-time dimension, an ion-mobility dimension, and a mass-to-charge-ratio dimension, wherein the noise is associated with ion-peak artifacts;
   collapsing, in the ion-mobility dimension, the set of data elements to obtain a set of collapsed data elements each associating a combined ion-count intensity with the retention-time and mass-to-charge-ratio dimensions;
   convolving the set of collapsed data elements with an artifact-reducing filter associated with a two-dimensional matrix, thereby obtaining a convolved set of collapsed data elements having reduced peak artifacts;
   locating, in the retention-time and mass-to-charge-ratio dimensions, ion peaks of the convolved set of collapsed data elements;
   selecting one or more portions of the noisy raw data for further analysis, in response to the located ion peaks of the convolved set of collapsed data elements;
   convolving the selected one or more portions of the noisy raw data with an artifact-reducing filter associated with a three-dimensional matrix; and
   locating, in the ion mobility dimension, one or more ion peaks for each convolved portion of the raw data.

2. The method of claim 1, wherein locating the one or more ion peaks for each convolved portion of the raw data further comprises locating the one or more ion peaks in the retention-time- and mass-to-charge-ratio dimensions of the convolved portion of the raw data.

3. The method of claim 2, further comprising comparing, for a located ion peak, the retention-time and mass-to-charge-ratio dimensions of the convolved portion of the raw data to the retention-time and mass-to-charge-ratio dimensions of the convolved set of collapsed data elements.

4. The method of claim 1, wherein locating the one or more ion peaks for each convolved portion of the raw data comprises locating at least two ion peaks in the ion mobility dimension that overlap in the retention-time and mass-to-charge-ratio dimensions.

5. The method of claim 1, further comprising locating, in the retention-time and mass-to-charge-ratio dimensions, overlapping ion peaks of the convolved one or more portions of the raw data.

6. The method of claim 1, wherein the one, or more portions each consist of a restricted ranges, of the noisy raw data, in the retention-tune and mass-to-charge-ratio dimensions and an unrestricted range in, the ion-mobility dimension.

7. The method of claim 6, wherein the restricted ranges of each portion are substantially centered on the associated located ion peak.

8. The method of claim 1, wherein locating ion peaks comprises determining local ion-intensity maxima of the convolved raw data.

9. The method of claim 1, further comprising fitting a curve to at least one of the located one or more ion peaks to improve an accuracy of location in at least the mass-to-charge-ratio dimension of the at least one peak.

10. The method of claim 9, wherein fitting a curve comprises fitting a curve to three greatest ion-intensity values associated with a local maximum.

11. The method of claim 10, wherein the curve is based on a quadratic.

12. The method of claim 1, further comprising fitting a curve to at least one of the located one or more ion peaks to improve an accuracy of location in at least the ion-mobility dimension of the at least one peak.

13. The method of claim 1, further comprising fitting a curve to at least one of the located one or more ion peaks to improve an accuracy of location in at least the retention time dimension of the at least one peak.

14. The method of claim 1, further comprising normalizing elements of the three-dimensional matrix so that a height of the one or more located peaks is associated with a total peak ion count.

15. A method for analyzing a sample, comprising:
   obtaining noisy raw data from the sample, the data comprising a set of data elements each associating an ion-count intensity with at least three dimensions of differing resolution, wherein the noise is associated with ion-peak artifacts;

collapsing, at least in the dimension having the lowest resolution, the set of data elements to obtain a set of collapsed data elements each associating a combined ion-count intensity with the remainder of the at least three dimensions;

convolving the set of collapsed data elements with an artifact-reducing filter, the filter associated with a matrix having the same number of dimensions as the collapsed data elements, thereby obtaining a convolved set of collapsed data elements having reduced peak artifacts;

locating, in the remainder of the at least three dimensions, ion, peaks of the convolved set of collapsed data elements;

selecting one or more portions of the noisy raw data for further analysis, the one or more portions being associated with the locations of the ion peaks of the convolved set of collapsed data elements;

convolving the selected one or more portions of the noisy raw data with an artifact-reducing filter associated with a matrix having the same number of dimensions as the noisy raw data; and locating, in the lowest resolution dimension, one or more ion peaks for each of the convolved selected one or more portions of the noisy raw data.

16. The method of claim 15, wherein locating the one or more ion peaks for each of the portions further comprises locating the one or more ion peaks in the retention-time and mass-to-charge-ratio dimensions in each of the portions.

17. An apparatus for chemical processing, comprising:
a chromatography module;
an ion-mobility module;
a mass-spectrometry module; and
a control unit, in communication with the modules, comprising at least one processor and at least one memory for storing a plurality of instructions, which, when executed by the at least one processor, causes implementation of the steps of
obtaining, from a sample, noisy raw data comprising a set of three-dimensional data elements each associating an ion-count intensity with a retention-time dimension, an ion-mobility dimension, and a mass-to-charge-ratio dimension, wherein the noise is associated with ion-peak artifacts;
collapsing, in the ion-mobility dimension, the set of data elements to obtain a set of collapsed data elements each associating a combined ion-count intensity with the retention-time and mass-to-charge-ratio dimensions;
convolving the set of collapsed data elements with an artifact-reducing filter associated with a two-dimensional matrix, thereby obtaining a convolved set of collapsed data elements having reduced peak artifacts;
locating, in the retention-time and mass-to-charge-ratio dimensions, ion peaks of the convolved set of collapsed data elements;
selecting one or more portions of the noisy raw data for further analysis, in response to the located on peaks of the convolved set of collapsed data elements;

convolving the selected one or more portions of the noisy raw data with an artifact-reducing filter associated with a three-dimensional matrix; and locating, in the ion mobility dimension, one or more ion peaks for each convolved selected one or more portions of the raw data.

18. An apparatus, comprising:
analytical modules configured to obtain noisy raw data from the sample, the data comprising a set of data elements each associating an ion-count intensity with at least three dimensions of differing resolution, wherein the noise is associated with ion-peak artifacts;
means for collapsing, at least in the dimension having the lowest resolution, the set of data elements to obtain a reduced set of collapsed data elements each associating a combined ion-count intensity with the remainder of the at least three dimensions;
means for convolving the set of collapsed data elements with an artifact-reducing filter, the filter associated with a matrix having the same number of dimensions as the collapsed data elements, thereby obtaining a convolved set of collapsed data elements having reduced peak artifacts;
means for locating, in the remainder of the at least three dimensions, ion peaks of the convolved set of collapsed data elements;
means for selecting one or more portions of the noisy raw data for further analysis, the one or more portions being associated with the locations of the ion peaks of the convolved set of collapsed data elements;
means for convolving the selected one or more portions of the noisy raw data with an artifact-reducing filter associated with a matrix having the same number of dimensions as the noisy raw data; and
means for locating, in the lowest resolution dimension, one or more ion peaks for each of the convolved selected one or more portions of the noisy raw data.

19. A method of LC/IMS/MS analysis, comprising:
obtaining noisy raw data from a sample, the data comprising a set of three-dimensional data elements each associating an ion-count intensity with a retention-time dimension, an ion-mobility dimension, and a mass-to-charge-ratio dimension, wherein the noise is associated with ion-peak artifacts;
convolving the three-dimensional data elements with an artifact-reducing filter, the filter associated with a three-dimensional matrix, thereby obtaining a convolved set of data elements having reduced ion-peak artifacts; and
locating, in the retention-time, ion mobility, and mass-to-charge-ratio dimensions, one or more ion peaks of the convolved three-dimensional data elements.

20. The method of claim 19, wherein locating comprises associating an ion peak with a local maximum of ion intensity in the convolved three-dimensional data elements.

21. The method of claim 19, wherein at least two located peaks are overlapping in the retention-time, or mass-to-charge-ratio dimensions.

22. The method of claim 19, wherein at least two located peaks have substantially the same ion mobility.

* * * * *